US 7,842,474 B2

(12) United States Patent
Krah, III et al.

(10) Patent No.: US 7,842,474 B2
(45) Date of Patent: Nov. 30, 2010

(54) *EHRLICHIA CANIS* DIVA (DIFFERENTIATE INFECTED FROM VACCINATED ANIMALS)

(75) Inventors: Eugene Regis Krah, III, Freeport, ME (US); Thomas Patrick O'Connor, Jr., Westbrook, ME (US); Melissa Beall, Cape Elizabeth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 579 days.

(21) Appl. No.: 11/542,878

(22) Filed: Oct. 4, 2006

(65) Prior Publication Data

US 2009/0004217 A1  Jan. 1, 2009

Related U.S. Application Data

(63) Continuation-in-part of application No. 11/397,222, filed on Apr. 4, 2006, and a continuation-in-part of application No. PCT/US2006/012432, filed on Apr. 4, 2006.

(60) Provisional application No. 60/668,205, filed on Apr. 4, 2005.

(51) Int. Cl.
*G01N 33/569* (2006.01)
(52) U.S. Cl. .................................................. 435/7.32
(58) Field of Classification Search .................. None
See application file for complete search history.

(56) References Cited

U.S. PATENT DOCUMENTS

| 4,894,576 | A | 1/1990 | Okamoto et al. |
| 5,726,010 | A | 3/1998 | Clark |
| 6,043,085 | A | 3/2000 | Yu et al. |
| 6,355,777 | B1 | 3/2002 | Walker et al. |
| 6,392,023 | B1 | 5/2002 | Walker et al. |
| 6,403,780 | B1 | 6/2002 | Walker et al. |
| 6,458,942 | B1 | 10/2002 | Walker et al. |
| 6,660,269 | B2 * | 12/2003 | Walker et al. ............ 424/184.1 |
| 2002/0115840 | A1 | 8/2002 | Walker et al. |
| 2003/0073095 | A1 | 4/2003 | Walker et al. |
| 2003/0092087 | A1 | 5/2003 | Walker et al. |
| 2003/0096250 | A1 | 5/2003 | Walker et al. |
| 2003/0185849 | A1 | 10/2003 | Walker et al. |
| 2004/0121433 | A1 | 6/2004 | McBride et al. |
| 2004/0170972 | A1 | 9/2004 | Chang |
| 2004/0198951 | A1 | 10/2004 | Walker et al. |
| 2004/0247616 | A1 | 12/2004 | Walker et al. |
| 2005/0260621 | A1 | 11/2005 | McBride et al. |
| 2006/0211062 | A1 | 9/2006 | O'Connor, Jr. |
| 2006/0234322 | A1 * | 10/2006 | Krah et al. ................ 435/7.32 |
| 2007/0003570 | A1 | 1/2007 | Murtaugh et al. |
| 2009/0004217 | A1 | 1/2009 | Krah et al. |

FOREIGN PATENT DOCUMENTS

| WO | WO 98/42743 | 10/1998 |
| WO | WO 00/12688 | 3/2000 |
| WO | WO 01/82862 | 11/2001 |
| WO | WO 03/089571 | 10/2003 |
| WO | WO 2004/042037 | 5/2004 |
| WO | WO 2006/107924 | 10/2006 |
| WO | WO 2006107924 A2 * | 10/2006 |
| WO | WO 2006/138509 | 12/2006 |
| WO | WO 2008/112007 | 9/2008 |

OTHER PUBLICATIONS

Waner et al., Vet. Parasitol., 95:1-15, 2001.*
McBride et al., J. Clin. Micriobiol., 39:315-322, 2001.*
Yu et al. (J. Clin. Microbiol., 38:369-374, 2000.*
Waner, et al., "Significance of serological testing for ehrlichial diseases in dogs with special emphasis on the diagnosis of canine moncytic ehrlichiosis caused by *Ehrlichia canis*", Veterinary Parasitology 95 (2001) 1-15.
Cardenas, et al., "Enzyme-Linked Immunosorbent Assay with Conserved Immunoreactive Glycoproteins gp36 and gp19 has Enhanced Sensitivity and Provides Species-Specific Immunodiagnosis of *Ehrlichia canis* Infection", Clinical and Vaccine Immunology, vol. 14, No. 2, p. 123-128 (2007).
McBride, et al., "Kinetics of Antibody Response to *Ehrlichia canis* Immunoreactive Proteins", Infection and Immunity, vol. 71, No. 5, p. 2516-2524 (2003).
McBride, "Novel Immunoreactive glycoprotein orthologs of *Ehrlichia* spp.", Ann. NY Aca. Sci., 990:678-84, 2003—Abstract Only.
Office Action issued in correspondence U.S. Appl. No. 11/397,222 dated Jul. 18, 2008.
International Search Report and Written Opinion dated Feb. 2, 2007 for corresponding PCT application No. PCT/US2006/012432.
Yu, et al., "Molecular Cloning and Characterization of the 120-Kilodalton Protein Gene of *Ehrlichia canis* and Application of the Recombinant 120-Kilodalton Protein for Serodiagnosis of Canine Ehrlichiosis", Journal of Clinical Microbiology, vol. 38, No. 1, p. 369-374 (2000).
McBride, et al., "Immunodiagnosis of *Ehrlichia canis* Infection with Recombinant Proteins", Journal of Clinical Microbiology, vol. 39, No. 1, p. 315-322 (2001).
Mavromatis, et al., "The Genome of the Obligately Intracellular Bacterium *Ehrlichia canis* Reveals Themes of Complex Membrane Structure and Immune Evasion Strategies", Journal of Bacteriology, vol. 188, No. 11, p. 4015-4023 (2006).
Office action corresponding to U.S. Appl. No. 11/397,222 (U.S. Publ. No. 20060234322) dated Feb. 23, 2009.

(Continued)

*Primary Examiner*—Robert B Mondesi
*Assistant Examiner*—Brian J Gangle
(74) *Attorney, Agent, or Firm*—McDonnell Boehnen Hulbert & Berghoff LLP

(57) ABSTRACT

*Ehrlichia canis* antigens that can be used to differentiate *E. canis* infected animals from animals that have been challenged with *E. canis*, e.g., vaccinated against *E. canis*, are disclosed. The invention also provides compositions and methods for determining the presence of *E. canis* antigens and antibodies.

14 Claims, 4 Drawing Sheets

OTHER PUBLICATIONS

International Search Report and Written Opinion dated May 14, 2008 for corresponding PCT application No. PCT/US2007/080373.

Office Action issued in corresponding U.S. Appl. No. 11/397,222 dated Nov. 19, 2007.

Breitschwerdt, et al., "Doxycycline Hyclate Treatement of Experimental Canine Ehrlichiosis Followed by Challenge Inoculation with Two *Ehrliichia canis* Strains", Antimicrobial Agents and Chemotherapy, vol. 42, No. 2, p. 362-368, 1998.

Yu, et al., "Comparison of *Ehrlichia chaffeensis* Recombinant Proteins for Serologic Diagnosis of Human Monocytotropic Ehrlichiosis", Journal of Clinical Microbiology, vol. 37, No. 8, p. 2568-2575, 1999.

Yu, et al., "Molecular Cloning and characterization of the 120-Kilodalton Protein Gene of *Ehrlichia canis* and Application of the Recombinant 120-Kilodalton Protein for Serodiagnosis of Canine Ehrlichiosis", Journal of Clinical Microbiology, vol. 38, No. 1, p. 369-374, 2000.

Accession No. $NZ_{13}$ AAEJ01000001 dated Oct. 4, 2004 (first page only).

Accession No. ZP_00211244 dated Oct. 4, 2004.

Accession No. ZP_00211130 dated Oct. 4, 2004.

Accession No. AAE96254 dated Apr. 20, 2002.

Accession No. ZP_00210575 dated Oct. 4, 2004.

Accession No. AAK01145 dated Oct. 6, 2003.

Accession No. AF252298 dated Oct. 6, 2003.

Accession No. AAD34330 dated Jan. 13, 2000.

Accession No. AF112369 dated Jan. 13, 2000.

Accession No. ZP_00211146 dated Oct. 4, 2004.

Database, "Major outer membrane protein p19", Uniprot, Sep. 27, 2005. Retrieved from EBI Accession No. UNIPROT:Q3YSZ1, Database accession No. Q3YSZ1.

Mavromatis, et al., "The genome of the obligately intracellular bacterium *Ehrlichia canis* reveals themes of complex membrane structure and immune evasion strategies", J. Bacteriol. 2006; 88(11):4015-23.

McBride, et al., "Identification of a glycosylated *Ehrlichia canis* 19-kilodalton major immunoreactive protein with a species-specific serine-rich glycopeptide epitope", Infect. Immuno. 2007; 75(1):74-82.

McBride, et al., "Molecular cloning of the gene for a conserved major immunoreactive 28-kilodalton protein of *Ehrlichia canis*: a potential serodiagnostic antigen", Clin. Diagn. Lab. Immunol. 1999; 6(3):392-9.

Ndip, et al., "Ehrlichial Infection in Cameroonian canines by *Ehrlichia canis* and *Ehrlichia ewingii*", Vet. Microbiol. 2005; 111(1-2):59-66.

Office action dated Oct. 15, 2009, for U.S. Appl. No. 11/397,222 (US 2006-0234322).

Greenspan et al., "Defining epitopes: It's not as easy as it seems", Nature Biotechnology, vol. 17, pp. 936-937 (1999).

Holmes, "PSMA specific antibodies and their diagnostic and therapeutic use", Exp. Opin. Invest. Drugs, 10(3), pp. 511-519 (2001).

Houghten et al., "Relative Importance of Position and Individual Amino Acid Residues in Peptide Antigen-Antibody Interactions: Implications in the Mechanism of Antigenic Drift and Antigenic Shift", Vaccines 86, eds. Brown et al., Cold Spring Harbor Laboratory Press, pp. 21-25 (1986).

Office Action dated Apr. 1, 2010, for corresponding U.S. Appl. No. 12/262,709.

Gauither et al., "Western immunoblot analysis for distinguishing vaccination and infection status with *Borrelia burgdorferi* (Lyme disease) in dogs", J. Vet. Diagn. Invest., 11:259-265 (1999).

Office Action dated Apr. 14, 2010 for U.S. Appl. No. 11/397,222.

\* cited by examiner

FIG. 1   HTWM / LYME / EC: SNAP 3 DX

ALUMINUM OXIDE

RIBI

2D GEL ANALYSIS OF
ISOLATED *E. canis* - STAINED WITH
BIOSAFE COOMASIE BLUE

WESTERN BLOT OF *E. Canis* PROTEINS RESOLVED USING 2D
GELS PROBED WITH NORMAL CANINE PLASMA.

WESTERN ANALYSIS WITH VACCINATED SERA
POOL OF 4 VACCINATED DOGS - 1:100 pH10 ---------------------------------- pH3 kDa
191
64
51
39
28
19

WESTERN ANALYSIS WITH INFECTED SERA
POOL OF 3 POSITIVE DOGS - 1:100 pH10 ---------------------------------- pH3    MWM kDa
191
64
51
39
28
19

FIG. 6
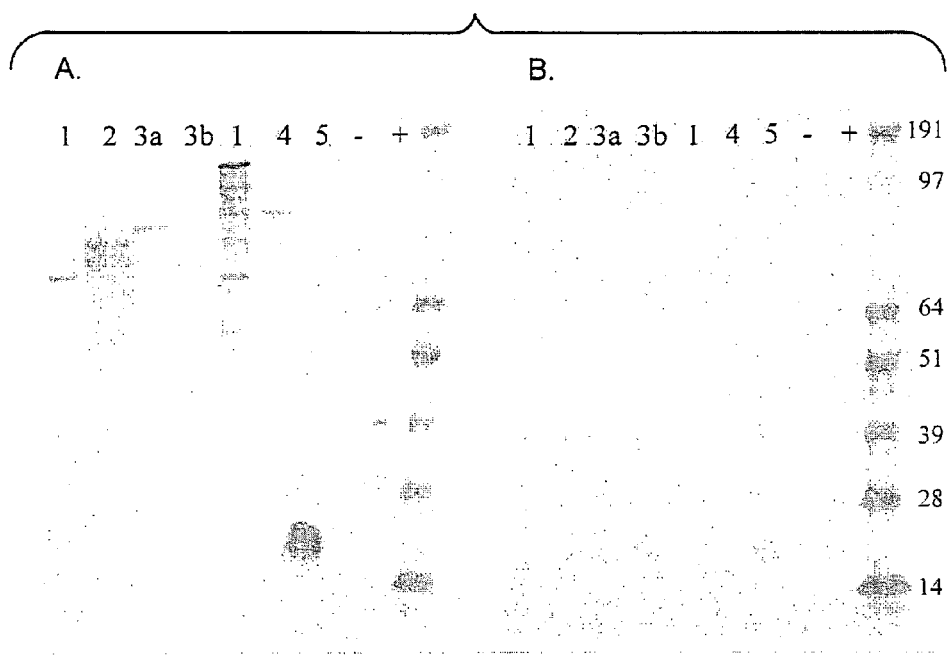
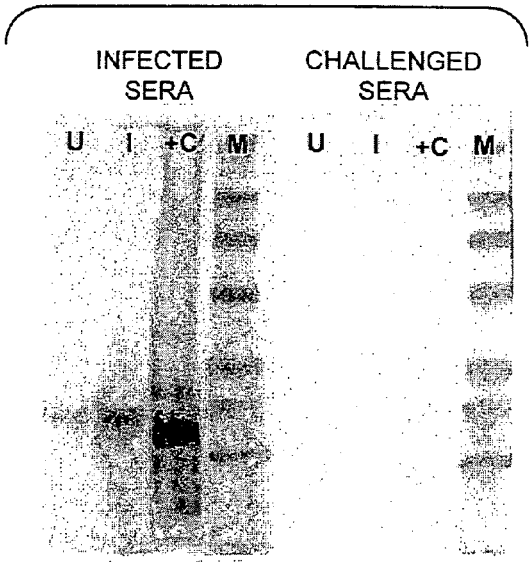
FIG. 7

SEQUENCE LISTING

<160> NUMBER OF SEQ ID NOS: 22

<210> SEQ ID NO 1
<211> LENGTH: 2067
<212> TYPE: DNA
<213> ORGANISM: Ehrlichia canis

<400> SEQUENCE: 1

```
atggatattg ataacaataa tgtgactaca tcaagtacgc aagataaaag tgggaattta    60
atggaagtga ttatgcgtat attaaatttt ggtaataatt cagatgagaa agtaagcaat   120
gaagacacta agttcttgt agagagttta caacctgctg tgaatgacaa tgtaggaaat    180
ccatcaagtg aagttggtaa agaagaaaat gctcctgaag ttaaagcgga agatttgcaa   240
cctgctgtag atggtagtgt agaacattca tcaagtgaag ttgggaaaaa agtatctgaa   300
actagtaaag aggaaagtac tcctgaagtt aaagcagaag atttgcaacc tgctgtagat   360
ggtagtatag aacattcatc aagtgaagtt ggagaaaaag tatctaaaac tagtaaagag   420
gaaagtactc ctgaagttaa agcagaagat ttgcaacctg ctgtagatga tagtgtggaa   480
cattcatcaa gtgaagttgg agaaaaagta tctgaaacta gtaaagagga aaatactcct   540
gaagttaaag cagaagattt gcaacctgct gtagatggta gtatagaaca ttcatcaagt   600
gaagttggag aaaaagtatc taaaactagt aaagaggaaa gtactcctga agttaaagca   660
gaagatttgc aacctgctgt agatgatagt gtggaacatt catcaagtga agttggagaa   720
aaagtatctg aaactagtaa agaggaaaat actcctgaag ttaaagcaga gatttgcaa    780
cctgctgtag atggtagtgt ggaacattca tcaagtgaag ttggagaaaa agtatctaaa   840
actagtaaag aggaaagtac tcctgaagtt aaagcagaag atttgcaacc tgctgtagat   900
gatagtgtgg aacattcatc aagtgaagtt ggagaaaaag tatctgaaac tagtaaagag   960
gaaaatactc ctgaagttag agcagaagat ttgcaacctg ctgtagatgg tagtgtgaa   1020
cattcatcaa gtgaagttgg agaaaaagta tctgaaacta gtaaagagga agtactcct   1080
gaagttaaag cagaagattt gcaacctgct gtagatagta gtatagaaca ttcatcaagt   1140
gaagttggga aaaagtatc tgaaactagt aaagaggaaa gtactcctga agttaaagca   1200
gaagatttgc aacctgctgt agatggtagt gtagaacatt catcaagtga agttggagaa   1260
aaagtatctg aaactagtaa agaggaaaat actcctgaag ttaaagcaga gatttgcaa    1320
```

```
cctgctgtag atggtagtgt agaacattca tcaagtgaag ttggagaaaa agtatctgaa    1380
actagtaaag aggaaaatac tcctgaagtt aaagcggaag atttgcaacc tgctgtagat    1440
ggtagtgtag aacattcatc aagtgaagtt ggagaaaaag tatctgaaac tagtaaagaa    1500
gaaagtactc ctgaagttaa agcagaagat ttgcaacctg ctgtagatga tagtgtagaa    1560
cattcatcaa gtgaagttgg agaaaaagta tctgaaacta gtaaagaaga agtactcct     1620 gaagttaaag cggaagattt gcaacctgct gtagatggta gtgtggaaca ttcatcaagt    1680
gaagttggag aaaagtatc tgagactagt aaagaggaaa gtactcctga agttaaagcg     1740
gaagtacagc ctgttgcaga tggtaatcct gttcctttaa atcctatgcc ttcaattgat    1800
aatattgata ctaatataat attccattac cataaagact gtaaaaaagg ttcagctgta    1860
ggaacagatg aaatgtgttg tcctgtatca gaattaatgg ctggggaaca tgttcatatg    1920
tatggaattt atgtctatag agttcaatca gtaaaggatt taagtggtgt atttaatata    1980
gatcattcta catgtgattg taatttagat gtttattttg taggatacaa ttcttttact    2040
aacaaagaaa cagttgattt aatataa                                        2067
```

<210> SEQ ID NO 2
<211> LENGTH: 688
<212> TYPE: PRT
<213> ORGANISM: Ehrlichia canis

<400> SEQUENCE: 2

```
Met Asp Ile Asp Asn Asn Asn Val Thr Thr Ser Ser Thr Gln Asp Lys
1               5                   10                  15

Ser Gly Asn Leu Met Glu Val Ile Met Arg Ile Leu Asn Phe Gly Asn
            20                  25                  30

Asn Ser Asp Glu Lys Val Ser Asn Glu Asp Thr Lys Val Leu Val Glu
        35                  40                  45

Ser Leu Gln Pro Ala Val Asn Asp Asn Val Gly Asn Pro Ser Ser Glu
    50                  55                  60

Val Gly Lys Glu Glu Asn Ala Pro Glu Val Lys Ala Glu Asp Leu Gln
65                  70                  75                  80

Pro Ala Val Asp Gly Ser Val Glu His Ser Ser Glu Val Gly Lys
                85                  90                  95

Lys Val Ser Glu Thr Ser Lys Glu Glu Ser Thr Pro Glu Val Lys Ala
            100                 105                 110

Glu Asp Leu Gln Pro Ala Val Asp Gly Ser Ile Glu His Ser Ser Ser
        115                 120                 125

Glu Val Gly Glu Lys Val Ser Lys Thr Ser Lys Glu Glu Ser Thr Pro
    130                 135                 140

Glu Val Lys Ala Glu Asp Leu Gln Pro Ala Val Asp Ser Val Glu
145                 150                 155                 160

His Ser Ser Ser Glu Val Gly Glu Lys Val Ser Glu Thr Ser Lys Glu
                165                 170                 175

Glu Asn Thr Pro Glu Val Lys Ala Glu Asp Leu Gln Pro Ala Val Asp
            180                 185                 190

Gly Ser Ile Glu His Ser Ser Glu Val Gly Glu Lys Val Ser Lys
        195                 200                 205

Thr Ser Lys Glu Glu Ser Thr Pro Glu Val Lys Ala Glu Asp Leu Gln
    210                 215                 220

Pro Ala Val Asp Asp Ser Val Glu His Ser Ser Ser Glu Val Gly Glu
225                 230                 235                 240
```

-continued

```
Lys Val Ser Glu Thr Ser Lys Glu Glu Asn Thr Pro Glu Val Lys Ala
            245                 250                 255
Glu Asp Leu Gln Pro Ala Val Asp Gly Ser Val Glu His Ser Ser Ser
        260                 265                 270
Glu Val Gly Glu Lys Val Ser Lys Thr Ser Lys Glu Glu Ser Thr Pro
    275                 280                 285
Glu Val Lys Ala Glu Asp Leu Gln Pro Ala Val Asp Asp Ser Val Glu
290                 295                 300
His Ser Ser Ser Glu Val Gly Glu Lys Val Ser Glu Thr Ser Lys Glu
305                 310                 315                 320
Glu Asn Thr Pro Glu Val Arg Ala Glu Asp Leu Gln Pro Ala Val Asp
                325                 330                 335
Gly Ser Val Glu His Ser Ser Glu Val Gly Glu Lys Val Ser Glu
            340                 345                 350
Thr Ser Lys Glu Glu Ser Thr Pro Glu Val Lys Ala Glu Asp Leu Gln
        355                 360                 365
Pro Ala Val Asp Ser Ser Ile Glu His Ser Ser Glu Val Gly Lys
    370                 375                 380
Lys Val Ser Glu Thr Ser Lys Glu Glu Ser Thr Pro Glu Val Lys Ala
385                 390                 395                 400
Glu Asp Leu Gln Pro Ala Val Asp Gly Ser Val Glu His Ser Ser Ser
                405                 410                 415
Glu Val Gly Glu Lys Val Ser Glu Thr Ser Lys Glu Glu Asn Thr Pro
            420                 425                 430
Glu Val Lys Ala Glu Asp Leu Gln Pro Ala Val Asp Gly Ser Val Glu
        435                 440                 445
His Ser Ser Ser Glu Val Gly Glu Lys Val Ser Glu Thr Ser Lys Glu
    450                 455                 460
Glu Asn Thr Pro Glu Val Lys Ala Glu Asp Leu Gln Pro Ala Val Asp
465                 470                 475                 480
Gly Ser Val Glu His Ser Ser Glu Val Gly Glu Lys Val Ser Glu
                485                 490                 495
Thr Ser Lys Glu Glu Ser Thr Pro Glu Val Lys Ala Glu Asp Leu Gln
            500                 505                 510
Pro Ala Val Asp Asp Ser Val Glu His Ser Ser Glu Val Gly Glu
        515                 520                 525
Lys Val Ser Glu Thr Ser Lys Glu Glu Ser Thr Pro Glu Val Lys Ala
    530                 535                 540
Glu Asp Leu Gln Pro Ala Val Asp Gly Ser Val Glu His Ser Ser Ser
545                 550                 555                 560
Glu Val Gly Glu Lys Val Ser Glu Thr Ser Lys Glu Glu Ser Thr Pro
                565                 570                 575
Glu Val Lys Ala Glu Val Gln Pro Val Ala Asp Gly Asn Pro Val Pro
            580                 585                 590
Leu Asn Pro Met Pro Ser Ile Asp Asn Ile Asp Thr Asn Ile Ile Phe
        595                 600                 605
His Tyr His Lys Asp Cys Lys Lys Gly Ser Ala Val Gly Thr Asp Glu
    610                 615                 620
Met Cys Cys Pro Val Ser Glu Leu Met Ala Gly Glu His Val His Met
625                 630                 635                 640
Tyr Gly Ile Tyr Val Tyr Arg Val Gln Ser Val Lys Asp Leu Ser Gly
                645                 650                 655
```

```
Val Phe Asn Ile Asp His Ser Thr Cys Asp Cys Asn Leu Asp Val Tyr
                660                 665                 670

Phe Val Gly Tyr Asn Ser Phe Thr Asn Lys Glu Thr Val Asp Leu Ile
            675                 680                 685

<210> SEQ ID NO 3
<211> LENGTH: 3186
<212> TYPE: DNA
<213> ORGANISM: Ehrlichia canis

<400> SEQUENCE: 3
aatttagatt ttggacttgt agatggagat ggtaaaaatc ctttacatca tgctgttgaa      60
catttgccac ctgttatact taagggcgta atggaccatg taaaaaatag tagtgagttt     120
caagatttag taaatgatcc tgattatttt ggaaatacta tagctcatta tgcagttaag     180
aataaaaatg ctgatttaac attgtttaac atgctgaaag cttcaggagc tgatttaaat     240
gttaggaatg tagttggtcg agctccaata catgttgctt cttctaatgg taaggctaat     300
gcagtttctg gacttgtatc atgtggtatt gacgttaatt ctcaagatgt gaatggagat     360
acaccacttc atattgctgt tgaaggcggt agtatggaga cggtattagc agtgttaaat     420
cagagaggtg ctgatgttag tgtccagaat aacgatggag ttacacctat gcttagtgct     480
gctaaatatg gagatatagg tgtaataaaa gctttaggtt cagctaaacc aaatattaaa     540
ggtgaagaca ctgttgctaa atcattgctg atggaggatt acaaaggttt tacacccttg     600
cattttgtag ctggtggtgg tagcagagat acattccgtg tcgtaagaaa aaattatgaa     660
aaatgtcatg acttagctac tattagggca gctttaatgc aagatagaag tggtggtgag     720
cttgtaaatt taggggattt tgaaagtgaa aatatattgg gttcgccaaa tgcaaaattc     780
ttgcagcata ttcaatcagc aaattttggt ttttctccag cgcattgtgc tatagtatcg     840
tctaatcaca atgtaatgaa agatatctta aattttgttg gggattcgtt acacctacca     900
agtgagcgtg ggtataatgc aatgcaggtt gctgctttgt ttggtgacaa agaagcagtg     960
aaaatgcttg ctaaaagtgc taagccaagt gatcttaatt ttaagacttc agcaactcct    1020
actccgttaa atcttgcatg tcttagaggt gataatgagg tagtacgtgg gttagtaggt    1080
caacatggta ttgacattaa ccaacgtatg ggaagtgata aaaacactgt attgcattat    1140
gcaatcagca aaggagatag ttttcttgtg caaaagatat tagctcatac tggagttgat    1200
gttaattgtg agaataacct aggtcaaacg cctttacatt tagcagttga gggaggagat    1260
cctaagatag tatcttctct tcttaaagct ggtgcagtag ttaatcgtct ggatgataat    1320
ggtagatctg tactttcttc tgcgatagtt ccaggtagaa aagaaaaggg agtgctgggt    1380
atagttaata aattgctgga tagaggtgca gatattaatt tagatggaga ccacaatata    1440 cttttttgatc agtgtctaag gggtggatat aataatgtat tagataagtt aatacaacaa    1500 gggggttgaag ttaatcgaaa tagtgaaata cgtccaatgg tttatgctgc aatatctggt    1560
aatgagcatg ctatcaaatc attagctaat gctggtggag atgttaatga agtagtaaat    1620
aatccatcta gtaggcattc aggaaatcct ttaattatgg ttgcagtagc agatggtaat    1680
gcaggtcttc ttaaaacatt agtttctgaa ggatgtgatg ttggtaaatc tggaaaagat    1740
ggtaatacag cgttacatta tgctgttagt cattcagata aagagtttgg taataaagct    1800
ataaagatat taatttcacg taatagtgtt gggactaata gagatattct tactcaaaag    1860
aataacgcag gtgatacacc tttacatgaa gctcttaagt caggtaatat taattctgta    1920
cagaatatct taagtgctgt acatccaaga tacgcaaagg agatattaac agccagagac    1980
```

-continued

```
aaagaagggt acacaccaat gcattatact gttggagtaa ataatgttga tgttggtaga    2040
agtattctag agtctatgct ctctaaaggt gtgaataatc ttggagagat tgttggagca    2100
caggatagta attttcgaac acctctgcat gctgctatta aaatatctga ttatcgtgct    2160
gcggacatga taataggtag cttatcgaaa acagaattgt caaagttatc gcaattaaca    2220
gatattaacg gggatacacc actacatctt tcttgtcagt ctggtaatgt cgagatgaca    2280
caattctttc ttggaggttt ggataaacgt gaattaccta agacattaaa gatagcaaat    2340
aaaaatggag atactccttt acatgatgct ataagaaatg atgatattaa atctgcaaaa    2400
atgatgatta ggaattgtaa caaagaagaa cttgctaatg tattaaaatg taaagatagt    2460
tttggtaata cagtattgca tactattgct gaccaagtta ttgcgaatcc agaatcaaag    2520
aaagaccttg atggtttgat gaatttagca gtgaaaaggc taaagaatca agatctgaaa    2580
gatctagtta atacgcgaaa taactctgac gatactgttg cacattgtgc tcttttatcg    2640
gatatgaaat atgctcaaaa gatacttaaa tcatgtaacc atgatacatt agtgagagga    2700
aatagtaata atcaatcttt atcagagtgt attcgtgatg atagtaaaata taaaaaaggt    2760 ggaattttta gtaagtcttt atttttcaaaa ttaaagaaac ttgaggcacg agctgccagc    2820
gctagttatg aagaattatc tagtatcagt agtggtagtg atgtttcttc tgtatcaaca    2880
aatagcacag aagtaagtgc agtacctgaa gtggcaagaa gtagtggtgc tgtgtcgttc    2940
aaacatgtgc aagaaacagg agttgacacg tctggtcctt ctgatataga aagtttagag    3000
agattatctg atactagtct tgggtcaaat gattttgatc agcgaatggc agatttagat    3060
caagaaatag caaatattgt tagtggttta ccagaagtta cccaggtagc tgtaagtcaa    3120
caacaagcag catctcctag ttcaggtcaa gctgctggtg tgcaacaaaa agagatgcag    3180
agataa                                                                3186
```

<210> SEQ ID NO 4
<211> LENGTH: 1061
<212> TYPE: PRT
<213> ORGANISM: Ehrlichia canis

<400> SEQUENCE: 4

```
Asn Leu Asp Phe Gly Leu Val Asp Gly Asp Gly Lys Asn Pro Leu His
1               5                   10                  15

His Ala Val Glu His Leu Pro Pro Val Ile Leu Lys Gly Val Met Asp
            20                  25                  30

His Val Lys Asn Ser Ser Glu Phe Gln Asp Leu Val Asn Asp Pro Asp
        35                  40                  45

Tyr Phe Gly Asn Thr Ile Ala His Tyr Ala Val Lys Asn Lys Asn Ala
    50                  55                  60

Asp Leu Thr Leu Phe Asn Met Leu Lys Ala Ser Gly Ala Asp Leu Asn
65                  70                  75                  80

Val Arg Asn Val Val Gly Arg Ala Pro Ile His Val Ala Ser Ser Asn
                85                  90                  95

Gly Lys Ala Asn Ala Val Ser Gly Leu Val Ser Cys Gly Ile Asp Val
            100                 105                 110

Asn Ser Gln Asp Val Asn Gly Asp Thr Pro Leu His Ile Ala Val Glu
        115                 120                 125

Gly Gly Ser Met Glu Thr Val Leu Ala Val Leu Asn Gln Arg Gly Ala
    130                 135                 140

Asp Val Ser Val Gln Asn Asn Asp Gly Val Thr Pro Met Leu Ser Ala
```

```
                145                 150                 155                 160
Ala Lys Tyr Gly Asp Ile Gly Val Ile Lys Ala Leu Gly Ser Ala Lys
                165                 170                 175

Pro Asn Ile Lys Gly Glu Asp Thr Val Ala Lys Ser Leu Leu Met Glu
                180                 185                 190

Asp Tyr Lys Gly Phe Thr Pro Leu His Phe Val Ala Gly Gly Gly Ser
                195                 200                 205

Arg Asp Thr Phe Arg Val Val Arg Lys Asn Tyr Glu Lys Cys His Asp
                210                 215                 220

Leu Ala Thr Ile Arg Ala Ala Leu Met Gln Asp Arg Ser Gly Gly Glu
225                 230                 235                 240

Leu Val Asn Leu Gly Asp Phe Glu Ser Glu Asn Ile Leu Gly Ser Pro
                245                 250                 255

Asn Ala Lys Phe Leu Gln His Ile Gln Ser Ala Asn Phe Gly Phe Ser
                260                 265                 270

Pro Ala His Cys Ala Ile Val Ser Ser Asn His Asn Val Met Lys Asp
                275                 280                 285

Ile Leu Asn Phe Val Gly Asp Ser Leu His Leu Pro Ser Glu Arg Gly
                290                 295                 300

Tyr Asn Ala Met Gln Val Ala Ala Leu Phe Gly Asp Lys Glu Ala Val
305                 310                 315                 320

Lys Met Leu Ala Lys Ser Ala Lys Pro Ser Asp Leu Asn Phe Lys Thr
                325                 330                 335

Ser Ala Thr Pro Thr Pro Leu Asn Leu Ala Cys Leu Arg Gly Asp Asn
                340                 345                 350

Glu Val Val Arg Gly Leu Val Gly Gln His Gly Ile Asp Ile Asn Gln
                355                 360                 365

Arg Met Gly Ser Asp Lys Asn Thr Val Leu His Tyr Ala Ile Ser Lys
                370                 375                 380

Gly Asp Ser Phe Leu Val Gln Lys Ile Leu Ala His Thr Gly Val Asp
385                 390                 395                 400

Val Asn Cys Glu Asn Asn Leu Gly Gln Thr Pro Leu His Leu Ala Val
                405                 410                 415

Glu Gly Gly Asp Pro Lys Ile Val Ser Ser Leu Leu Lys Ala Gly Ala
                420                 425                 430

Val Val Asn Arg Leu Asp Asp Asn Gly Arg Ser Val Leu Ser Ser Ala
                435                 440                 445

Ile Val Pro Gly Arg Lys Glu Lys Gly Val Leu Gly Ile Val Asn Lys
                450                 455                 460

Leu Leu Asp Arg Gly Ala Asp Ile Asn Leu Asp Gly Asp His Asn Ile
465                 470                 475                 480

Leu Phe Asp Gln Cys Leu Arg Gly Gly Tyr Asn Asn Val Leu Asp Lys
                485                 490                 495

Leu Ile Gln Gln Gly Val Glu Val Asn Arg Asn Ser Glu Ile Arg Pro
                500                 505                 510

Met Val Tyr Ala Ala Ile Ser Gly Asn Glu His Ala Ile Lys Ser Leu
                515                 520                 525

Ala Asn Ala Gly Gly Asp Val Asn Glu Val Val Asn Asn Pro Ser Ser
                530                 535                 540

Arg His Ser Gly Asn Pro Leu Ile Met Val Ala Val Ala Asp Gly Asn
545                 550                 555                 560

Ala Gly Leu Leu Lys Thr Leu Val Ser Glu Gly Cys Asp Val Gly Lys
                565                 570                 575
```

-continued

```
Ser Gly Lys Asp Gly Asn Thr Ala Leu His Tyr Ala Val Ser His Ser
            580                 585                 590
Asp Lys Glu Phe Gly Asn Lys Ala Ile Lys Ile Leu Ile Ser Arg Asn
        595                 600                 605
Ser Val Gly Thr Asn Arg Asp Ile Leu Thr Gln Lys Asn Asn Ala Gly
    610                 615                 620
Asp Thr Pro Leu His Glu Ala Leu Lys Ser Gly Asn Ile Asn Ser Val
625                 630                 635                 640
Gln Asn Ile Leu Ser Ala Val His Pro Arg Tyr Ala Lys Glu Ile Leu
            645                 650                 655
Thr Ala Arg Asp Lys Glu Gly Tyr Thr Pro Met His Tyr Thr Val Gly
        660                 665                 670
Val Asn Asn Val Asp Val Gly Arg Ser Ile Leu Glu Ser Met Leu Ser
    675                 680                 685
Lys Gly Val Asn Asn Leu Gly Glu Ile Val Gly Ala Gln Asp Ser Asn
690                 695                 700
Phe Arg Thr Pro Leu His Ala Ala Ile Lys Ile Ser Asp Tyr Arg Ala
705                 710                 715                 720
Ala Asp Met Ile Ile Gly Ser Leu Ser Lys Thr Glu Leu Ser Lys Leu
            725                 730                 735
Ser Gln Leu Thr Asp Ile Asn Gly Asp Thr Pro Leu His Leu Ser Cys
        740                 745                 750
Gln Ser Gly Asn Val Glu Met Thr Gln Phe Phe Leu Gly Gly Leu Asp
    755                 760                 765
Lys Arg Glu Leu Pro Lys Thr Leu Lys Ile Ala Asn Lys Asn Gly Asp
770                 775                 780
Thr Pro Leu His Asp Ala Ile Arg Asn Asp Asp Ile Lys Ser Ala Lys
785                 790                 795                 800
Met Met Ile Arg Asn Cys Asn Lys Glu Glu Leu Ala Asn Val Leu Lys
            805                 810                 815
Cys Lys Asp Ser Phe Gly Asn Thr Val Leu His Thr Ile Ala Asp Gln
        820                 825                 830
Val Ile Ala Asn Pro Glu Ser Lys Lys Asp Leu Asp Gly Leu Met Asn
    835                 840                 845
Leu Ala Val Lys Arg Leu Lys Asn Gln Asp Leu Lys Asp Leu Val Asn
850                 855                 860
Thr Arg Asn Asn Ser Asp Asp Thr Val Ala His Cys Ala Leu Leu Ser
865                 870                 875                 880
Asp Met Lys Tyr Ala Gln Lys Ile Leu Lys Ser Cys Asn His Asp Thr
            885                 890                 895
Leu Val Arg Gly Asn Ser Asn Asn Gln Ser Leu Ser Glu Cys Ile Arg
        900                 905                 910
Asp Asp Ser Lys Tyr Lys Lys Gly Gly Ile Phe Ser Lys Ser Leu Phe
    915                 920                 925
Ser Lys Leu Lys Lys Leu Glu Ala Arg Ala Ala Ser Ala Ser Tyr Glu
930                 935                 940
Glu Leu Ser Ser Ile Ser Ser Gly Ser Asp Val Ser Ser Val Ser Thr
945                 950                 955                 960
Asn Ser Thr Glu Val Ser Ala Val Pro Glu Val Ala Arg Ser Ser Gly
            965                 970                 975
Ala Val Ser Phe Lys His Val Gln Glu Thr Gly Val Asp Thr Ser Gly
        980                 985                 990
```

```
Pro Ser Asp Ile Glu Ser Leu Glu Arg Leu Ser Asp Thr Ser Leu Gly
    995                1000               1005

Ser Asn Asp Phe Asp Gln Arg Met Ala Asp Leu Asp Gln Glu Ile
    1010               1015              1020

Ala Asn Ile Val Ser Gly Leu Pro Glu Val Thr Gln Val Ala Val
    1025               1030              1035

Ser Gln Gln Gln Ala Ala Ser Pro Ser Ser Gly Gln Ala Ala Gly
    1040               1045              1050

Val Gln Gln Lys Glu Met Gln Arg
    1055               1060

<210> SEQ ID NO 5
<211> LENGTH: 2373
<212> TYPE: DNA
<213> ORGANISM: Ehrlichia canis

<400> SEQUENCE: 5
aattatgctg aaactacttt atcatttggt gaatctcgag cagaaggacg tgaatctcca      60
tcaagtgcat tgttcaaac tggtcaatca gaagtacctc ggagtgaggc tgcagagcca     120
ttaattcaat ttcctcatga tgaagaaagt actgcattag gttctcaagc aactatgaca     180
ggagtgtcta ctcaggctag tccgtcagca gcatatcagg atgatagtga aatatcacgt     240
atgaggtcta tggcaggaac atctgctcaa gctgatcaat cagcagtaca tcgtcggagt     300
ggtacagcat tagagccatt aattgaattg cctgatgaag aagaaaatgc tgcattagat     360
tttcaaacag ctatgacagg agtgcctact caggctagtc cgtcagcagt acatcggagt     420
ggtgttgcat cagatcctac gctacctgat gatgaaagaa ttgatgttcc atcagtttca     480
tctcaagttg taagaccttt tagtgatggt gaagattatt cagtatatga taaatcaggt     540
gtagtaagtg gtcatgaaag acctgtttct tctagagatt caagacaatt ggatgcattt     600
ggtgatccat cagatgattt attgccggag agtgaaatta ttgttagcag cagtaagaaa     660
gcaatattag atagccaaaa tgaaatagaa tctcttattc agagtggaga tacttctaga     720
tgtattaggg caattaatag tgctcctagt gcgtcagtgt ttcaactgaa gactttatcg     780
aatgatatat ctattgctgg acgtgctttt ttaaatggta atattgattt aatagaagct     840
tgtatgaatt ctggcaagaa attaaatcca aatattactg ataatgaaaa aaatactcta     900
ttacatcaat ttgtaggata ttttgaacgc gatccgagaa tgttgcttga tgcaggaatg     960
cgtaatctgt ttttgagatt atgcatggat tatggtttcg atattaatca taaaaatagt    1020
aatggtaata cagtacttga tagattaaat gatttagtag aagggttaag tagttcgcaa    1080
gttgatcttg aaagtagtgg tattgatgag tttatgatct cattgttagc tcattctaga    1140
atgagtgatc aagcagtaaa gaatattgct actgcgcaaa tgagtttttt tgcacgtgat    1200 tctgttttata atattagtcg tttagttgat acttctatag ttttgcagaa taaattcagt    1260
gaagtatttt atgaagtctg tggacgtatt ttatctgaag aagctggtaa acataagggt    1320
gttgctgaag caaattattc aagattgaat aaaatattaa atgatgaatg tcttagaaag    1380
actttagcta atacagatgc cgatggaaat aatgttttac agagattgtg tcaagatatt    1440
gcttctggaa aaatcaatgc tcgtgatgac agagtattaa aactttttga dacaattata    1500
tctaatttaa aagacaaaga taagcatta ctagaggatt tattatttaa aatagaaac     1560 tcaagatttg aaaattgcat tgaagctata ccacgtattc ctggtgccga tgctctattt    1620
aaaaaactag aagagttatt attaaaaaag aaaatagcag agtcttgtga ttttaattct    1680
```

-continued

```
atgttagtga attgtgctga gtctgctaat gataatttat ataattaccct gcgcactaat    1740
tatgcagtta ttggtataaa taacgtagat ataaatggca attcatccct atgtaaagct    1800
gttgttactg ggtcacaagg tattgttaaa gcagtattat caactggaac taatattaat    1860
aggaaagata aaaatggtaa tacacctta catgcattgt taattttat gatgtctaac     1920
cctgaacttg tcaaggagca acatatttca cttgtgaaat tcttagcgtc tcgtggagct    1980
ttacttaatg taaaaaataa tatgaatatt tctccaatta tgcttgcaga atctattgat    2040
aagaaagagg aacttgctaa gaaatttaca aatcaaaaag ttagtatttt agaatcttta    2100
atagctggta gtgaagaaca tttagggctt aaatccaaat gtatatctga gttaaagcct    2160
tatatagaat taggaaaagg catgaagtac gaagatatac atgctgatgt aataggtggt    2220
gtattatctg ctgatatgtg taatgctaga ttgcagatag gtaaattatt aaatggtgat    2280
ttttgtaaag aaaatgaatt aaagacagta aaatttaatt tttctgatac aaataagggt    2340
tatgtacaaa atgttggtaa aaaaagaaat tat                                 2373
```

<210> SEQ ID NO 6
<211> LENGTH: 791
<212> TYPE: PRT
<213> ORGANISM: Ehrlichia canis

<400> SEQUENCE: 6

```
Asn Tyr Ala Glu Thr Thr Leu Ser Phe Gly Glu Ser Arg Ala Glu Gly
1               5                   10                  15

Arg Glu Ser Pro Ser Ser Ala Phe Val Gln Thr Gly Gln Ser Glu Val
            20                  25                  30

Pro Arg Ser Glu Ala Ala Glu Pro Leu Ile Gln Phe Pro His Asp Glu
        35                  40                  45

Glu Ser Thr Ala Leu Gly Ser Gln Ala Thr Met Thr Gly Val Ser Thr
    50                  55                  60

Gln Ala Ser Pro Ser Ala Ala Tyr Gln Asp Asp Ser Glu Ile Ser Arg
65                  70                  75                  80

Met Arg Ser Met Ala Gly Thr Ser Ala Gln Ala Asp Gln Ser Ala Val
                85                  90                  95

His Arg Arg Ser Gly Thr Ala Leu Glu Pro Leu Ile Glu Leu Pro Asp
            100                 105                 110

Glu Glu Glu Asn Ala Ala Leu Asp Phe Gln Thr Ala Met Thr Gly Val
        115                 120                 125

Pro Thr Gln Ala Ser Pro Ser Ala Val His Arg Ser Gly Val Ala Ser
    130                 135                 140

Asp Pro Thr Leu Pro Asp Asp Glu Arg Ile Asp Val Pro Ser Val Ser
145                 150                 155                 160

Ser Gln Val Val Arg Pro Phe Ser Asp Gly Glu Asp Tyr Ser Val Tyr
                165                 170                 175

Asp Lys Ser Gly Val Val Ser Gly His Glu Arg Pro Val Ser Ser Arg
            180                 185                 190

Asp Ser Arg Gln Leu Asp Ala Phe Gly Asp Pro Ser Asp Asp Leu Leu
        195                 200                 205

Pro Glu Ser Glu Ile Ile Val Ser Ser Lys Lys Ala Ile Leu Asp
    210                 215                 220

Ser Gln Asn Glu Ile Glu Ser Leu Ile Gln Ser Gly Asp Thr Ser Arg
225                 230                 235                 240

Cys Ile Arg Ala Ile Asn Ser Ala Pro Ser Ala Ser Val Phe Gln Leu
                245                 250                 255
```

```
Lys Thr Leu Ser Asn Asp Ile Ser Ile Ala Gly Arg Ala Phe Leu Asn
            260                 265                 270

Gly Asn Ile Asp Leu Ile Glu Ala Cys Met Asn Ser Gly Lys Lys Leu
        275                 280                 285

Asn Pro Asn Ile Thr Asp Asn Glu Lys Asn Thr Leu Leu His Gln Phe
    290                 295                 300

Val Gly Tyr Phe Glu Arg Asp Pro Arg Met Leu Leu Asp Ala Gly Met
305                 310                 315                 320

Arg Asn Leu Phe Leu Arg Leu Cys Met Asp Tyr Gly Phe Asp Ile Asn
                325                 330                 335

His Lys Asn Ser Asn Gly Asn Thr Val Leu Asp Arg Leu Asn Asp Leu
            340                 345                 350

Val Glu Gly Leu Ser Ser Ser Gln Val Asp Leu Glu Ser Ser Gly Ile
        355                 360                 365

Asp Glu Phe Met Ile Ser Leu Leu Ala His Ser Arg Met Ser Asp Gln
    370                 375                 380

Ala Val Lys Asn Ile Ala Thr Ala Gln Asn Glu Phe Phe Ala Arg Asp
385                 390                 395                 400

Ser Val Tyr Asn Ile Ser Arg Leu Val Asp Thr Ser Ile Val Leu Gln
                405                 410                 415

Asn Lys Phe Ser Glu Val Phe Tyr Glu Val Cys Gly Arg Ile Leu Ser
            420                 425                 430

Glu Glu Ala Gly Lys His Lys Gly Val Ala Glu Ala Asn Tyr Ser Arg
        435                 440                 445

Leu Asn Lys Ile Leu Asn Asp Glu Cys Leu Arg Lys Thr Leu Ala Asn
    450                 455                 460

Thr Asp Ala Asp Gly Asn Asn Val Leu Gln Arg Leu Cys Gln Asp Ile
465                 470                 475                 480

Ala Ser Gly Lys Ile Asn Ala Arg Asp Asp Arg Val Leu Lys Leu Phe
                485                 490                 495

Glu Thr Ile Ile Ser Asn Leu Lys Asp Lys Asp Lys Ala Leu Leu Glu
            500                 505                 510

Asp Leu Leu Phe Asn Asn Arg Asn Ser Arg Phe Glu Asn Cys Ile Glu
        515                 520                 525

Ala Ile Pro Arg Ile Pro Gly Ala Asp Ala Leu Phe Lys Lys Leu Glu
    530                 535                 540

Glu Leu Leu Leu Lys Lys Lys Ile Ala Glu Ser Cys Asp Phe Asn Ser
545                 550                 555                 560

Met Leu Val Asn Cys Ala Glu Ser Ala Asn Asp Asn Leu Tyr Asn Tyr
                565                 570                 575

Leu Arg Thr Asn Tyr Ala Val Ile Gly Ile Asn Asn Val Asp Ile Asn
            580                 585                 590

Gly Asn Ser Ser Leu Cys Lys Ala Val Val Thr Gly Ser Gln Gly Ile
        595                 600                 605

Val Lys Ala Val Leu Ser Thr Gly Thr Asn Ile Asn Arg Lys Asp Lys
    610                 615                 620

Asn Gly Asn Thr Pro Leu His Ala Leu Leu Ile Phe Met Met Ser Asn
625                 630                 635                 640

Pro Glu Leu Val Lys Glu Gln His Ile Ser Leu Val Lys Phe Leu Ala
                645                 650                 655

Ser Arg Gly Ala Leu Leu Asn Val Lys Asn Asn Met Asn Ile Ser Pro
            660                 665                 670
```

```
Ile Met Leu Ala Glu Ser Ile Asp Lys Lys Glu Leu Ala Lys Lys
            675                 680                 685

Phe Thr Asn Gln Lys Val Ser Ile Leu Glu Ser Leu Ile Ala Gly Ser
            690                 695                 700

Glu Glu His Leu Gly Leu Lys Ser Lys Cys Ile Ser Glu Leu Lys Pro
705                 710                 715                 720

Tyr Ile Glu Leu Gly Lys Gly Met Lys Tyr Glu Asp Ile His Ala Asp
                725                 730                 735

Val Ile Gly Gly Val Leu Ser Ala Asp Met Cys Asn Ala Arg Leu Gln
                740                 745                 750

Ile Gly Lys Leu Leu Asn Gly Asp Phe Cys Lys Glu Asn Glu Leu Lys
            755                 760                 765

Thr Val Lys Phe Asn Phe Ser Asp Thr Asn Lys Gly Tyr Val Gln Asn
770                 775                 780

Val Gly Lys Lys Arg Asn Tyr
785                 790

<210> SEQ ID NO 7
<211> LENGTH: 2283
<212> TYPE: DNA
<213> ORGANISM: Ehrlichia canis

<400> SEQUENCE: 7
gtaaaaaaat taagattatt attaaattca ataagtgagt taccgcaaga attaaaagat      60
caaattttaa gtactagaag tactatagat aaattacgaa atagaattaa tgcctgcata     120
aagtctgacg atagagaagg tattgcacat gctgtagaat ctatggctag ttcttattgt     180
gaattattag acattgtag  attaatttt  aagaaattat atgatgaaaa tgctgataaa     240
agtttgctag aattatgtat taagaatat  caatctgatt taaacaaatt attggaacaa     300
ggtattgata tatgtgcttc agaagtctca tcagaatgta aggatttagt ttgtaaagta     360
tgtgaagatg aatttgagaa atatgactct ttatctaaag tacaaagatt cagggaatta     420
tctggtgaaa ttgctgattt ggatgataaa ttaacaagaa gggcttcttt tgttgagact     480
tttggattat ttagcagtag attaagacat tatagggaaa ttttaggaga tggtgattta     540
aaatttcgag agaggatagt tgaaaaatat caagaggatt taaggaatt  attagaatta     600 tctgttgatc ttcatttgtt aataaattta ccagcattag aagatttacg cgatcataga     660
aatttagtgc atagagcatg taatgctgaa attgaaaaat atctaacttt atttgatgat     720
caacaattac gtacattatc gcaagaagtg aataatgctc atggtgaatt gatacagatg     780
ttttctaagt ttagtatatt tgttgatggc gttactggta ttgaacagag cacatctcaa     840
gtagagcacc ctcgttctga tattgctaaa agagatacta caacaccaaa gcaacgtgtt     900
gtgcaaggta aagatgatat acaatctagt gatagtgata gtgatagtga tagtaaatac     960
ggtgatgatg atagtaaaaa agcatcagtt agtgcacctg ctgttgacca agttgtacct    1020
gtagctgatg ttcaacctga acctcagcta ggtgaaggat tggaaacatt agagtctagt    1080
atagctgaag gacctgagtt gcctggtgat gcatctactg ctaagcaatc tatacctttt    1140
gcgataacac catcaagtcc tgagacagtt gatgaaaaac ttgaaagttc tggtgttagt    1200
caagatggta ttacaacacc aggacaacgt gttgtgcaag gtaagatgga tatacaatct    1260
agtgatagtg atagtgatag taaatacggt gatgatgata gtaaaaaagc atcagctagt    1320
gcacctgctg ttgaccaagt tgtacctgta gctgatgttc aacctgaacc tcagctaggt    1380
gaaaaattgg aaacattaga gtctagtata actaaaggac ctgagttgcc tggtgatgca    1440
```

-continued

```
tctactgcta agcaatctat accttttgcg ataacaccat caagtcctga gacagttgat      1500
gaaaaacttg aaagttctgg tgttagtcaa gatggtatta caacaccagg caacgtgtt      1560 gtgcaaggta agatgatat acaatctagt gatagtgata gtgatagtaa atacggtgat       1620
gatgatagta aaaaagcatc agctagtgca cctgctgttg accaagttgt accttctgac      1680
actcgtgcag atggagtatc agaaccatta gcatctcatg tggatcaagg atctgatgta      1740
cctggtgatg catctgttga tggtgttgat ttaagattag gacggttatc tactgagcaa      1800
agtggattgt tgccacgtca tgaacaaaat gtaagagcat ttattttaga acagagtttg      1860
ttagatcaat tatatatgga ctatatagat ttacaccctg atcagaaaag ttgtgaagct      1920
tataattcag cattgcatgg atataataca agattagagt tacagaagga atataacagg      1980
atttttgaat cacatgaatc agcatctcca aatgaaatta atagtttttc acaaaaatat      2040
agagcagcat taagagatgt tgcgcaggat attgttaatc agggtccaat gttttattct      2100
tctagagatg caatgctatt aagggctaga gtagacacat tgtgtgatat gtgtcgttca      2160
atacgtaatc tgtatatggt tgaattagat gccatagata aagaagaaaa atcgttacaa      2220
tctgatatga aatctgcaag ttctagtgat aaaaagttga tacaagaaaa aataaaatta      2280
ctt                                                                    2283
```

<210> SEQ ID NO 8
<211> LENGTH: 761
<212> TYPE: PRT
<213> ORGANISM: Ehrlichia canis

<400> SEQUENCE: 8

```
Val Lys Lys Leu Arg Leu Leu Asn Ser Ile Ser Glu Leu Pro Gln
 1               5                  10                  15

Glu Leu Lys Asp Gln Ile Leu Ser Thr Arg Ser Thr Ile Asp Lys Leu
            20                  25                  30

Arg Asn Arg Ile Asn Ala Cys Ile Lys Ser Asp Asp Arg Glu Gly Ile
        35                  40                  45

Ala His Ala Val Glu Ser Met Ala Ser Ser Tyr Cys Glu Leu Leu Gly
    50                  55                  60

His Cys Arg Leu Ile Phe Lys Lys Leu Tyr Asp Glu Asn Ala Asp Lys
65                  70                  75                  80

Ser Leu Leu Glu Leu Cys Ile Lys Glu Tyr Gln Ser Asp Leu Asn Lys
                85                  90                  95

Leu Leu Glu Gln Gly Ile Asp Ile Cys Ala Ser Glu Val Ser Ser Glu
            100                 105                 110

Cys Lys Asp Leu Val Cys Lys Val Cys Glu Asp Glu Phe Glu Lys Tyr
        115                 120                 125

Asp Ser Leu Ser Lys Val Gln Arg Phe Arg Glu Leu Ser Gly Glu Ile
    130                 135                 140

Ala Asp Leu Asp Asp Lys Leu Thr Arg Arg Ala Ser Phe Val Glu Thr
145                 150                 155                 160

Phe Gly Leu Phe Ser Ser Arg Leu Arg His Tyr Arg Glu Ile Leu Gly
                165                 170                 175

Asp Gly Asp Leu Lys Phe Arg Glu Arg Ile Val Glu Lys Tyr Gln Glu
            180                 185                 190

Asp Leu Lys Glu Leu Leu Glu Leu Ser Val Asp Leu His Leu Leu Ile
        195                 200                 205

Asn Leu Pro Ala Leu Glu Asp Leu Arg Asp His Arg Asn Leu Val His
```

-continued

```
            210                 215                 220
Arg Ala Cys Asn Ala Glu Ile Glu Lys Tyr Leu Thr Leu Phe Asp Asp
225                 230                 235                 240

Gln Gln Leu Arg Thr Leu Ser Gln Val Asn Asn Ala His Gly Glu
            245                 250                 255

Leu Ile Gln Met Phe Ser Lys Phe Ser Ile Phe Val Asp Gly Val Thr
            260                 265                 270

Gly Ile Glu Gln Ser Thr Ser Gln Val Glu His Pro Arg Ser Asp Ile
            275                 280                 285

Ala Lys Arg Asp Thr Thr Thr Pro Lys Gln Arg Val Val Gln Gly Lys
290                 295                 300

Asp Asp Ile Gln Ser Ser Asp Ser Asp Ser Asp Ser Asp Ser Lys Tyr
305                 310                 315                 320

Gly Asp Asp Asp Ser Lys Lys Ala Ser Val Ser Ala Pro Ala Val Asp
            325                 330                 335

Gln Val Val Pro Val Ala Asp Val Gln Pro Glu Pro Gln Leu Gly Glu
            340                 345                 350

Gly Leu Glu Thr Leu Glu Ser Ser Ile Ala Glu Gly Pro Glu Leu Pro
            355                 360                 365

Gly Asp Ala Ser Thr Ala Lys Gln Ser Ile Pro Phe Ala Ile Thr Pro
370                 375                 380

Ser Ser Pro Glu Thr Val Asp Glu Lys Leu Glu Ser Ser Gly Val Ser
385                 390                 395                 400

Gln Asp Gly Ile Thr Thr Pro Gly Gln Arg Val Val Gln Gly Lys Asp
            405                 410                 415

Asp Ile Gln Ser Ser Asp Ser Asp Ser Asp Ser Lys Tyr Gly Asp Asp
            420                 425                 430

Asp Ser Lys Lys Ala Ser Ala Ser Ala Pro Ala Val Asp Gln Val Val
            435                 440                 445

Pro Val Ala Asp Val Gln Pro Glu Pro Gln Leu Gly Glu Lys Leu Glu
450                 455                 460

Thr Leu Glu Ser Ser Ile Thr Lys Gly Pro Glu Leu Pro Gly Asp Ala
465                 470                 475                 480

Ser Thr Ala Lys Gln Ser Ile Pro Phe Ala Ile Thr Pro Ser Ser Pro
            485                 490                 495

Glu Thr Val Asp Glu Lys Leu Glu Ser Ser Gly Val Ser Gln Asp Gly
            500                 505                 510

Ile Thr Thr Pro Gly Gln Arg Val Val Gln Gly Lys Asp Asp Ile Gln
            515                 520                 525

Ser Ser Asp Ser Asp Ser Asp Ser Lys Tyr Gly Asp Asp Asp Ser Lys
530                 535                 540

Lys Ala Ser Ala Ser Ala Pro Ala Val Asp Gln Val Val Pro Ser Asp
545                 550                 555                 560

Thr Arg Ala Asp Gly Val Ser Glu Pro Leu Ala Ser His Val Asp Gln
            565                 570                 575

Gly Ser Asp Val Pro Gly Asp Ala Ser Val Asp Gly Val Asp Leu Arg
            580                 585                 590

Leu Gly Arg Leu Ser Thr Glu Gln Ser Gly Leu Leu Pro Arg His Glu
            595                 600                 605

Gln Asn Val Arg Ala Phe Ile Leu Glu Gln Ser Leu Leu Asp Gln Leu
            610                 615                 620

Tyr Met Asp Tyr Ile Asp Leu His Pro Asp Gln Lys Ser Cys Glu Ala
625                 630                 635                 640
```

-continued

```
Tyr Asn Ser Ala Leu His Gly Tyr Asn Thr Arg Leu Glu Leu Gln Lys
                645                 650                 655

Glu Tyr Asn Arg Ile Phe Glu Ser His Glu Ser Ala Ser Pro Asn Glu
            660                 665                 670

Ile Asn Ser Phe Ser Gln Lys Tyr Arg Ala Ala Leu Arg Asp Val Ala
        675                 680                 685

Gln Asp Ile Val Asn Gln Gly Pro Met Phe Tyr Ser Ser Arg Asp Ala
    690                 695                 700

Met Leu Leu Arg Ala Arg Val Asp Thr Leu Cys Asp Met Cys Arg Ser
705                 710                 715                 720

Ile Arg Asn Leu Tyr Met Val Glu Leu Asp Ala Ile Asp Lys Glu Glu
                725                 730                 735

Lys Ser Leu Gln Ser Asp Met Lys Ser Ala Ser Ser Ser Asp Lys Lys
            740                 745                 750

Leu Ile Gln Glu Lys Ile Lys Leu Leu
        755                 760

<210> SEQ ID NO 9
<211> LENGTH: 414
<212> TYPE: PRT
<213> ORGANISM: Ehrlichia canis

<400> SEQUENCE: 9

Ala Thr Gly Thr Thr Ala Cys Ala Cys Gly Thr Thr Cys Ala Ala Ala
1               5                   10                  15

Ala Thr Cys Ala Thr Gly Thr Thr Gly Ala Thr Cys Ala Ala Cys Ala
            20                  25                  30

Thr Ala Cys Ala Ala Ala Thr Cys Ala Thr Ala Thr Ala Gly Ala Ala
        35                  40                  45

Cys Ala Thr Gly Ala Thr Gly Ala Thr Thr Ala Cys Cys Ala Thr Thr
    50                  55                  60

Thr Thr Ala Cys Thr Gly Gly Thr Cys Cys Thr Ala Cys Thr Ala Gly
65                  70                  75                  80

Thr Thr Thr Thr Gly Ala Ala Gly Thr Thr Ala Ala Thr Cys Thr Thr
                85                  90                  95

Thr Cys Thr Gly Ala Ala Gly Ala Ala Gly Ala Ala Ala Ala Ala Ala
            100                 105                 110

Thr Gly Gly Ala Gly Thr Thr Ala Cys Ala Ala Gly Ala Ala Gly Thr
        115                 120                 125

Ala Thr Cys Thr Thr Cys Thr Ala Thr Thr Gly Ala Thr Ala Gly Thr
    130                 135                 140

Gly Thr Ala Gly Gly Ala Thr Gly Cys Gly Ala Ala Gly Ala Thr Thr
145                 150                 155                 160

Gly Thr Gly Ala Thr Cys Cys Ala Ala Ala Thr Thr Gly Thr Cys Gly
                165                 170                 175

Thr Thr Ala Thr Cys Cys Thr Thr Thr Ala Gly Ala Ala Thr Thr Ala
            180                 185                 190

Gly Thr Ala Gly Ala Ala Thr Gly Thr Cys Ala Gly Cys Gly Thr Ala
        195                 200                 205

Thr Thr Gly Ala Gly Gly Ala Ala Ala Gly Ala Cys Cys Ala Gly Thr
    210                 215                 220

Ala Thr Gly Cys Ala Ala Thr Gly Cys Ala Gly Gly Thr Thr Thr Ala
225                 230                 235                 240

Gly Ala Gly Ala Gly Cys Thr Thr Gly Ala Cys Thr Gly Thr Thr Gly
```

-continued 245 250 255

Ala Thr Gly Cys Ala Thr Ala Thr Cys Ala Ala Thr Thr Ala Gly Gly
260 265 270

Ala Thr Thr Gly Thr Thr Gly Thr Thr Ala Gly Gly Thr Gly Gly Thr
275 280 285

Thr Thr Thr Thr Thr Ala Ala Gly Thr Gly Cys Thr Ala Thr Gly Ala
290 295 300

Ala Thr Thr Ala Cys Ala Thr Ala Thr Cys Thr Thr Ala Thr Ala Gly
305 310 315 320

Cys Thr Ala Thr Cys Cys Thr Thr Gly Thr Thr Ala Thr Thr Ala Thr
325 330 335

Thr Ala Thr Gly Ala Thr Thr Gly Thr Thr Gly Thr Gly Ala Thr Ala
340 345 350

Gly Ala Ala Ala Thr Thr Ala Thr Thr Ala Cys Gly Ala Cys Thr Gly
355 360 365

Thr Thr Gly Thr Cys Ala Thr Ala Ala Gly Ala Ala Thr Gly Cys Gly
370 375 380

Thr Gly Thr Thr Ala Thr Thr Ala Cys Ala Ala Cys Thr Gly Thr Thr
385 390 395 400

Gly Thr Gly Ala Thr Thr Gly Thr Gly Cys Gly Thr Ala Ala
405 410

<210> SEQ ID NO 10
<211> LENGTH: 137
<212> TYPE: PRT
<213> ORGANISM: Ehrlichia canis

<400> SEQUENCE: 10

Met Leu His Val Gln Asn His Val Asp Gln His Thr Asn His Ile Glu
1 5 10 15

His Asp Asp Tyr His Phe Thr Gly Pro Thr Ser Phe Glu Val Asn Leu
20 25 30

Ser Glu Glu Glu Lys Met Glu Leu Gln Glu Val Ser Ser Ile Asp Ser
35 40 45

Val Gly Cys Glu Asp Cys Asp Pro Asn Cys Arg Tyr Pro Leu Glu Leu
50 55 60

Val Glu Cys Gln Arg Ile Glu Glu Arg Pro Val Cys Asn Ala Gly Leu
65 70 75 80

Glu Ser Leu Thr Val Asp Ala Tyr Gln Leu Gly Leu Leu Leu Gly Gly
85 90 95

Phe Leu Ser Ala Met Asn Tyr Ile Ser Tyr Ser Tyr Pro Cys Tyr Tyr
100 105 110

Tyr Asp Cys Cys Asp Arg Asn Tyr Tyr Asp Cys Cys His Lys Asn Ala
115 120 125

Cys Tyr Tyr Asn Cys Cys Asp Cys Ala
130 135

<210> SEQ ID NO 11
<211> LENGTH: 3018
<212> TYPE: DNA
<213> ORGANISM: Ehrlichia canis

<400> SEQUENCE: 11
atgacgattt tcttagaaag tgatgatgat aagagtaact ttaagaagac attggagaac 60
ggtactaaag acaagacaaa tctagataat acttattatg actatcatca tgaagatgat 120

-continued

```
atgggaaata ctgaatatca ttatgtgagt ttggatagag tggatcatgt taagatgcct    180
gaagagcctg taggttatgg tggagatact ttacctattg ttcctactac agctgctagt    240
gtatctggta gtgatgcagg cgttgctgta ggtaatgtta agattttga agataatgtt    300
tttcatcata catctactat aagaaacgat gaattgaaga tagatttacg aatacatact    360
ttaaaggatt tatctgataa agattacgt gaaattgaaa agggatttaa tgatacggta    420
acaaaattta aaataatttt tgggttagaa ccaaatgatg agaaactat ttttgattta    480
taccttttg atgataagga acaatataat tattatggaa agctttataa cttaggaatt    540
agtggatctg gaggtatgac tttctatgga atgctaatg ttccatataa aatttatgta    600
catcaatatg gtgaaatatt gaatttaaaa catgaattaa ctcatgcatt agaaagttat    660
gcatctggac ataaattgca tggttctgac gtaaatagca gaatatttac ggaaggatta    720
gctgattata tccaagaaga taatagtttt attatgagag gattaaagga tcgagagatc    780
acttcagatg tattgaaaga ttcttctggt aatgtagatc atttaagtgg tgttgcagtg    840
aatgaaaatc agaggttaag ttatagtata ggacatgcat ttgtaagctt tttacaagag    900
aaatatccta agttaatttc ggaatatta aacgcattaa aagaggataa tattattcgt    960
gctaaagaaa taattagtat ggataagtat ccagattttg agccgtgggt gaagtctaaa   1020
gacattagtt tatatttaga aaatatgaat gtattaaagt taggattagg tgagaaaatg   1080
ttttctgctg aaagtgctag ctattttgaa gatcaaggtg tcaataaaga atattaccat   1140
gaaaatattt atgatatgag tggtaaacta gtaggtgaaa tgtcacctgt agtgcattat   1200
gcacaaaaaa atgtgattcg tatttggaat attgcaagtc ctgatatgat agaggtgcga   1260
ccagaatata acttttctgaa attggtaact actccatctg gtaagtctgc atatgtatat   1320
tgtgataaga atgggcatga gtattttaat actaaagatt acatagattc tgcgtttaat   1380
atattggcaa gatatgatgt taagcttcgt gaaagtagtg atgctttgga tattagaggt   1440
cgttactcag atgctgctaa agtgtttagt aagctgccta atgcggattt gctgttggat   1500
aagttttag aaaaaatagg ttatagtagt tataagcaga taataatgag taatccagaa   1560
cagcttaatt ctattaaggc ttatgtagta aaagaagtgt ttgaaaattt tagggaatct   1620
gaggtcaaaa aggtgttgag tggtgagtct catccggaag taagaaatgt attaatggat   1680
cttacctatg ttgatttaaa gagtgttata ggagtaaatg gtgcagatat tgacagtatt   1740
atttctaatc cagatgtaat gttgcgtact gctgtgttag gtaaaggaaa tgcaagtggg   1800
atatctctat atgtagatga tcagaaagtt ggtgagctgt caactgaagc aggttattgt   1860
gttaaaaatc ttgatactgg taaagtgtat tttatgttcc ataatgttgt tggaatgata   1920
gcaagtggtt atgaagacag agcatatatg gttgtattag aaaaagatgg taagtttact   1980
actgctctag ttaataatat acaaaaagca gcagatggaa atgttgtatg ggataatcaa   2040
tttaatcatc cgaatattaa taacttgcac tcaaattata aggagctgtt gttaaatgat   2100
gcttcagtta aagattactc tcatcttgcg gatgtgaaat ttaataaaga tgatacagta   2160
attgttaaag gtgaattatt agatgataaa ggtactgtaa gtgtagatga tgatgtacat   2220
cgtgcagttg ttaagcatga tgatcaaata ctacatcagt ttaagagtat gtcttttttac   2280
attactgaac catcagctga ttcaggtgac aattatggaa gtgatttttt catttctgat   2340
gaaggaaaaa atcttagatt tcaacttcct aaagctatta cgcatttgaa attggttaat   2400
gttaatggaa ataataagtt ggtaccatgt actaaagatg ggaatgaaca tcctgaaggt   2460
atgccatctg atttaacgga tgaatataga tatatagatc ctattttgc tcatacattt   2520
```

-continued

```
gagaaacaaa gttattctaa aaatagtatt agtgttgggt tagtggactt cagtaaatat    2580
aaagaaggat ctatgtttaa attacagcat tattctgatg attatcatat tcataaggat    2640
gaacaaggta atgttattag gcctaataac agatcttacg ttacaaaagt ggatttagta    2700
tatgatgata aagttattgg gatgttgtct gatagtataa atcaatttca gggtgatatt    2760
ttcatttctg caagccttaa ttatagccac aatgattttc tttcatctaa gtactttcag    2820
aaagttaata ttgaggcgtt agaaaatgga atatatagtg aagatatga tgtaggagat     2880 ggtgaccaaa tagcaggtct taatactgat acaggttata gtgataaagc tattttttac    2940
tttaaaaatg atagcgcatc tactgatatg ccggctagtg atgttactac tattttacct    3000
tatataaatg agctttaa                                                  3018
```

<210> SEQ ID NO 12
<211> LENGTH: 1005
<212> TYPE: PRT
<213> ORGANISM: Ehrlichia canis

<400> SEQUENCE: 12

```
Met Thr Ile Phe Leu Glu Ser Asp Asp Lys Ser Asn Phe Lys Lys
1               5                   10                  15

Thr Leu Glu Asn Gly Thr Lys Asp Lys Thr Asn Leu Asp Asn Thr Tyr
                20                  25                  30

Tyr Asp Tyr His His Glu Asp Asp Met Gly Asn Thr Glu Tyr His Tyr
            35                  40                  45

Val Ser Leu Asp Arg Val Asp His Val Lys Met Pro Glu Glu Pro Val
        50                  55                  60

Gly Tyr Gly Gly Asp Thr Leu Pro Ile Val Pro Thr Thr Ala Ala Ser
65                  70                  75                  80

Val Ser Gly Ser Asp Ala Gly Val Ala Val Gly Asn Val Lys Asp Phe
                85                  90                  95

Glu Asp Asn Val Phe His His Thr Ser Thr Ile Arg Asn Asp Glu Leu
            100                 105                 110

Lys Ile Asp Leu Arg Ile His Thr Leu Lys Asp Leu Ser Asp Lys Arg
        115                 120                 125

Leu Arg Glu Ile Glu Lys Gly Phe Asn Asp Thr Val Thr Lys Phe Lys
    130                 135                 140

Asn Asn Phe Gly Leu Glu Pro Asn Asp Gly Glu Thr Ile Phe Asp Leu
145                 150                 155                 160

Tyr Leu Phe Asp Asp Lys Glu Gln Tyr Asn Tyr Tyr Gly Lys Leu Tyr
                165                 170                 175

Asn Leu Gly Ile Ser Gly Ser Gly Gly Met Thr Phe Tyr Gly Asn Ala
            180                 185                 190

Asn Val Pro Tyr Lys Ile Tyr Val His Gln Tyr Gly Glu Ile Leu Asn
        195                 200                 205

Leu Lys His Glu Leu Thr His Ala Leu Glu Ser Tyr Ala Ser Gly His
    210                 215                 220

Lys Leu His Gly Ser Asp Val Asn Ser Arg Ile Phe Thr Glu Gly Leu
225                 230                 235                 240

Ala Asp Tyr Ile Gln Glu Asp Asn Ser Phe Ile Met Arg Gly Leu Lys
                245                 250                 255

Asp Arg Glu Ile Thr Ser Asp Val Leu Lys Asp Ser Ser Gly Asn Val
            260                 265                 270

Asp His Leu Ser Gly Val Ala Val Asn Glu Asn Gln Arg Leu Ser Tyr
```

```
                275                 280                 285
Ser Ile Gly His Ala Phe Val Ser Phe Leu Gln Glu Lys Tyr Pro Lys
290                 295                 300

Leu Ile Ser Glu Tyr Leu Asn Ala Leu Lys Glu Asp Asn Ile Ile Arg
305                 310                 315                 320

Ala Lys Glu Ile Ile Ser Met Asp Lys Tyr Pro Asp Phe Glu Pro Trp
                325                 330                 335

Val Lys Ser Lys Asp Ile Ser Leu Tyr Leu Glu Asn Met Asn Val Leu
                340                 345                 350

Lys Leu Gly Leu Gly Glu Lys Met Phe Ser Ala Glu Ser Ala Ser Tyr
                355                 360                 365

Phe Glu Asp Gln Gly Val Asn Lys Glu Tyr Tyr His Glu Asn Ile Tyr
370                 375                 380

Asp Met Ser Gly Lys Leu Val Gly Glu Met Ser Pro Val Val His Tyr
385                 390                 395                 400

Ala Gln Lys Asn Val Ile Arg Ile Trp Asn Ile Ala Ser Pro Asp Met
                405                 410                 415

Ile Glu Val Arg Pro Glu Tyr Asn Phe Leu Lys Leu Val Thr Thr Pro
                420                 425                 430

Ser Gly Lys Ser Ala Tyr Val Tyr Cys Asp Lys Asn Gly His Glu Tyr
                435                 440                 445

Phe Asn Thr Lys Asp Tyr Ile Asp Ser Ala Phe Asn Ile Leu Ala Arg
450                 455                 460

Tyr Asp Val Lys Leu Arg Glu Ser Ser Asp Ala Leu Asp Ile Arg Gly
465                 470                 475                 480

Arg Tyr Ser Asp Ala Ala Lys Val Phe Ser Lys Leu Pro Asn Ala Asp
                485                 490                 495

Leu Leu Leu Asp Lys Phe Leu Glu Lys Ile Gly Tyr Ser Ser Tyr Lys
                500                 505                 510

Gln Ile Ile Met Ser Asn Pro Glu Gln Leu Asn Ser Ile Lys Ala Tyr
                515                 520                 525

Val Val Lys Glu Val Phe Glu Asn Phe Arg Glu Ser Glu Val Lys Lys
530                 535                 540

Val Leu Ser Gly Glu Ser His Pro Glu Val Arg Asn Val Leu Met Asp
545                 550                 555                 560

Leu Thr Tyr Val Asp Leu Lys Ser Val Ile Gly Val Asn Gly Ala Asp
                565                 570                 575

Ile Asp Ser Ile Ile Ser Asn Pro Asp Val Met Leu Arg Thr Ala Val
                580                 585                 590

Leu Gly Lys Gly Asn Ala Ser Gly Ile Ser Leu Tyr Val Asp Asp Gln
                595                 600                 605

Lys Val Gly Glu Leu Ser Thr Glu Ala Gly Tyr Cys Val Lys Asn Leu
                610                 615                 620

Asp Thr Gly Lys Val Tyr Phe Met Phe His Asn Val Val Gly Met Ile
625                 630                 635                 640

Ala Ser Gly Tyr Glu Asp Arg Ala Tyr Met Val Val Leu Glu Lys Asp
                645                 650                 655

Gly Lys Phe Thr Thr Ala Leu Val Asn Asn Ile Gln Lys Ala Ala Asp
                660                 665                 670

Gly Asn Val Val Trp Asp Asn Gln Phe Asn His Pro Asn Ile Asn Asn
                675                 680                 685

Leu His Ser Asn Tyr Lys Glu Leu Leu Leu Asn Asp Ala Ser Val Lys
                690                 695                 700
```

-continued

```
Asp Tyr Ser His Leu Ala Asp Val Lys Phe Asn Lys Asp Asp Thr Val
705                 710                 715                 720

Ile Val Lys Gly Glu Leu Leu Asp Asp Lys Gly Thr Val Ser Val Asp
                725                 730                 735

Asp Asp Val His Arg Ala Val Val Lys His Asp Asp Gln Ile Leu His
            740                 745                 750

Gln Phe Lys Ser Met Ser Phe Tyr Ile Thr Glu Pro Ser Ala Asp Ser
        755                 760                 765

Gly Asp Asn Tyr Gly Ser Asp Phe Phe Ile Ser Asp Glu Gly Lys Asn
    770                 775                 780

Leu Arg Phe Gln Leu Pro Lys Ala Ile Thr His Leu Lys Leu Val Asn
785                 790                 795                 800

Val Asn Gly Asn Asn Lys Leu Val Pro Cys Thr Lys Asp Gly Asn Glu
                805                 810                 815

His Pro Glu Gly Met Pro Ser Asp Leu Thr Asp Glu Tyr Arg Tyr Ile
            820                 825                 830

Asp Pro Ile Phe Ala His Thr Phe Glu Lys Gln Ser Tyr Ser Lys Asn
        835                 840                 845

Ser Ile Ser Val Gly Leu Val Asp Phe Ser Lys Tyr Lys Glu Gly Ser
    850                 855                 860

Met Phe Lys Leu Gln His Tyr Ser Asp Asp Tyr His Ile His Lys Asp
865                 870                 875                 880

Glu Gln Gly Asn Val Ile Arg Pro Asn Asn Arg Ser Tyr Val Thr Lys
                885                 890                 895

Val Asp Leu Val Tyr Asp Asp Lys Val Ile Gly Met Leu Ser Asp Ser
            900                 905                 910

Ile Asn Gln Phe Gln Gly Asp Ile Phe Ile Ser Ala Ser Leu Asn Tyr
        915                 920                 925

Ser His Asn Asp Phe Leu Ser Ser Lys Tyr Phe Gln Lys Val Asn Ile
    930                 935                 940

Glu Ala Leu Glu Asn Gly Ile Tyr Ser Gly Arg Tyr Asp Val Gly Asp
945                 950                 955                 960

Gly Asp Gln Ile Ala Gly Leu Asn Thr Asp Thr Gly Tyr Ser Asp Lys
                965                 970                 975

Ala Ile Phe Tyr Phe Lys Asn Asp Ser Ala Ser Thr Asp Met Pro Ala
            980                 985                 990

Ser Asp Val Thr Thr Ile Leu Pro  Tyr Ile Asn Glu Leu
        995                 1000                1005
```

<210> SEQ ID NO 13
<211> LENGTH: 2172
<212> TYPE: DNA
<213> ORGANISM: Ehrlichia canis

<400> SEQUENCE: 13

```
atggatagta taagtgcaaa tcacatacgc aatattttat tccttgtttt aggcgcattt     60
tttggactgg aattttgctt ttatttatca ggtgtattat tcatcttaat ggtctgggga    120
ccaaattacc tagattttaa tgctataaat cccagtttga gtgattttcc agacagaatt    180
tggccaacta tttttgacta tgtacaacat tggtggaaga acccttctgc atacgatgca    240
gttttattac ttaagctaat aacgtcatta tgtacaccag taggtattct aagcatagta    300
ttatggaacc ttagaaatat attattcgat tggaggccat ttaagaagaa agaatcactg    360
catggagatt caagatgggc aacagaaaaa gatattcgca aaataggatt acgtagtaga    420
```

```
aaaggaatat tattagggaa agacaagaga ggatatctca ttgcagatgg atatcaacat    480
gcattgttat ttgcaccaac tggatccgga aaaggtgtag gttttgtaat accaaactta    540
ttattctggg aagattctgt agtagtacac gatataaaat tagagaacta tgatcttaca    600
agtgggtgga gaaaaaaaag gggacaagaa gttttcgtgt ggaacccagc acaacctgac    660
ggtataagtc actgttacaa cccattagat tggataagct ctaagcctgg acaaatggta    720
gatgatgtac aaaaaattgc caatctaata atgcctgaac aagattttg gtataacgaa     780 gcacgtagtt tatttgtagg agtagtatta tacttactag cagtaccaga aaagtaaaa     840 tcctttggag aagttgtaag aacaatgcgc agcgatgacg tagtctacaa cttagcagta    900
gtactagaca caatagggaa aaagattcac ccagttgcat acatgaatat agctgcattt    960
ttacaaaaag cagacaaaga acgctcaggt gttgtatcaa ctatgaactc atctttagaa   1020
ttatgggcaa acccattaat agatacagca acagcatcaa gtgattttaa tattcaagaa   1080
tttaaaagga aaaaagtaac agtatatgtt ggattaacac cagataattt aactcgtctt   1140
agacctttaa tgcaggtatt ttatcaacaa gctacagaat ttttatgtag aactttacca   1200
tcagatgatg aaccatatgg tgtactgttc ttaatggatg agtttccaac attaggaaaa   1260
atggagcaat ttcaaacagg tatcgcatat ttccgtggat atagagttag actattttg    1320 attattcaag atactgaaca gcttaagggt atatatgaag aagcaggaat gaactcattc   1380
ttatcaaact ctacttatag aataactttt gctgcaaata atatagaaac tgcaaattta   1440
atatcacagt taataggaaa taaaactgtt aaccaagagt ctttaaacag acctaaattt   1500
ttagatttga accctgcatc acgttcatta catatatcag aaacacaaag agctttacta   1560
ttacctcaag aagtaataat gttacccaga gatgagcaaa tacttttaat agaatctact   1620
tatcctataa aatcaaagaa aataaaatac tatgaagaca aaattttac aaaaaaacta    1680 ttaaagagta cctttgttcc aactcaagag ccttatgatc ccaacaaaac aaaaacagca   1740
acaaaagaaa acgaagaacc tatgccaagt attgaaagcg atcttcctaa aaatacatct   1800
gacaatactg aaaacaatat ggaagatggt gcaatgtaca gcagcataga agaagattat   1860
gacgatgatg atgatgattt taattttgaa gacttagatg aatatatgga tgaagaagaa   1920
gattatgatg atgaagaata tgatgatata gattatgatg ataataacaa tagtaatgag   1980
gagtatgaag aagataatcc agaagaagat gacaatagca ataatctaga cgatgaggaa   2040
gaggaagaag ataatattat agattatgaa gatgaagaag aatatgatga taacatagac   2100
tacaaagatg atgacaataa ctacaacaaa gataccactg acgatcaaga ctcaaaaaaa   2160
cataatgaat ag                                                        2172
```

```
<210> SEQ ID NO 14
<211> LENGTH: 723
<212> TYPE: PRT
<213> ORGANISM: Ehrlichia canis

<400> SEQUENCE: 14

Met Asp Ser Ile Ser Ala Asn His Ile Arg Asn Ile Leu Phe Leu Val
1               5                   10                  15

Leu Gly Ala Phe Phe Gly Leu Glu Phe Cys Phe Tyr Leu Ser Gly Val
            20                  25                  30

Leu Phe Ile Leu Met Val Trp Gly Pro Asn Tyr Leu Asp Phe Asn Ala
        35                  40                  45

Ile Asn Pro Ser Leu Ser Asp Phe Pro Asp Arg Ile Trp Pro Thr Ile
```

-continued

```
            50                  55                  60
Phe Asp Tyr Val Gln His Trp Trp Lys Asn Pro Ser Ala Tyr Asp Ala
 65                  70                  75                  80

Val Leu Leu Leu Lys Leu Ile Thr Ser Leu Cys Thr Pro Val Gly Ile
                 85                  90                  95

Leu Ser Ile Val Leu Trp Asn Leu Arg Asn Ile Leu Phe Asp Trp Arg
                100                 105                 110

Pro Phe Lys Lys Lys Glu Ser Leu His Gly Asp Ser Arg Trp Ala Thr
                115                 120                 125

Glu Lys Asp Ile Arg Lys Ile Gly Leu Arg Ser Arg Lys Gly Ile Leu
130                 135                 140

Leu Gly Lys Asp Lys Arg Gly Tyr Leu Ile Ala Asp Gly Tyr Gln His
145                 150                 155                 160

Ala Leu Leu Phe Ala Pro Thr Gly Ser Gly Lys Gly Val Gly Phe Val
                165                 170                 175

Ile Pro Asn Leu Leu Phe Trp Glu Asp Ser Val Val His Asp Ile
                180                 185                 190

Lys Leu Glu Asn Tyr Asp Leu Thr Ser Gly Trp Arg Lys Lys Arg Gly
                195                 200                 205

Gln Glu Val Phe Val Trp Asn Pro Ala Gln Pro Asp Gly Ile Ser His
                210                 215                 220

Cys Tyr Asn Pro Leu Asp Trp Ile Ser Ser Lys Pro Gly Gln Met Val
225                 230                 235                 240

Asp Asp Val Gln Lys Ile Ala Asn Leu Ile Met Pro Glu Gln Asp Phe
                245                 250                 255

Trp Tyr Asn Glu Ala Arg Ser Leu Phe Val Gly Val Val Leu Tyr Leu
                260                 265                 270

Leu Ala Val Pro Glu Lys Val Lys Ser Phe Gly Glu Val Val Arg Thr
                275                 280                 285

Met Arg Ser Asp Asp Val Val Tyr Asn Leu Ala Val Val Leu Asp Thr
                290                 295                 300

Ile Gly Lys Lys Ile His Pro Val Ala Tyr Met Asn Ile Ala Ala Phe
305                 310                 315                 320

Leu Gln Lys Ala Asp Lys Glu Arg Ser Gly Val Val Ser Thr Met Asn
                325                 330                 335

Ser Ser Leu Glu Leu Trp Ala Asn Pro Leu Ile Asp Thr Ala Thr Ala
                340                 345                 350

Ser Ser Asp Phe Asn Ile Gln Glu Phe Lys Arg Lys Val Thr Val
                355                 360                 365

Tyr Val Gly Leu Thr Pro Asp Asn Leu Thr Arg Leu Arg Pro Leu Met
                370                 375                 380

Gln Val Phe Tyr Gln Gln Ala Thr Glu Phe Leu Cys Arg Thr Leu Pro
385                 390                 395                 400

Ser Asp Asp Glu Pro Tyr Gly Val Leu Phe Leu Met Asp Glu Phe Pro
                    405                 410                 415

Thr Leu Gly Lys Met Glu Gln Phe Gln Thr Gly Ile Ala Tyr Phe Arg
                420                 425                 430

Gly Tyr Arg Val Arg Leu Phe Leu Ile Ile Gln Asp Thr Glu Gln Leu
                435                 440                 445

Lys Gly Ile Tyr Glu Glu Ala Gly Met Asn Ser Phe Leu Ser Asn Ser
                450                 455                 460

Thr Tyr Arg Ile Thr Phe Ala Ala Asn Asn Ile Glu Thr Ala Asn Leu
465                 470                 475                 480
```

-continued

```
Ile Ser Gln Leu Ile Gly Asn Lys Thr Val Asn Gln Glu Ser Leu Asn
            485                 490                 495

Arg Pro Lys Phe Leu Asp Leu Asn Pro Ala Ser Arg Ser Leu His Ile
            500                 505                 510

Ser Glu Thr Gln Arg Ala Leu Leu Pro Gln Glu Val Ile Met Leu
            515                 520                 525

Pro Arg Asp Glu Gln Ile Leu Leu Ile Glu Ser Thr Tyr Pro Ile Lys
            530                 535                 540

Ser Lys Lys Ile Lys Tyr Tyr Glu Asp Lys Asn Phe Thr Lys Lys Leu
545                 550                 555                 560

Leu Lys Ser Thr Phe Val Pro Thr Gln Glu Pro Tyr Asp Pro Asn Lys
                565                 570                 575

Thr Lys Thr Ala Thr Lys Glu Asn Glu Pro Met Pro Ser Ile Glu
            580                 585                 590

Ser Asp Leu Pro Lys Asn Thr Ser Asp Asn Thr Glu Asn Asn Met Glu
            595                 600                 605

Asp Gly Ala Met Tyr Ser Ser Ile Glu Glu Asp Tyr Asp Asp Asp
            610                 615                 620

Asp Asp Phe Asn Phe Glu Asp Leu Asp Glu Tyr Met Asp Glu Glu Glu
625                 630                 635                 640

Asp Tyr Asp Asp Glu Glu Tyr Asp Asp Ile Asp Tyr Asp Asn Asn
                645                 650                 655

Asn Ser Asn Glu Glu Tyr Glu Glu Asp Asn Pro Glu Glu Asp Asp Asn
            660                 665                 670

Ser Asn Asn Leu Asp Asp Glu Glu Glu Glu Asp Asn Ile Ile Asp
            675                 680                 685

Tyr Glu Asp Glu Glu Tyr Asp Asp Asn Ile Asp Tyr Lys Asp Asp
            690                 695                 700

Asp Asn Asn Tyr Asn Lys Asp Thr Thr Asp Asp Gln Asp Ser Lys Lys
705                 710                 715                 720

His Asn Glu

<210> SEQ ID NO 15
<211> LENGTH: 688
<212> TYPE: PRT
<213> ORGANISM: Ehrlichia canis

<400> SEQUENCE: 15

Met Asp Ile Asp Asn Asn Asn Val Thr Thr Ser Ser Thr Gln Asp Lys
1               5                   10                  15

Ser Gly Asn Leu Met Glu Val Ile Met Arg Ile Leu Asn Phe Gly Asn
            20                  25                  30

Asn Ser Asp Glu Lys Val Ser Asn Glu Asp Thr Lys Val Leu Val Glu
        35                  40                  45

Ser Leu Gln Pro Ala Val Asn Asp Asn Val Gly Asn Pro Ser Ser Glu
    50                  55                  60

Val Gly Lys Glu Glu Asn Ala Pro Glu Val Lys Ala Glu Asp Leu Gln
65                  70                  75                  80

Pro Ala Val Asp Gly Ser Val Glu His Ser Ser Glu Val Gly Lys
                85                  90                  95

Lys Val Ser Glu Thr Ser Lys Glu Glu Ser Thr Pro Glu Val Lys Ala
            100                 105                 110

Glu Asp Leu Gln Pro Ala Val Asp Gly Ser Ile Glu His Ser Ser Ser
        115                 120                 125
```

```
Glu Val Gly Glu Lys Val Ser Lys Thr Ser Lys Glu Glu Ser Thr Pro
            130                 135                 140

Glu Val Lys Ala Glu Asp Leu Gln Pro Ala Val Asp Asp Ser Val Glu
145                 150                 155                 160

His Ser Ser Glu Val Gly Glu Lys Val Ser Glu Thr Ser Lys Glu
                165                 170                 175

Glu Asn Thr Pro Glu Val Lys Ala Glu Asp Leu Gln Pro Ala Val Asp
                180                 185                 190

Gly Ser Ile Glu His Ser Ser Glu Val Gly Glu Lys Val Ser Lys
            195                 200                 205

Thr Ser Lys Glu Glu Ser Thr Pro Glu Val Lys Ala Glu Asp Leu Gln
            210                 215                 220

Pro Ala Val Asp Asp Ser Val Glu His Ser Ser Glu Val Gly Glu
225                 230                 235                 240

Lys Val Ser Glu Thr Ser Lys Glu Glu Asn Thr Pro Glu Val Lys Ala
                245                 250                 255

Glu Asp Leu Gln Pro Ala Val Asp Gly Ser Val Glu His Ser Ser Ser
                260                 265                 270

Glu Val Gly Glu Lys Val Ser Lys Thr Ser Lys Glu Glu Ser Thr Pro
            275                 280                 285

Glu Val Lys Ala Glu Asp Leu Gln Pro Ala Val Asp Asp Ser Val Glu
            290                 295                 300

His Ser Ser Glu Val Gly Glu Lys Val Ser Glu Thr Ser Lys Glu
305                 310                 315                 320

Glu Asn Thr Pro Glu Val Arg Ala Glu Asp Leu Gln Pro Ala Val Asp
                325                 330                 335

Gly Ser Val Glu His Ser Ser Glu Val Gly Glu Lys Val Ser Glu
            340                 345                 350

Thr Ser Lys Glu Glu Ser Thr Pro Glu Val Lys Ala Glu Asp Leu Gln
            355                 360                 365

Pro Ala Val Asp Ser Ser Ile Glu His Ser Ser Glu Val Gly Lys
            370                 375                 380

Lys Val Ser Glu Thr Ser Lys Glu Glu Ser Thr Pro Glu Val Lys Ala
385                 390                 395                 400

Glu Asp Leu Gln Pro Ala Val Asp Gly Ser Val Glu His Ser Ser Ser
                405                 410                 415

Glu Val Gly Glu Lys Val Ser Thr Ser Lys Glu Glu Asn Thr Pro
            420                 425                 430

Glu Val Lys Ala Glu Asp Leu Gln Pro Ala Val Asp Gly Ser Val Glu
            435                 440                 445

His Ser Ser Glu Val Gly Glu Lys Val Ser Glu Thr Ser Lys Glu
            450                 455                 460

Glu Asn Thr Pro Glu Val Lys Ala Glu Asp Leu Gln Pro Ala Val Asp
465                 470                 475                 480

Gly Ser Val Glu His Ser Ser Glu Val Gly Glu Lys Val Ser Glu
            485                 490                 495

Thr Ser Lys Glu Glu Ser Thr Pro Glu Val Lys Ala Glu Asp Leu Gln
            500                 505                 510

Pro Ala Val Asp Asp Ser Val Glu His Ser Ser Glu Val Gly Glu
            515                 520                 525

Lys Val Ser Glu Thr Ser Lys Glu Glu Ser Thr Pro Glu Val Lys Ala
530                 535                 540
```

-continued

```
Glu Asp Leu Gln Pro Ala Val Asp Gly Ser Val Glu His Ser Ser Ser
545                 550                 555                 560

Glu Val Gly Glu Lys Val Ser Glu Thr Ser Lys Glu Ser Thr Pro
            565                 570                 575

Glu Val Lys Ala Glu Val Gln Pro Val Ala Asp Gly Asn Pro Val Pro
                580                 585                 590

Leu Asn Pro Met Pro Ser Ile Asp Asn Ile Asp Thr Asn Ile Ile Phe
            595                 600                 605

His Tyr His Lys Asp Cys Lys Lys Gly Ser Ala Val Gly Thr Asp Glu
            610                 615                 620

Met Cys Cys Pro Val Ser Glu Leu Met Ala Gly Glu His Val His Met
625                 630                 635                 640

Tyr Gly Ile Tyr Val Tyr Arg Val Gln Ser Val Lys Asp Leu Ser Gly
                645                 650                 655

Val Phe Asn Ile Asp His Ser Thr Cys Asp Cys Asn Leu Asp Val Tyr
            660                 665                 670

Phe Val Gly Tyr Asn Ser Phe Thr Asn Lys Glu Thr Val Asp Leu Ile
            675                 680                 685

<210> SEQ ID NO 16
<211> LENGTH: 515
<212> TYPE: PRT
<213> ORGANISM: Ehrlichia canis

<400> SEQUENCE: 16

Lys Glu Glu Asn Ala Pro Glu Val Lys Ala Glu Asp Leu Gln Pro Ala
1               5                   10                  15

Val Asp Gly Ser Val Glu His Ser Ser Ser Glu Val Gly Lys Lys Val
            20                  25                  30

Ser Glu Thr Ser Lys Glu Glu Ser Thr Pro Glu Val Lys Ala Glu Asp
        35                  40                  45

Leu Gln Pro Ala Val Asp Gly Ser Ile Glu His Ser Ser Ser Glu Val
    50                  55                  60

Gly Glu Lys Val Ser Lys Thr Ser Lys Glu Glu Ser Thr Pro Glu Val
65                  70                  75                  80

Lys Ala Glu Asp Leu Gln Pro Ala Val Asp Asp Ser Val Glu His Ser
                85                  90                  95

Ser Ser Glu Val Gly Glu Lys Val Ser Glu Thr Ser Lys Glu Glu Asn
            100                 105                 110

Thr Pro Glu Val Lys Ala Glu Asp Leu Gln Pro Ala Val Asp Gly Ser
        115                 120                 125

Ile Glu His Ser Ser Ser Glu Val Gly Glu Lys Val Ser Lys Thr Ser
    130                 135                 140

Lys Glu Glu Ser Thr Pro Glu Val Lys Ala Glu Asp Leu Gln Pro Ala
145                 150                 155                 160

Val Asp Asp Ser Val Glu His Ser Ser Ser Glu Val Gly Glu Lys Val
                165                 170                 175

Ser Glu Thr Ser Lys Glu Glu Asn Thr Pro Glu Val Lys Ala Glu Asp
            180                 185                 190

Leu Gln Pro Ala Val Asp Gly Ser Val Glu His Ser Ser Ser Glu Val
        195                 200                 205

Gly Glu Lys Val Ser Lys Thr Ser Lys Glu Glu Ser Thr Pro Glu Val
    210                 215                 220

Lys Ala Glu Asp Leu Gln Pro Ala Val Asp Asp Ser Val Glu His Ser
225                 230                 235                 240
```

```
Ser Ser Glu Val Gly Glu Lys Val Ser Glu Thr Ser Lys Glu Asn
            245                 250                 255

Thr Pro Glu Val Arg Ala Glu Asp Leu Gln Pro Ala Val Asp Gly Ser
        260                 265                 270

Val Glu His Ser Ser Glu Val Gly Glu Lys Val Ser Glu Thr Ser
        275                 280                 285

Lys Glu Glu Ser Thr Pro Glu Val Lys Ala Glu Asp Leu Gln Pro Ala
        290                 295                 300

Val Asp Ser Ser Ile Glu His Ser Ser Glu Val Gly Lys Lys Val
305                 310                 315                 320

Ser Glu Thr Ser Lys Glu Ser Thr Pro Glu Val Lys Ala Glu Asp
                325                 330                 335

Leu Gln Pro Ala Val Asp Gly Ser Val Glu His Ser Ser Glu Val
            340                 345                 350

Gly Glu Lys Val Ser Glu Thr Ser Lys Glu Glu Asn Thr Pro Glu Val
            355                 360                 365

Lys Ala Glu Asp Leu Gln Pro Ala Val Asp Gly Ser Val Glu His Ser
        370                 375                 380

Ser Ser Glu Val Gly Glu Lys Val Ser Glu Thr Ser Lys Glu Glu Asn
385                 390                 395                 400

Thr Pro Glu Val Lys Ala Glu Asp Leu Gln Pro Ala Val Asp Gly Ser
            405                 410                 415

Val Glu His Ser Ser Glu Val Gly Glu Lys Val Ser Glu Thr Ser
                420                 425                 430

Lys Glu Glu Ser Thr Pro Glu Val Lys Ala Glu Asp Leu Gln Pro Ala
        435                 440                 445

Val Asp Asp Ser Val Glu His Ser Ser Ser Glu Val Gly Glu Lys Val
        450                 455                 460

Ser Glu Thr Ser Lys Glu Glu Ser Thr Pro Glu Val Lys Ala Glu Asp
465                 470                 475                 480

Leu Gln Pro Ala Val Asp Gly Ser Val Glu His Ser Ser Ser Glu Val
            485                 490                 495

Gly Glu Lys Val Ser Glu Thr Ser Lys Glu Glu Ser Thr Pro Glu Val
            500                 505                 510

Lys Ala Glu
        515

<210> SEQ ID NO 17
<211> LENGTH: 36
<212> TYPE: PRT
<213> ORGANISM: Ehrlichia canis
<220> FEATURE:
<221> NAME/KEY: MISC_FEATURE
<222> LOCATION: (4)..(4)
<223> OTHER INFORMATION: X stands for any amino acid
<220> FEATURE:
<221> NAME/KEY: MISC_FEATURE
<222> LOCATION: (9)..(9)
<223> OTHER INFORMATION: X stands for any amino acid
<220> FEATURE:
<221> NAME/KEY: MISC_FEATURE
<222> LOCATION: (19)..(19)
<223> OTHER INFORMATION: X stands for any amino acid
<220> FEATURE:
<221> NAME/KEY: MISC_FEATURE
<222> LOCATION: (21)..(21)
<223> OTHER INFORMATION: X stands for any amino acid
<220> FEATURE:
<221> NAME/KEY: MISC_FEATURE
<222> LOCATION: (30)..(30)
```

```
<223> OTHER INFORMATION: X stands for any amino acid
<220> FEATURE:
<221> NAME/KEY: MISC_FEATURE
<222> LOCATION: (34)..(34)
<223> OTHER INFORMATION: X stands for any amino acid

<400> SEQUENCE: 17

Lys Glu Glu Xaa Thr Pro Glu Val Xaa Ala Glu Asp Leu Gln Pro Ala
1               5                   10                  15

Val Asp Xaa Ser Xaa Glu His Ser Ser Glu Val Gly Xaa Lys Val
            20                  25                  30

Ser Xaa Thr Ser
        35

<210> SEQ ID NO 18
<211> LENGTH: 19
<212> TYPE: PRT
<213> ORGANISM: Ehrlichia canis

<400> SEQUENCE: 18

Cys Pro Glu Val Lys Ala Glu Asp Leu Gln Pro Ala Val Asp Gly Ser
1               5                   10                  15

Val Glu His

<210> SEQ ID NO 19
<211> LENGTH: 27
<212> TYPE: PRT
<213> ORGANISM: Ehrlichia canis

<400> SEQUENCE: 19

Cys Glu Val Gly Lys Glu Glu Asn Ala Pro Glu Val Lys Ala Glu Asp
1               5                   10                  15

Leu Gln Pro Ala Val Asp Gly Ser Val Glu His
            20                  25

<210> SEQ ID NO 20
<211> LENGTH: 37
<212> TYPE: PRT
<213> ORGANISM: Ehrlichia canis

<400> SEQUENCE: 20

Cys Lys Glu Glu Ser Thr Pro Glu Val Lys Ala Glu Asp Leu Gln Pro
1               5                   10                  15

Ala Val Asp Gly Ser Val Glu His Ser Ser Ser Glu Val Gly Glu Lys
            20                  25                  30

Val Ser Glu Thr Ser
        35

<210> SEQ ID NO 21
<211> LENGTH: 48
<212> TYPE: PRT
<213> ORGANISM: Ehrlichia canis
<220> FEATURE:
<221> NAME/KEY: MISC_FEATURE
<222> LOCATION: (1)..(15)
<223> OTHER INFORMATION: X stands for any amino acid or no amino acid
<220> FEATURE:
<221> NAME/KEY: MISC_FEATURE
<222> LOCATION: (34)..(48)
<223> OTHER INFORMATION: X stands for any amino acid or no amino acid

<400> SEQUENCE: 21

Xaa Xaa Xaa Xaa Xaa Xaa Xaa Xaa Xaa Xaa Xaa Xaa Xaa Xaa Xaa Pro
1               5                   10                  15
```

```
Glu Val Lys Ala Glu Asp Leu Gln Pro Ala Val Asp Gly Ser Val Glu
             20                  25                  30

His Xaa Xaa Xaa Xaa Xaa Xaa Xaa Xaa Xaa Xaa Xaa Xaa Xaa Xaa
         35                  40                  45

<210> SEQ ID NO 22
<211> LENGTH: 37
<212> TYPE: PRT
<213> ORGANISM: Ehrlichia canis
<220> FEATURE:
<221> NAME/KEY: MISC_FEATURE
<222> LOCATION: (31)..(31)
<223> OTHER INFORMATION: X is K or E

<400> SEQUENCE: 22

Cys Lys Glu Glu Ser Thr Pro Glu Val Lys Ala Glu Asp Leu Gln Pro
1               5                  10                  15

Ala Val Asp Gly Ser Val Glu His Ser Ser Ser Glu Val Gly Xaa Lys
             20                  25                  30

Val Ser Glu Thr Ser
         35
```

*EHRLICHIA CANIS* DIVA (DIFFERENTIATE INFECTED FROM VACCINATED ANIMALS)

PRIORITY

This application is a continuation-in-part of U.S. Ser. No. 11/397,222, filed Apr. 4, 2006 and PCT/IUS06/012432, filed Apr. 4, 2006, which claim the benefit of U.S. Appl. No. 60/668,205, filed on Apr. 4, 2005, all of which are incorporated herein by reference in their entirety.

BACKGROUND OF THE INVENTION

The *Ehrlichia* are obligate intracellular pathogens that infect circulating white blood cells in mammalian hosts. *Ehrlichia canis* can infect canines and humans and cause canine monocytic ehrlichiosis (CME) and human monocytic ehrlichiosis (HME), respectively. The canine disease is characterized by fever, lymphadenopathy, weight loss, and pancytopenia. In humans the disease is characterized by fever, headache, mylagia, and leukopenia. Early detection and treatment are important for treating both canine and human ehrlichiosis.

SUMMARY OF THE INVENTION

In one embodiment the invention provides a method for determining whether an animal is infected with *Ehrlichia canis*, or is either not infected or is vaccinated with an *E. canis* vaccine. The method comprises contacting a biological sample from the animal with a first purified *E. canis* polypeptide that is not an element of the *E. canis* vaccine; and detecting whether an antibody in the sample specifically binds to the first purified *E. canis* polypeptide. If an antibody in the sample specifically binds to the first purified *E. canis* polypeptide, then the animal is infected with *E. canis* and if an antibody does not specifically bind to the purified *E. canis* polypeptide, then the animal is either vaccinated or is not infected. The first purified *E. canis* polypeptide can comprise SEQ ID NOs:2, 4, 6, 8, 10, 12, 14, 15, 16, 17, 18, 19, 20, 21, 22 or a combination thereof. The *E. canis* vaccine can comprise at least one *E. canis* p28-1, p28-2, p28-3, p28-4, p28-5, p28-6, p28-7, p28-8, p28-9, proA, ProB, mmpA, cytochrome oxidase, p43, p153 polypeptide, or a combination thereof. The *E. canis* vaccine can comprise a vector encoding at least one *E. canis* p28-1, p28-2, p28-3, p28-4, p28-5, p28-6, p28-7, p28-8, p28-9, proA, ProB, mmpA, cytochrome oxidase, p43, p153 polypeptide, or a combination thereof.

The method can further comprise detecting whether an antibody in the sample specifically binds to a second purified *E. canis* polypeptide that is an element of an *E. canis* vaccine, and determining that the animal has been vaccinated for *E. canis* by detecting that an antibody in the sample specifically binds to the second purified *E. canis* polypeptide, or determining that the animal has not been vaccinated for *E. canis* and has not been infected by *E. canis* by detecting that no antibody in the sample specifically binds to the second purified *E. canis* polypeptide.

Another embodiment of the invention provides a method of distinguishing between animals that have been infected with *E. canis* and animals that have not been infected or have been vaccinated with an *E. canis* vaccine. The method comprises contacting a biological sample from an animal with a first purified *E. canis* polypeptide that does not specifically bind to antibodies that are a component of the animal's immune response to an *E. canis* vaccine, detecting whether an antibody in the sample specifically binds to the first purified *E. canis* polypeptide, and determining that the animal is infected by correlating a positive result in the detecting step to a natural infection and determining that the animal has been vaccinated or is not infected by correlating a negative result to a vaccination or no infection. The first purified *E. canis* polypeptide can comprise SEQ ID NOs: 2, 4, 6, 8, 10, 12, 14, 15, 16, 17, 18, 19, 20, 21, 22 or combinations thereof. The method can further comprise detecting whether an antibody in the sample specifically binds to a second purified *E. canis* polypeptide that specifically binds an antibody that is a component of the animal's immune response to the vaccine, thereby determining whether the animal has been vaccinated.

Still another embodiment of the invention provides a method of determining whether an animal is either not infected or has been vaccinated against *E. canis* with an *E. canis* vaccine, or is infected with *E. canis* comprising determining the animal's immune response to a first purified polypeptide derived from *E. canis* that is not an element of an *E. canis* vaccine. The first *E. canis* polypeptide can comprise SEQ ID NOs: 2, 4, 6, 8, 10, 12, 14, 15, 16, 17, 18, 19, 20, 21, 22 or combinations thereof. The method can further comprise determining, in those animals that do not have an immune response to the first purified polypeptide, whether the animal has been vaccinated by determining the animal's immune response to a second purified polypeptide that is an element of the *E. canis* vaccine.

Even another embodiment of the invention provides a method for determining the vaccination or infection status of an animal for *E. canis*. The method comprises contacting a biological sample from the animal with a reagent comprising a first purified *E. canis* polypeptide that is not an element of an *E. canis* vaccine and detecting whether the first purified *E. canis* polypeptide specifically binds to an antibody in the biological sample. If the first purified *E. canis* polypeptide specifically binds to an antibody in the sample, then the animal is infected with *E. canis* and, if the first purified *E. canis* polypeptide does not specifically bind to an antibody in the sample, then the animal is either not infected with *E. canis* or has been vaccinated with a vaccine that does not comprise the first purified *E. canis* polypeptide. The first purified *E. canis* polypeptide can comprise SEQ ID NOs: 2, 4, 6, 8, 10, 12, 14, 15, 16, 17, 18, 19, 20, 21, 22 or combinations thereof. The method can further comprise, detecting whether an antibody in the sample specifically binds to a second purified *E. canis* polypeptide that specifically binds an antibody that is a component of the animal's immune response to the *E. canis* vaccine, thereby determining whether the animal has been vaccinated.

Another embodiment of the invention provides a method of determining whether an animal is infected with *E. canis*, is vaccinated with an *E. canis* vaccine, or is not infected and not vaccinated. The method comprises contacting a biological sample from the animal with a first purified *E. canis* polypeptide that is not an element of the *E. canis* vaccine, contacting the biological sample with a second purified *E. canis* polypeptide that is an element of the *E. canis* vaccine; and detecting whether antibodies in the sample specifically bind to the first and the second purified *E. canis* polypeptides. If antibodies in the sample specifically bind to both the first and second purified *E. canis* polypeptides, then the animal is infected with *E. canis*, and if an antibody in the sample specifically binds to the second purified *E. canis* polypeptide but not the first purified *E. canis* polypeptide, then the animal has been vaccinated but is not infected and wherein, and if an antibody does not specifically bind to either polypeptide, then the animal is not infected and not vaccinated. The first purified *E. canis* polypeptide can comprise SEQ ID NOs: 2, 4, 6, 8, 10, 12, 14, 15, 16, 17, 18, 19, 20, 21, 22 or combinations thereof.

Yet another embodiment of the invention provides a method of determining an animal's vaccination and infection status for *E. canis*. The method comprises contacting a biological sample from an animal with a first purified polypeptide that does not specifically bind to antibodies that are a component of the animal's immune response to an *E. canis* vaccine and a second polypeptide that specifically binds to an antibody that is a component of the animal's immune response to an *E. canis* vaccine; detecting whether antibodies in the sample specifically bind to the first and second purified polypeptides; determining that the animal is infected by detecting the specific binding of antibodies in the sample to both the first and second purified polypeptides, determining that that the animal is vaccinated and not infected by detecting the specific binding of an antibody to the second purified polypeptide but not the first purified polypeptide, and determining that the animal is not vaccinated and not infected by detecting the absence of specific binding to the first and second purified *E. canis* polypeptides. The first *E. canis* polypeptide can comprise SEQ ID NOs: 2, 4, 6, 8, 10, 12, 14, 15, 16, 17, 18, 19, 20, 21, 22 or combinations thereof.

Even another embodiment of the invention provides a method for determining the presence or absence of an antibody or fragment thereof, in a test sample, wherein the antibody or fragment thereof specifically binds to a purified polypeptide comprising SEQ ID NOs: 2, 4, 6, 8, 10, 12, 14, 15, 16, 17, 18, 19, or 20. The method comprises contacting the test sample with a purified polypeptide comprising SEQ ID NOs: 2, 4, 6, 8, 10, 12, 14, 15, 16, 17, 18, 19, 20, 21 or 22 under conditions suitable for specific binding of the purified polypeptide to the antibody or fragment thereof, and detecting the presence or absence of specific binding. The presence of specific binding indicates the presence of the antibody or fragment thereof. The absence of specific binding indicates the absence the antibody or fragment thereof. The method can further comprise detecting the amount of specific binding. The test sample can be serum, blood, or saliva. The purified polypeptide can be immobilized to a solid support. The purified polypeptide can be labeled. The detection can be by radioimmunoassay, enzyme-linked immunosorbent assay, immunohistochemical, or immunoenzyme-assay.

Yet another embodiment of the invention provides a method for determining the presence or absence of a polypeptide comprising SEQ ID NOs: 2, 4, 6, 8, 10, 12, 14, 15, 16, 17, 18, 19, 20, 21 or 22 in a test sample. The method comprises contacting the test sample with an antibody or fragment thereof that specifically binds a purified polypeptide consisting of SEQ ID NOs: 2, 4, 6, 8, 10, 12, 14, 15, 16, 17, 18, 19, 20, 21, 22 under conditions suitable for specific binding of the polypeptide to the antibody or fragment thereof, and detecting the presence or absence of specific binding. The presence of specific binding indicates the presence of the polypeptide, and the absence of specific binding indicates that the absence the polypeptide. The method can further comprise detecting the amount of specific binding. The test sample can be serum, blood, or saliva. The antibody or fragment thereof can be immobilized to a solid support. The antibody or fragment thereof can be labeled. The detection can be by radioimmunoassay, enzyme-linked immunosorbent assay, immunohistochemical assay or immunoenzyme-assay.

Another embodiment of the invention provides a composition comprising one or more purified polypeptides consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:15, SEQ ID NO:16, SEQ ID NO:17, 18, 19, 20, 21, 22 or combinations thereof and a polynucleotide encoding the one or more purified polypeptides.

The purified polypeptide can be in a multimeric form. The purified polypeptide can be linked to a heterologous protein (an amino acid sequence not normally associated with the purified polypeptide in nature) an indicator reagent, an amino acid spacer, an amino acid linker, a signal sequence, a stop transfer sequence, a transmembrane domain, a protein purification ligand, or a combination thereof.

Even another embodiment of the invention provides a fusion protein comprising one or more polypeptides consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 or a combination thereof.

Another embodiment of the invention provides a method of generating an immune response in an animal comprising administering one or more purified polypeptides comprising SEQ ID NOs:2, 4, 6, 8, 10, 15, 16, 17, 18, 19, 20, 21, 22 or a combination thereof to the animal.

Yet another embodiment of the invention provides a method for the prophylaxis, treatment, or amelioration of an *Ehrlichia canis* infection in an animal. The method comprises administering (1) one or more purified polypeptides comprising SEQ ID NOs:2, 4, 6, 8, 10, 15, 16, 17, 18, 19, 20, 21, 22 or a combination thereof; one or more nucleic acids encoding one or more purified polypeptides comprising SEQ ID NOs: 2, 4, 6, 8, 10, 15, 16, 17, 18, 19, 20, 21, 22 or a combination thereof.

Therefore, the invention provides *Ehrlichia canis* antigens that can be used to differentiate *E. canis* naturally-infected animals from animals that have been challenged with *E. canis*, e.g., vaccinated against *E. canis*. The invention also provides compositions and methods for determining the presence of *E. canis* antigens and antibodies and for the treatment, amelioration, and prevention of *E. canis* infection.

BRIEF DESCRIPTION OF THE DRAWINGS

FIG. 6 shows a Western blot of six different *E. canis* DIVA antigens expressed in *E. coli* and probed with either dog sera from a pool of four infected animals (A) or dog sera pooled from four challenged animals (B). Sera dilutions were 1:100 for challenged animals or 1:500 for the infected animals. The DIVA antigens represented include: (1) 200 kDa antigen, (2)

Figure 1:
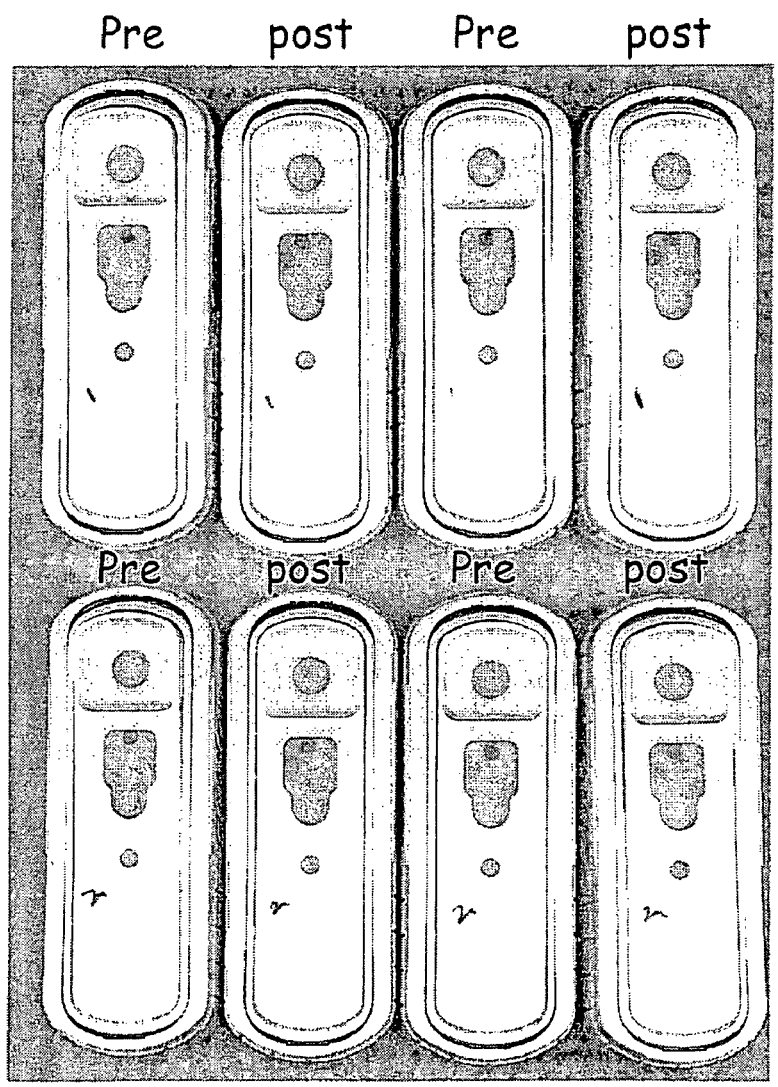
FIG. 1 shows SNAP® 3Dx® reversible flow chromatographic assay evaluation of laboratory beagles. The SNAP® reversible flow chromatographic assay device was used as described by manufacturer. "Pre" sample is from day 0. "Post" sample is from day 42. The *E. canis* positive spot became positive in all 4 dogs for the day 42 sample. Similar results were observed for the day 70 sample.
Figure 2:
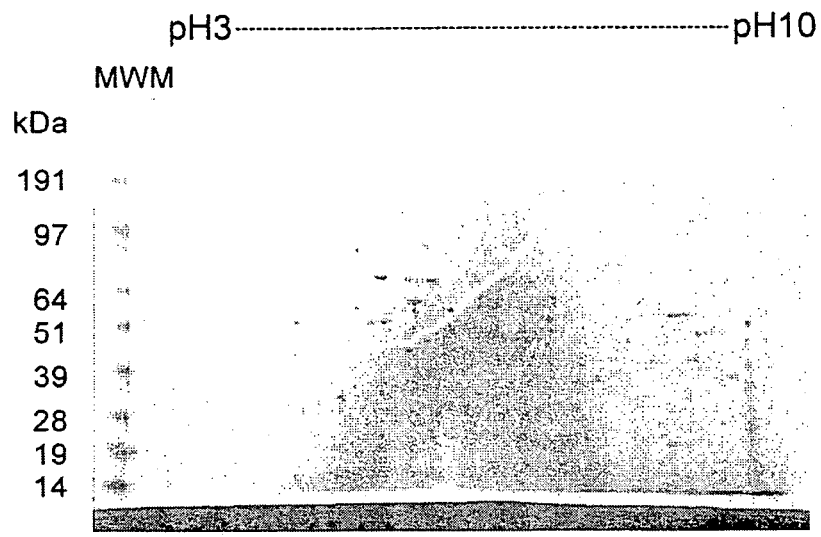
FIG. 2 shows a gel of *E. canis* proteins separated using 2D gel electrophoresis. Stained with BIOSAFE™ Coomassie Blue (Bio-Rad Inc.).
Figure 3:
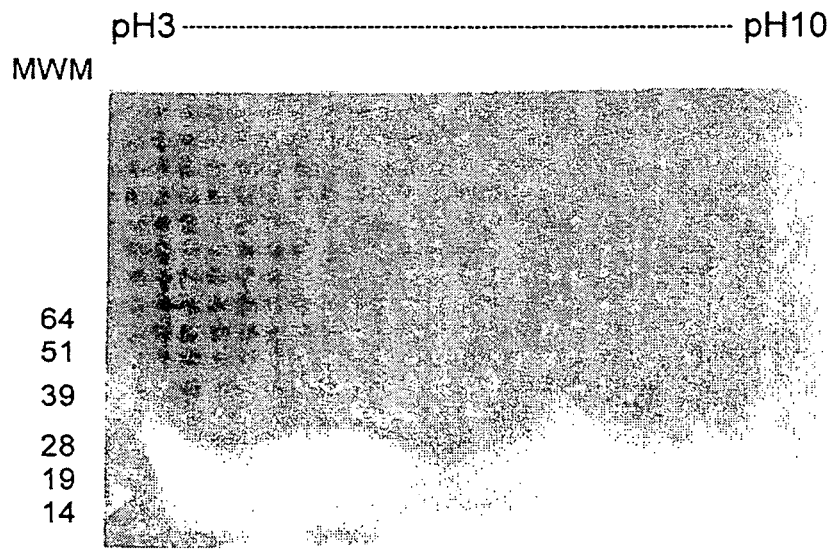
FIG. 3 shows a Western blot of *E. canis* proteins using dog sera harvested at day 0. The plasma dilution is 1:100. These dogs were negative for reactivity with *E. canis* antigens.
Figure 4:
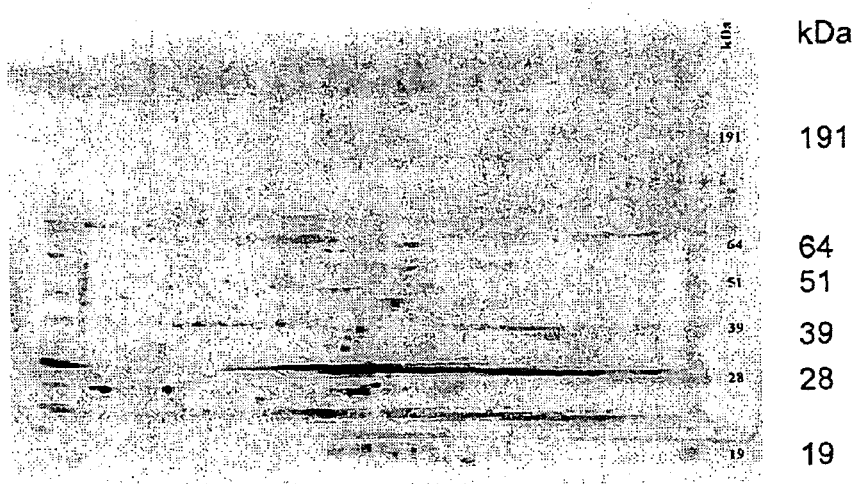
FIG. 4 shows a Western blot of *E. canis* proteins using dog sera from a pool of four challenged animals. The sera dilution is 1:100.
Figure 5:
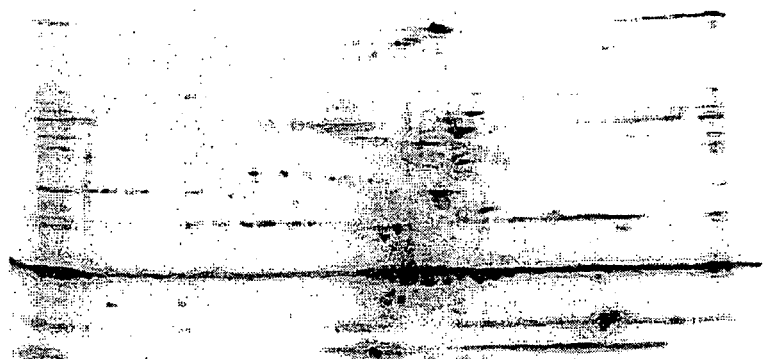
FIG. 5 shows a Western blot of *E. canis* proteins using dog plasma from a pool of infected animals. The sera dilution is 1:1000.

Ribosomal protein L1, (3a and 3b) "ATPase"—two different segments, (4) 120 kDa antigen, (5) Heat shock proteins/p16 antigen.

FIG. 7 demonstrates that cloned p16 antigen is recognized by sera from dogs infected with *E. canis* but not those challenged with the cultured organism. Lysates from uninduced (U) or induced (I) bacteria transformed with a vector expressing the p16 antigen or the original genomic fragment (+C) were separated by SDS-PAGE and transferred to nitrocellulose for Western blot analysis.

DETAILED DESCRIPTION OF THE INVENTION

*Ehrlichia canis* antigens are disclosed that can be used to differentiate *E. canis* naturally-infected animals from animals that have been challenged with *E. canis*, e.g., vaccinated against *E. canis*.

Before describing the present invention in detail, a number of terms will be defined. As used herein, the singular forms "a," "an", and "the" include plural referents unless the context clearly dictates otherwise.

As used herein, the term "polypeptide" refers to a compound of a single chain or a complex of two or more chains of amino acid residues linked by peptide bonds. The chain(s) may be of any length and can comprise a fusion protein. Although "protein" is often used in reference to relatively large polypeptides, and "peptide" is often used in reference to small polypeptides, usage of these terms in the art overlaps and varies. The term "polypeptide" as used herein thus refers interchangeably to peptides, polypeptides, proteins, or fusion proteins unless otherwise noted. The term "amino acid" refers to a monomeric unit of a peptide, polypeptide or protein.

As used herein, "antigen" as used herein refers to a molecule against which a subject can initiate a humoral and/or cellular immune response. Antigens can be any type of biologic molecule including, for example, simple intermediary metabolites, sugars, lipids, and hormones as well as macromolecules such as complex carbohydrates, phospholipids, nucleic acids and proteins. In the compositions and methods of the invention, it is preferred that the antigen is a polypeptide, e.g., one comprising at least about six or more amino acids.

As used herein, a "derivative" of an *E. canis* antigen polypeptide, or an antigen or polypeptide that is "derived from" an *E. canis* antigen or polypeptide, refers to a antigen or polypeptide in which the native form has been purified, modified or altered. Such modifications include, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other modifications, any of which may result in changes in primary, secondary or tertiary structure.

A "biological sample" is any sample from an animal that is expected to contain immunoglobulins. Generally, these samples are whole blood and blood components, but in some circumstances may include saliva, urine, tears, other bodily fluids, tissue extracts or cellular extracts.

An "infection," such as in an *E. canis* infection, means that an animal has been exposed to *E. canis*, regardless of whether the animal exhibits clinical symptoms of *E. canis*. A natural infection refers to an exposure that occurs as a result of one of the natural transmission methods for *E. canis*, such as transmission by ticks. An infection does not include an exposure to *E. canis* through vaccination.

A "polypeptide or antigen that is not an element of an *E. canis* vaccine" is any *E. canis* polypeptide or antigen that is not present in, or is not an immunogenically active portion of, a particular *E. canis* vaccine or vaccines. Elements of the vaccine(s) can be portions of a subunit vaccine that includes less than the entire bacterium; these portions can be chemically synthesized or expressed recombinantly before becoming part of the vaccine, and these portions can be encoded by one or more vectors that express an immunogenic composition in vivo.

An "antibody that is a component of an animal's immune response to an *E. canis* vaccine" refers to an antibody that is elicited as the result of a vaccination with an *E. canis* vaccine. These antibodies can be identical to or similar to antibodies elicited as the result of a natural *E. canis* infection. These antibodies will be maintained at a sufficient titer and so as to provide a protective and neutralizing effect against the bacteria. A successful vaccination produces a measurable level of the antibody (or antibodies) that is elicited by a component of the *E. canis* vaccine. Examples of *E. canis* antigens that elicit antibodies that can be a component of an animal's immune response to an *E. canis* vaccine are p28-1, p28-2, p28-3, p28-4, p28-5, p28-6, p28-7, p28-8, p28-9 (see, U.S. Pat. Nos. 6,660,269; 6,458,942; 6,403,780; 6,392,023), proA, ProB, mmpA, cytochrome oxidase (see, U.S. Pat. Publ. 20040170972), p43 (see, U.S. Pat. No. 6,355,777), which is the N-terminal portion of p153, a glycoprotein (see, U.S. Pat. Publ. 2004/0121433), and p153.

An immune response is the development in an organism of a cellular and/or antibody mediated immune response to an antigen such as a polypeptide. Usually such a response includes but is not limited to one or more of the following: production of antibodies, B cells, helper T cells, suppressor T cells, and/or cytotoxic T cells. An immune response can be detected using any of several assays known to those with skill in the art.

Polypeptides of the Invention

Biological samples from animals that have been vaccinated against *E. canis* have the potential for producing a positive result in a test for *E. canis* infection due to the presence of antibodies produced in response to the vaccine. In one aspect, the invention provides a method of distinguishing between animals that have been infected with *E. canis*, animals that have not been infected with *E. canis*, and animals that have been vaccinated against *E. canis*. Methods include contacting a biological sample from the animal with an antigen derived from *E. canis* that does not specifically bind to an antibody that is a component of the animal's antibody response to a particular *E. canis* vaccine.

The development of *E. canis* antibodies in an animal against a vaccine is dependent upon the particular vaccine used to vaccinate the animal. The difference in the immune response between animals that are vaccinated against *E. canis* and animals that are naturally or experimentally infected with *E. canis* provides a means for determining whether an animal has been vaccinated or is naturally or experimentally infected. Therefore, using the methods of the invention, animals that have been infected with *E. canis* can be distinguished from animals that have not been infected with *E. canis* or have been vaccinated against *E. canis*. Antigens of the invention, their immunodominant regions, and epitopes can be used in the methods of the invention. These compositions can be referred to as *E. canis* DIVA antigens (Differentiate Infected from Vaccinated Animals). An *E. canis* DIVA antigen induces an immune response, e.g., the production of specific antibodies, in an animal that is different from the immune response induced in the animal by a particular *E. canis* vaccine.

Accordingly, the detection of the binding between an *E. canis* DIVA antigen and an antibody that is not a component of an animal's immune response to a particular vaccine can indicate a natural infection. The absence of such binding can indicate vaccination or no infection. In addition, a second, separate antigen, such as an *E. canis* antigen that specifically binds an antibody that is a component of animal's immune response to a particular *E. canis* vaccine, can be used to detect antibodies produced in response to vaccination. The detection of neither antibody indicates no infection and no vaccination. As such, various combinations of separate capture reagents can lead to a determination of the vaccination and/or infection status of the test subject.

In one aspect, a method of the invention includes contacting a biological sample from an animal with an antigen that is a part of the native *E. canis* bacteria, but is not an element of a particular *E. canis* vaccine. An animal is any mammal that is likely to be vaccinated against *E. canis* and, in particular, canines. In addition, humans may be vaccinated against *E. canis*. In another aspect, the invention includes a method of determining whether an animal has not been infected by *E. canis* and has not been vaccinated against *E. canis*. A biological sample from an animal is analyzed to detect the presence or absence of antibodies specific for an *E. canis* DIVA antigen, and the presence or absence of antibodies specific for a particular *E. canis* vaccine. It is then determined that the animal has not been infected and has not been or vaccinated by determining the absence of such antibodies.

In one aspect of the invention, a DIVA antigen is not an element of an *E. canis* vaccine. The vaccination or infection status of an animal can be determined by detecting whether antibodies in the sample bind to one or more antigens used in the vaccine. If antibodies in the sample bind to one or more of the antigens, the animal is either vaccinated or infected. If no antibody binds the DIVA polypeptide, then it can be determined that the animal has been vaccinated. If no binding is detected for either antigen, then it can be determined that the animal is not infected and not vaccinated.

A polypeptide of the invention can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure.

Purified polypeptides of the invention can either be full-length polypeptides or fragments of polypeptides. For example, fragments of polypeptides of the invention can comprise about 6, 10, 20, 30, 40, 50, 60, 70, 80, 90, 100, 250, 500, 750 contiguous amino acids or more of polypeptides of the invention. Examples of polypeptides of the invention include those shown in SEQ ID NOs: 2, 4, 6, 8, 10, 12, 14, 15, 16, 17, 18, 19, 20, 21 or 22. Variant polypeptides are at least about 80, or about 90, 96, 98, or 99% identical to the polypeptide sequences shown in SEQ ID NOs: 2, 4, 6, 8, 10, 12, 14, 15, 16, 17, 18, 19, 20, 21 or 22 and are also polypeptides of the invention. Variant polypeptides have one or more conservative amino acid variations or other minor modifications and retain biological activity, i.e., are biologically functional equivalents. A biologically active equivalent has substantially equivalent function when compared to the corresponding wild-type polypeptide.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variants can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90-110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide. Variant polypeptides of the invention can comprise about 1, 2, 3, 4, 5, or 6 conservative amino acid substitutions.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature. Additionally, a polypeptide can be covalently or non-covalently linked to compounds or molecules other than amino acids. For example, a polypeptide can be linked to an indicator reagent, an amino acid spacer, an amino acid linker, a signal sequence, a stop transfer sequence, a transmembrane domain, a protein purification ligand, or a combination thereof. In one embodiment of the invention a protein purification ligand can be one or more C amino acid residues at, for example, the amino terminus or carboxy terminus of a polypeptide of the invention. An amino acid spacer is a sequence of amino acids that are not usually associated with a polypeptide of the invention in nature. An amino acid spacer can comprise about 1, 5, 10, 20, 100, or 1,000 amino acids.

If desired, a polypeptide can be a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and staphylococcal protein A, or combinations thereof. More than one polypeptide of the invention can be present in a fusion protein. Fragments of polypeptides of the invention can be present in a fusion protein of the invention. A fusion protein of the invention can comprise one or more polypeptides shown in SEQ ID NO: 2, 4, 6, 8, 10, 12, 14, 15, 16, 17, 18, 19, 20, 21 or 22, fragments thereof, or combinations thereof.

Polypeptides of the invention can be in a multimeric form. That is, a polypeptide can comprise one or more copies of SEQ ID NOs: 2, 4, 6, 8, 10, 12, 14, 15, 16, 17, 18, 19, 20, 21, 22 or a combination thereof. A multimeric polypeptide can be a multiple antigen peptide (MAP). See e.g., Tam, J. Immunol. Methods, 196:17-32 (1996).

Polypeptides of the invention can comprise an antigen that is recognized by an antibody reactive against $E.$ $canis$. The antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, $CABIOS$ 4:181-186 (1988). For example, a polypeptide of the invention can be isolated and screened. A series of short peptides, which together span an entire polypeptide sequence, can be prepared by proteolytic cleavage. By starting with, for example, 100-mer polypeptide fragments, each fragment can be tested for the presence of epitopes recognized in an ELISA. For example, in an ELISA assay an $E.$ $canis$ polypeptide, such as, a 100-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 100-mer to map the epitope of interest.

In one embodiment of the invention, a DIVA antigen comprises an immunodominant epitope or region. That is, an epitope or region that more frequently elicits and binds to antibodies in a population thereof when compared with other epitopes. An antigen can have one or more immunodominant epitopes. Immunodominant epitopes can be mapped on, for example, a polypeptide after the polypeptide has been administered to an animal or prior to such administration. See e.g., U.S. Pat. Publ. 2004/0209324.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from $E.$ $canis$ cells.

An immunogenic polypeptide of the invention can comprise an amino acid sequence shown in SEQ ID NOs: 2, 4, 6, 8, 10, 12, 14, 15, 16, 17, 18, 19, 20, 21 or 22. An immunogenic polypeptide can elicit antibodies or other immune responses (e.g., T-cell responses of the immune system) that recognize epitopes of polypeptides having SEQ ID NOs: 2, 4, 6, 8, 10, 12, 14, 15, 16, 17, 18, 19, 20, 21 or 22. An immunogenic polypeptide of the invention can also be a fragment of a polypeptide that has an amino acid sequence shown in SEQ ID NOs: 2, 4, 6, 8, 10, 12, 14, 15, 16, 17, 18, 19, 20, 21 or 22. An immunogenic polypeptide fragment of the invention can be about 6, 10, 20, 30, 40, 50, 60, 70, 80, 90, 100, 250, 500, 750 amino acids in length.

Antibodies specific for $E.$ $canis$ can be detected in biological fluids or tissues by any method known in the art. The simplest methods generally are immunoassay methods. One such method is a competition-based method wherein serum samples are preincubated with an $E.$ $canis$ antigen that is not an element of an $E.$ $canis$ vaccine (e.g., an $E.$ $canis$ DIVA antigen), and then added to a solid phase, such a microtiter plate, having an immobilized monoclonal antibody specific for the $E.$ $canis$ DIVA antigen. Antibodies specific for the $E.$ $canis$ DIVA antigen in the sample will prevent the $E.$ $canis$ DIVA antigen from binding to the immobilized antibody. Detection of any binding of the $E.$ $canis$ DIVA antigen to the immobilized antibody can be determined by adding a second binding partner for the $E.$ $canis$ antigen, either directly labeled or capable of becoming labeled through binding to another binding partner having a label. A positive sample, i.e. a sample having antibodies specific for an $E.$ $canis$ DIVA antigen, is associated with a decrease in signal from the label.

In one particular embodiment, antibodies to an $E.$ $canis$ DIVA antigen in a biological sample can be detected by contacting the sample with an $E.$ $canis$ DIVA antigen and adding the sample to microtiter plate coated with an anti-DIVA antigen monoclonal antibody. Binding of the DIVA antigen to the microtiter plate can be detected by adding a rabbit polyclonal antibody against the DIVA antigen and adding an HRP-conjugated donkey anti-rabbit polyclonal antibody. Antibodies in the sample will prevent the binding of the DIVA antigen to the immobilized antibody, thereby causing a decrease in signal.

Another method for detecting antibodies specific for an $E.$ $canis$ DIVA antigen is a sandwich assay where a biological sample suspected of containing an antibody specific for an $E.$ $canis$ DIVA antigen is contacted with an immobilized $E.$ $canis$ DIVA antigen to form an immunological complex. The presence of an antibody specific for an $E.$ $canis$ DIVA antigen is determined by the detection of the binding of a labeled binding partner for the $E.$ $canis$ antibody, such as a second antibody.

In one aspect of the invention, E. canis DIVA antigens can be immobilized on a suitable solid support. A biological sample is brought into contact with the E. canis DIVA antigen, to which the anti-E. canis antibodies bind, if such antibodies are present in the sample. The binding can be detected by any suitable means, e.g., enzymes, radionuclides, particulates or fluorescent labels. In a suitable embodiment, the detection reagent can be associated with a protein that is the same or similar to that which is used to capture anti-E. canis antibodies (if present). In one particular embodiment, antibodies to E. canis can be detected by immobilizing an E. canis antigen on a solid support. Biological samples can be contacted with the solid support and, following the removal of unbound sample, binding of the E. canis antibodies to the antigen can be accomplished with, for example, a labeled IgG antibody.

DIVA antigens of the invention can also comprise mimitopes of DIVA antigens of the invention. A mimitope is a random peptide epitope that mimics a natural antigenic epitope during epitope presentation. Random peptide epitopes can be identified by generating or selecting a library of random peptide epitopes. The library is contacted with an antibody. Mimitopes are identified that are specifically immunoreactive with the antibody. Random peptide libraries can, for example, be displayed on phage or generated as combinatorial libraries.

E. canis DIVA antigens, e.g., polypeptides, can be natural, i.e., isolated from a natural source, or can be synthetic (i.e., chemically synthesized or recombinantly produced using genetic engineering techniques). Natural proteins can be isolated from the whole bacterium by conventional techniques, such as affinity chromatography. Polyclonal or monoclonal antibodies can be used to prepare a suitable affinity column by well-known techniques.

Proteins that are immunologically cross-reactive with a natural E. canis protein can be chemically synthesized. For example, polypeptides having fewer than about 100 amino acids, more usually fewer than about 80 amino acids, and typically fewer than about 50 amino acids, can be synthesized by the well-known Merrifield solid-phase synthesis method where amino acids are sequentially added to a growing chain. Merrifield, 1963, J. Am. Chem. Soc., 85:2149-2156). Recombinant proteins can also be used. These proteins can be produced by expression in cultured cells of recombinant DNA molecules encoding a desired portion of the E. canis genome. The portion of the E. canis genome can itself be natural or synthetic, with natural genes obtainable from the isolated bacterium by conventional techniques.

E. canis Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. The polynucleotides of the invention encode the polypeptides described above. In one embodiment of the invention the polynucleotides encode polypeptides shown in SEQ ID NOs:2, 4, 6, 8, 10, 12, 14, 15, 16, 17, 18, 19, 20, 21, 22 or combinations thereof. Polynucleotides of the invention include those shown in SEQ ID NO:1, 3, 5, 7, 9, 11, 13, or combinations thereof. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and staphylococcal protein A.

Polynucleotides of the invention can be isolated. An isolated polynucleotide is a polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. A nucleic acid molecule existing among hundreds to millions of other nucleic acid molecules within, for example, cDNA or genomic libraries, or gel slices containing a genomic DNA restriction digest are not to be considered an isolated polynucleotide. The complete nucleotide sequence for E. canis is available from, e.g., GenBank as accession number NCBI: NZ_AAEJ01000001.

Polynucleotides of the invention can also comprise fragments that encode immunogenic polypeptides. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 96, 98, or 99% identical to the polynucleotide sequences of the invention and the complements thereof are also polynucleotides of the invention. Percent sequence identity can be calculated as described in the "Polypeptides" section. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of E. canis polynucleotides that encode biologically functional E. canis polypeptides also are E. canis polynucleotides. Polynucleotides of the invention can be isolated from nucleic acid sequences present in, for example, a biological sample, such as blood, serum, saliva, or tissue from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide.

Polynucleotides of the invention can be used, for example, as probes or primers, for example PCR primers, to detect the presence of *E. canis* polynucleotides in a sample, such as a biological sample. The ability of such probes and primers to specifically hybridize to *E. canis* polynucleotide sequences will enable them to be of use in detecting the presence of complementary sequences in a given sample. Polynucleotide probes and primers of the invention can hybridize to complementary sequences in a sample such as a biological sample, including saliva, sputum, blood, urine, feces, cerebrospinal fluid, amniotic fluid, wound exudate, or tissue. Polynucleotides from the sample can be, for example, subjected to gel electrophoresis or other size separation techniques or can be immobilized without size separation. The polynucleotide probes or primers can be labeled. Suitable labels, and methods for labeling probes and primers are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9M salt, at temperatures ranging from about 20° C. to about 55° C. The presence of a hybridized complex comprising the probe or primer and a complementary polynucleotide from the test sample indicates the presence of *E. canis* or an *E. canis* polynucleotide sequence in the sample.

Antibodies

Antibodies of the invention are antibody molecules that specifically and stably bind to an *E. canis* polypeptide of the invention or fragment thereof. An antibody of the invention can be a polyclonal antibody, a monoclonal antibody, a single chain antibody (scFv), or a fragment of an antibody. Fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds" or "specific for" refers to a binding reaction that is determinative of the presence of an antigen in a heterogeneous population of antigens. Antibodies specifically bind to a particular antigen at least two times greater than to the background and more typically more than 10 to 100 times the background. Binding specifically can be tested using, for example, an enzyme-linked immunosorbant assay (ELISA), a radioimmunoassay (RIA), or a western blot assay using methodology well known in the art.

Additionally, monoclonal antibodies directed against epitopes present on a antigen, e.g., a polypeptide of the invention, can also be readily produced. For example, normal B cells from a mammal, such as a mouse, which was immunized with a polypeptide of the invention can be fused with, for example, HAT-sensitive mouse myeloma cells to produce hybridomas. Hybridomas producing *E. canis*-specific antibodies can be identified using RIA or ELISA and isolated by cloning in semi-solid agar or by limiting dilution. Clones producing *E. canis*-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., *P.N.A.S. U.S.A.* 82:8653 1985; Spria et al., *J. Immunolog. Meth.* 74:307, 1984. Monoclonal antibodies of the invention can also be recombinant monoclonal antibodies. See, e.g., U.S. Pat. No. 4,474,893; U.S. Pat. No. 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., *Nature* 321:522 (1986); Reichmann et al., Nature 332:323 (1988); Presta, *Curr. Op. Struct. Biol.* 2:593 (1992)), or human antibodies. Human antibodies can be made by, for example, direct immortilization, phage display, transgenic mice, or a Trimera methodology, see e.g., Reisener et al., *Trends Biotechnol.* 16:242-246 (1998).

Antibodies that specifically bind *E. canis* antigens (e.g., *E. canis* polypeptides shown in SEQ ID NO:2, 4, 6, 8, 10, 12, 14, 15, 16, 17, 18, 19, 20, 21, 22), are particularly useful for detecting the presence of *E. canis* or *E. canis* antigens in a sample, such as a serum, blood, urine or saliva sample from an *E. canis*-infected animal such as a human or dog. An immunoassay for *E. canis* or an *E. canis* antigen can utilize one antibody or several antibodies. An immunoassay for *E. canis* or an *E. canis* antigen can use, for example, a monoclonal antibody directed towards an *E. canis* epitope, a combination of monoclonal antibodies directed towards epitopes of one *E. canis* polypeptide, monoclonal antibodies directed towards epitopes of different *E. canis* polypeptides, polyclonal antibodies directed towards the same *E. canis* antigen, polyclonal antibodies directed towards different *E. canis* antigens, or a combination of monoclonal and polyclonal antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels.

Antibodies of the invention or fragments thereof can be bound to a support and used to detect the presence of *E. canis* or an *E. canis* antigen, e.g., an *E. canis* DIVA antigen or *E. canis* non-DIVA antigen. Supports include, for example, glass, polystyrene, polypropylene, polyethylene, dextran, nylon, amylases, natural and modified celluloses, polyacrylamides, agaroses and magletite.

Antibodies of the invention can further be used to isolate *E. canis* organisms or *E. canis* antigens by immunoaffinity columns. The antibodies can be affixed to a solid support by, for example, adsorbtion or by covalent linkage so that the antibodies retain their immunoselective activity. Optionally, spacer groups can be included so that the antigen binding site of the antibody remains accessible. The immobilized antibodies can then be used to bind *E. canis* organisms or *E. canis* antigens from a sample, such as a biological sample including saliva, serum, sputum, blood, urine, feces, cerebrospinal fluid, amniotic fluid, wound exudate, or tissue. The bound *E. canis* organisms or *E. canis* antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease caused by *E. canis*. By measuring the increase or decrease of *E. canis* antibodies to *E. canis* antigens in a test sample from an animal, it can be determined whether a particular therapeutic regiment aimed at ameliorating the disorder is effective. Antibodies can be detected and/or quantified using for example, direct binding assays such as RIA, ELISA, or western blot assays.

Detection

Methods of the invention can be accomplished using, for example, immunoassay techniques well known to those of skill in the art, including, but not limited to, using microplates and lateral flow devices. In one embodiment, one or more *E. canis* DIVA antigens are immobilized on a solid support at a distinct location. Detection of antigen-antibody complexes on the solid support can be by any means known in the art. For example, U.S. Pat. No. 5,726,010, which is incorporated herein by reference in its entirety, describes an example of a lateral flow device useful in the present invention. The device of the invention can be used to detect one or more antibodies to *E. canis* antigens.

Immobilization of one or more analyte capture reagents, e.g., *E. canis* polypeptides, onto a device or solid support is performed so that an analyte capture reagent will not be washed away by the sample, diluent and/or wash procedures. One or more analyte capture reagents can be attached to a surface by physical adsorption (i.e., without the use of chemical linkers) or by chemical binding (i.e., with the use of chemical linkers). Chemical binding can generate stronger attachment of capture reagents on a surface and provide defined orientation and conformation of the surface-bound molecules.

Another embodiment of the invention provides a device that is suitable for a lateral flow assay. For example, a test sample is added to a flow matrix at a first region (a sample application zone). The test sample is carried in a fluid flow path by capillary action to a second region of the flow matrix where a label capable of binding and forming a first complex with an analyte in the test sample. The first complex is carried to a third region of the flow matrix where an *E. canis* polypeptide is immobilized at a distinct location. A second complex is formed between an immobilized polypeptide and the first complex including the antibody from the sample. For example, a first complex comprising a gold sol particle and an *E. canis* polypeptide bound to an *E. canis* antibody will specifically bind and form a second complex with a second immobilized *E. canis* polypeptide or with a second antibody directed to *E. canis* antibodies. The label that is part of the second complex can be directly visualized.

In another aspect, the invention includes one or more labeled specific binding reagents that can be mixed with a test sample prior to application to a device of the invention. In this case it is not necessary to have labeled specific binding reagents deposited and dried on a specific binding reagent pad in the device. A labeled specific binding reagent, whether added to a test sample or pre-deposited on the device, can be for example, a labeled antibody that specifically binds an antibody for *E. canis*.

Any or all of the above embodiments can be provided as a kit. In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

An *E. canis* DIVA antigen, e.g., a polypeptide, can be an immobilized analyte capture reagent in a reaction zone (solid phase). A second analyte capture reagent, e.g. an anti-IgG or anti-IgM antibody, that has been conjugated to a label, can either be added to the sample before the sample is added to the device, or the second analyte capture reagent can be incorporated into the device. For example the labeled specific binding reagent can be deposited and dried on a fluid flow path that provides fluid communication between the sample application zone and the solid phase. Contact of the labeled specific binding reagent with the fluid sample results in dissolution of the labeled specific binding reagent.

The device can also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

Methods of Treatment, Amelioration, or Prevention of a Disease Caused by *E. canis*

In one embodiment of the invention, a DIVA polypeptide, polynucleotide or antibody of the invention can be used to treat, ameliorate, or prevent a disease caused by *E. canis*. If, however, a DIVA polypeptide is used to treat, ameliorate, or prevent a disease caused by *E. canis*, it could not, thereafter, be used as a DIVA polypeptide for the detection and differentiation of infected, non-vaccinated, and vaccinated animals because a vaccinated animal's immune system would recognize the DIVA antigen used for vaccination. However, a DIVA polypeptide that does not cross-react with antibodies to the DIVA polypeptide used for treatment, amelioration or prevention of a disease caused by *E. canis* may still be used as an *E. canis* DIVA antigen.

For example, if SEQ ID NO:2 or a fragment thereof is used as a vaccine, then SEQ ID NOs:4, 6, 8, 10, 12, 14, 15, 16, 17, 18, 19, 20, 21, 22 or combinations thereof can be used as a DIVA polypeptide, if they do not cross-react with antibodies specific for SEQ ID NO:2. Therefore, the DIVA polypeptides, polynucleotides, and antibodies can be used in two different ways: (1) as compositions for the prevention, treatment, or amelioration of a disease or infection caused by *E. canis*; and (2) as an *E. canis* DIVA antigen for the detection and differentiation of animals that are vaccinated; non-vaccinated; infected or not infected with *E. canis*.

Polypeptides, polynucleotides, and antibodies of the invention can be used to treat, ameliorate, or prevent a disease caused by *E. canis*. For example, an antibody, such as a monoclonal antibody of the invention or fragments thereof, can be administered to an animal, such as a human. In one embodiment of the invention an antibody or fragment thereof is administered to an animal in a pharmaceutical composition comprising a pharmaceutically acceptable carrier. A pharmaceutical composition comprises a therapeutically effective amount of an antibody or fragments thereof. A therapeutically effective amount is an amount effective in alleviating the symptoms of *E. canis* infection or in reducing the amount of *E. canis* organisms in a subject.

Polypeptides or polynucleotides of the invention can be present in an immunogenic composition and used to elicit an immune response in a host. An immunogenic composition is capable of inducing an immune response in an animal. An immunogenic polypeptide or polynucleotide composition of the invention is particularly useful in sensitizing an immune system of an animal such that, as one result, an immune response is produced that ameliorates or prevents the effect of *E. canis* infection. The elicitation of an immune response in animal model can be useful to determine, for example, optimal doses or administration routes. Elicitation of an immune response can also be used to treat, prevent, or ameliorate a disease or infection caused by *E. canis*. An immune response includes humoral immune responses or cell mediated immune responses, or a combination thereof. An immune response can also comprise the promotion of a generalized host response, e.g., by promoting the production of defensins.

The generation of an antibody titer by an animal against *E. canis* can be important in protection from infection and clearance of infection. Detection and/or quantification of antibody titers after delivery of a polypeptide or polynucleotide can be used to identify epitopes that are particularly effective at eliciting antibody titers. Epitopes responsible for a strong antibody response to *E. canis* can be identified by eliciting antibodies directed against *E. canis* polypeptides of different lengths. Antibodies elicited by a particular polypeptide epitope can then be tested using, for example, an ELISA assay to determine which polypeptides contain epitopes that are most effective at generating a strong response. Polypeptides or fusion proteins that contain these epitopes or polynucleotides encoding the epitopes can then be constructed and used to elicit a strong antibody response.

A polypeptide, polynucleotide, or antibody of the invention can be administered to a mammal, such as a mouse, rabbit, guinea pig, macaque, baboon, chimpanzee, human, cow, sheep, pig, horse, dog, cat, or to animals such as chickens or ducks, to elicit antibodies in vivo. Injection of a polynucleotide has the practical advantages of simplicity of construction and modification. Further, injection of a polynucleotide results in the synthesis of a polypeptide in the host. Thus, the polypeptide is presented to the host immune system with native post-translational modifications, structure, and conformation. A polynucleotide can be delivered to a subject as "naked DNA."

Administration of a polynucleotide, polypeptide, or antibody can be by any means known in the art, including intramuscular, intravenous, intrapulmonary, intramuscular, intradermal, intraperitoneal, or subcutaneous injection, aerosol, intranasal, infusion pump, suppository, mucosal, topical, and oral, including injection using a biological ballistic gun ("gene gun"). A polynucleotide, polypeptide, or antibody can be accompanied by a protein carrier for oral administration. A combination of administration methods can also be used to elicit an immune response. Antibodies can be administered at a daily dose of about 0.5 mg to about 200 mg. In one embodiment of the invention antibodies are administered at a daily dose of about 20 to about 100 mg.

Pharmaceutically acceptable carriers and diluents for therapeutic use are well known in the art and are described in, for example, Remington's Pharmaceutical Sciences, Mack Publishing Co. (A. R. Gennaro ed. (1985)). The carrier should not itself induce the production of antibodies harmful to the host. Such carriers include, but are not limited to, large, slowly metabolized, macromolecules, such as proteins, polysaccharides such as latex functionalized SEPHAROSE®, agarose, cellulose, cellulose beads and the like, polylactic acids, polyglycolic acids, polymeric amino acids such as polyglutamic acid, polylysine, and the like, amino acid copolymers, peptoids, lipitoids, and inactive, avirulent virus particles or bacterial cells. Liposomes, hydrogels, cyclodextrins, biodegradable nanocapsules, and bioadhesives can also be used as a carrier for a composition of the invention.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, phosphate buffered saline, Ringer's solution, Hank's solution, glucose, glycerol, dextrose, malodextrin, ethanol, or the like, singly or in combination, as well as substances such as wetting agents, emulsifying agents, tonicity adjusting agents, detergent, or pH buffering agents. Additional active agents, such as bacteriocidal agents can also be used.

If desired, co-stimulatory molecules, which improve immunogen presentation to lymphocytes, such as B7-1 or B7-2, or cytokines such as MIP1α, GM-CSF, IL-2, and IL-12, can be included in a composition of the invention. Optionally, adjuvants can also be included in a composition. Adjuvants are substances that can be used to nonspecifically augment a specific immune response. Generally, an adjuvant and a polypeptide of the invention are mixed prior to presentation to the immune system, or presented separately, but are presented into the same site of the animal. Adjuvants can include, for example, oil adjuvants (e.g. Freund's complete and incomplete adjuvants) mineral salts (e.g. $Alk(SO_4)_2$; $AlNa(SO_4)_2$, $AlNH_4(SO_4)$, Silica, Alum, $Al(OH)_3$, and $Ca_3(PO_4)_2$), polynucleotides (i.e. Polyic and Poly AU acids), and certain natural substances (e.g. wax D from *Mycobacterium tuberculosis*, as well as substances found in *Corynebacterium parvum*, *Bordetella pertussis* and members of the genus *Brucella*. Adjuvants which can be used include, but are not limited to MF59-0, aluminum hydroxide, N-acetyl-muramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN® (polysorbate) 80 emulsion.

The compositions of the invention can be formulated into ingestible tablets, buccal tablets, troches, capsules, elixirs, suspensions, syrups, wafers, injectable formulations, mouthwashes, dentrifices, and the like. The percentage of one or more polypeptides, polynucleotides, or antibodies of the invention in such compositions and preparations can vary from 0.1% to 60% of the weight of the unit.

Administration of polypeptides, polynucleotides, or antibodies can elicit an immune response in the animal that lasts for at least 1 week, 1 month, 3 months, 6 months, 1 year, or longer. Optionally, an immune response can be maintained in an animal by providing one or more booster injections of the polypeptide, polynucleotide, or antibodies at 1 month, 3 months, 6 months, 1 year, or more after the primary injection. If desired, co-stimulatory molecules or adjuvants can also be provided before, after, or together with the compositions.

A composition of the invention comprising a polypeptide, polynucleotide, antibody, or a combination thereof is administered in a manner compatible with the particular composition used and in an amount that is effective to elicit an immune response as detected by, for example, an ELISA. A polynucleotide can be injected intramuscularly to a mammal, such as a baboon, chimpanzee, dog, or human, at a dose of 1 ng/kg, 10 ng/kg, 100 ng/kg, 1000 ng/kg, 0.001 mg/kg, 0.1 mg/kg, or 0.5 mg/kg. A polypeptide or antibody can be injected intramuscularly to a mammal at a dose of 0.01, 0.05, 0.5, 0.75, 1.0, 1.5, 2.0, 2.5, 5 or 10 mg/kg.

Polypeptides, polynucleotides, or antibodies, or a combination thereof can be administered either to an animal that is not infected with *E. canis* or can be administered to an *E. canis*-infected animal. The particular dosages of polynucleotide, polypeptides, or antibodies in a composition will depend on many factors including, but not limited to the species, age, gender, concurrent medication, general condition of the mammal to which the composition is administered, and the mode of administration of the composition. An effective amount of the composition of the invention can be readily determined using only routine experimentation.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Preparation of Formalin Killed *E. Canis* for Immunization into Dogs

*E. canis* was grown in canine cell culture using methods described in the literature. See e.g., Breitschwerdt, Antimicrobial Agents and Chemotherapy, 1998, Vol 42:362-368. Using light microscopy, 030 cells were estimated to be greater than 80% infected by *E. canis*. Two liters of *E. canis* infected cell culture were collected, centrifuged and the pellet retained yielding 7.31 gms of material (wet weight). It is presumed water made up 80% of the weight of the material, giving an estimated dry weight of 1.462 gms (20% of the weight of the material). The cell pellet was resuspended to 20 mg/ml in PBS (dry weight) for a total volume of 73 ml.

To this resuspended cell pellet, 0.73 ml of formalin solution was added (Sigma Catalog HT50-1-2 Formalin Solution 10%, neutral buffered) for a final formaldehyde concentration of 0.04%. The solution was stirred overnight at 4° C. The inactivated mixture was centrifuged and the cell pellet retained. The pellet was washed by resuspension into 250 mls of PBS. The material was collected by centrifugation and the wash was repeated one time.

The washed cell pellet was resuspended into 73 mls of PBS. The sample was aliquoted to 73 screw cap vials and frozen at −80° C. Each vial contains 20 mgs (dry weight) of formalin inactivated E. canis cell culture, suitable for combining with the appropriate adjuvant for immunization into animals.

Example 2

Preparation of Formalin Fixed E. canis with Two Different Adjuvants, Protocol for the Immunization of Beagles with E. canis Antigen, and Testing of Sera from Immunized Beagles Using SNAP® 3Dx® Reversible Flow Chromatographic Assay The preparation of antigen with aluminum hydroxide adjuvant is a technique well known to those skilled in the art. For example see "Antibodies, A Laboratory Manual", Cold Spring Harbor Press, 1988, pp 99.

For immunization into dogs (laboratory beagles), two sets of doses were prepared with aluminum hydroxide adjuvant prepared as described above and two sets of doses were prepared with Ribi adjuvant (Corixa Corp., Seattle Wash.) using the protocol described by the manufacturer. Each dose contained approximately 20 mg of formalin inactivated E. canis cell culture (dry weight).

Kennel kept laboratory beagles were selected for immunization with the E. canis formalin inactivated antigen. Two groups of two dogs each; with each group using a different adjuvant were dosed with the formalin fixed E. canis preparation (aluminum oxide or Ribi). On day 0 all 4 dogs were found to be sero-negative using both the SNAP® 3Dx® reversible flow chromatographic assay diagnostic as well as Western blot analysis using E. canis organism.

The IACUC committee of Covance Research Products Inc. approved the protocol for immunization of laboratory beagles. Dogs were challenged on days 0, 28 and 56 with weekly 1 ml bleeds being monitored using SNAP® 3Dx® reversible flow chromatographic assay. All dogs were dosed with the appropriate test article subcutaneously in the dorsoscapular area. All four animals seroconverted to a positive test on SNAP®3Dx® reversible flow chromatographic assay (E. canis) by day 42. Production bleeds were taken on days 42 and 70 (approximately 50 ml blood that yielded approximately 25 ml sera).

FIG. 1 shows SNAP®3Dx® reversible flow chromatographic assay evaluation of laboratory beagles. The SNAP® reversible flow chromatographic assay device was used as described by manufacturer. "Pre" sample is from day 0. "Post" sample is from day 42. The E. canis positive spot becomes positive in all 4 dogs for the day 42 sample. Similar results were observed for the day 70 sample.

Experiments with a third vaccine comprising a third adjuvant, BCG, (Calbiochem of EMD Biosciences, Inc. San Diego, Calif.) revealed similar results. Preparation of the third vaccine was identical to the preparations described for the Ribi adjuvante vaccine described above except: 1) formalin inactivation was for 24 hrs at 4 C, and 2) 1 mg of BCG was added. The vaccination schedule was day 0, day 14, with weekly bleeds assayed for reactivity with E. canis proteins.

Example 3

Enrichment of E. canis from Cell Culture Using PERCOLL® (Colloidal Silica Coated with Polyvinylpyrrolidone) Gradients For DNA isolation and Western blot analysis, E. canis was enriched from cell culture using PERCOLL® (colloidal silica coated with polyvinylpyrrolidone) density gradients. The process of isolating intracellular pathogens from cell culture, such as Ehrlichia, is a technique well known to those skilled in the art. For example, see Akira et al. (1982) Purification of *Rickettsia tsutsugamushi* by PERCOLL® (colloidal silica coated with polyvinylpyrrolidone)density gradient centrifugation, Microbiol. Immunol., 26:321-328.

A typical *E. canis* enrichment began with 1.5 liters of infected cell culture (see above). The cells were centrifuged 6,000×g, the cell pellet retained and the supernatant discarded. The cell pellet was resuspended into 20 ml of PBS that was followed by a second centrifugation. The supernatant was discarded and supernatant retained. The pellet was then resuspended into 20 ml of PBS, sonicated for 5 seconds at 20 kHz, power setting 1.5 using a Branson sonicator. The sample was then centrifuged at 500×g for 5 minutes to pellet large debris.

PERCOLL® (colloidal silica coated with polyvinylpyrrolidone) was added to the supernatant to a final concentration of 32% (4.5 ml of PERCOLL® (colloidal silica coated with polyvinylpyrrolidone) with 10 ml of sample). The sample was loaded into Oak Ridge tubes compatible with a 70.1 Ti ultracentrifuge rotor, and centrifuged for 30 minutes at 63,000×g. The opaque band was collected using a Pasteur pipette. The opaque band is highly enriched for *Ehrlichia* (confirmed using light microscopy of the collected sample). After a 1:4 dilution with PBS, the sample was aliquoted and centrifuged at 12,000×g. The supernatant was discarded and the *Ehrlichia* pellet stored at −80° C.

Example 4

Testing of Sera or Plasma from Challenged and Infected Dogs by Western Blot

The use of 1-dimensional SDS-PAGE gel analysis and 2-dimensional gel analysis ($1^{st}$ dimension isoelectric focusing, $2^{nd}$ dimension SDS-PAGE) is well known to those skilled in the art. For example see Current Protocols in Molecular Biology, eds. F. M. Ausubel et al., John Wiley & Sons Inc., 1997, pages 10.2.2-10.3.11. The use of Western blots to analyze proteins separated using these methods are well known to those skilled in the art. For example see Current Protocols in Molecular Biology, eds. F. M. Ausubel et. al., John Wiley & Sons Inc., 1997, pages 10.8.1-10.8.116.

Initial work was performed using Western analysis of proteins separated with 1D gels (data not shown), followed by Western analysis of proteins separated using 2D gels. Proteins from whole *E. canis* harvested from cell culture were analyzed using 2D gel electrophoresis (materials and reagents used as described by the manufacturer; Bio-Rad Life Sciences Research, Hercules, Calif. 94547). The amount of sample to load per gel was determined empirically (see FIG. 2). The proteins were blotted to nitrocellulose and probed using canine sera from laboratory beagles at day 0, dogs challenged with formalin fixed *E. canis* antigen (see above), or sera from animals infected with *E. canis* (see FIGS. 3, 4 & 5).

Positive canine sera and plasma was isolated from dogs infected with *E. canis*. *E. canis* infection was verified by Western analysis of lymphocytes harvested from whole blood from these dogs, and confirmed by use of the IDEXX SNAP®3Dx® reversible flow chromatographic assay with canine sera or plasma (commercially available from IDEXX Laboratories Inc., used as described by the manufacturer).

For Western blot analysis proteins were separated using 1D SDS-PAGE or 2D isoelectric focusing/SDS-PAGE gels followed by electro-blotting of the proteins from the gels to nitrocellulose. The nitrocellulose blots were incubated in a blocking solution of 2.5% non fat dry milk dissolved into Tris buffered saline (pH 7.5), 0.05% TWEEN® (polysorbate) 20. Canine sera or plasma was diluted to the titer as described into buffer containing an *E. coli* lysate to block non-specific binding with 30% normal calf sera and incubated for 2 hrs at room temperature or over night at 4° C. After washing 3 times in TBS-TWEEN® (polysorbate) (0.05%), the blots were transferred to a buffer containing 50% fetal calf sera, 50% TBS-TWEEN® (polysorbate)-Kathon (0.05% & 0.5% respectively) to prevent nonspecific binding of a rabbit anti-canine Fc polyclonal antibody conjugated to horseradish peroxidase (Jackson Immuno Research, West Grove, Pa. 19390). The rabbit anti-canine Fc polyclonal antibody conjugate was diluted 1:5,000. The gels were washed 3 times with TBS TWEEN® (polysorbate) (0.05%), one time with TBS, and the presence of HRP detected using ECL Western Blotting Detection Reagents (Amersham Biosciences, Piscataway, N.J. 08855-1327) used as described by manufacturer. Digital images of exposed X-ray film were captured using a GelDoc 2000 (Bio-Rad Inc.).

Example 5

Isolation of DNA from *E. canis* and Construction of a Lambda Expression Library and Screening of the *E. canis* Lambda Expression Library for Clones Having DIVA Activity The preparation and screening of lambda expression libraries is a technique well known to those skilled in the art. For example, see Current Protocols in Molecular Biology, eds. F. M. Ausubel et al., John Wiley & Sons Inc., 1997, pages 5.1 through 5.8.6. For the construction of the expression library, genomic DNA was purified from *E. canis* isolated from cell culture by PERCOLL® (colloidal silica coated with polyvinylpyrrolidone) gradient centrifugation (see above). DNA was purified using a genomic DNA purification kit from Qiagen Sciences (Germantown, Md.). A Lambda ZAP® II predigested EcoRI/CIAP Vector Kit (Stratagene Corp., La Jolla, Calif. 92037) was used as specified by the manufacturer for construction of the library. *E. canis* genomic DNA was partially digested with TSP509 and fragments ranging from 2-6 kb were isolated using agarose gel electrophoresis and ligated into the lambda vector. Phage were packaged and grown as specified by the manufacturer.

Approximately 120,000 individual lambda plaques were screened for binding to sera isolated from dogs identified as positive for infection with *E. canis*, but negative for reactivity with sera from animals challenged with an *E. canis* grown in cell culture (see above). From the initial screen 84 individual plaques were identified as having this activity.

Lambda plaques were subjected to two rounds of plaque purification and retested to verify positive reactivity with sera from *E. canis* infected animals, negative reactivity when screened with sera from challenged animals.

Isolated lambda plaques were screened for cross reactivity with sera from animals identified as being seropositive for *Anaplasma phagocytophilia*, *Borrelia burgdorferi* (causative agent of Lyme disease), *Rickettsia rickettsii* (causative agent of Rocky Mountain Spotted Fever), *Leptospira interrogans* and *Dirofilaria immitis* (causative agent of canine heartworm).

At the end of the screening process, 43 lambda plaques were found to react with sera from animals infected with *E. canis* that did not react with challenge sera or sera from dogs infected with other canine pathogens (see above).

Using the ZAP® feature of the cloning vector as per the manufacturers instructions, inserts into the lambda vector were converted to plasmids. The plasmids were transformed into the *E. coli* strain, XL-1 blue for protein expression and analysis of encoded proteins by Western blot. The ends of the *E. canis* DNA inserts were subjected to DNA sequence analysis using T7 and T3 sequencing primers.

Sequence information from both the T7 and T3 reactions for all 43 clones was submitted for BLAST analysis to the NCBI website. Results were tabulated in an excel format. Based on sequence identity between the clone and the available shotgun genome sequence for *E. canis* (NCBI: NZ_AAEJ01000001), segments of genomic DNA for each clone were identified. Individual clones sharing common genes were grouped for further analysis by Western blot using pools of infected and bacterial-challenged canine sera. Based on similar banding patterns, duplicate clones were eliminated. Any clones showing reactivity to both sets of sera were eliminated. As a result of this analysis, 23 clones were selected for further evaluation. The grouping of the clones and the common antigen per group is shown in Table 1.

TABLE 1

| Common Antigen | Clone Number(s) |
| --- | --- |
| 120 kDa Antigen | 2, 10, 17, 33, 35, 79 |
| Heat Shock Proteins | 4, 9, 24, 66 |
| ATPase | 7, 84 |
| Ribosomal Protein L1 | 21, 47, 65 |
| 200 kDa Antigen | 26, 55, 76 |
| Hypothetical Protein | 75 |
| Pyruvate Dehydrogenase | 5 |
| Ribosomal Protein (50S) | 6 |
| Unknown | 57 |
| Transcriptional Regulator | 82 |

Example 6

Western Blot Analysis Using Individual *E. canis* Positive Canine Serum Samples

All 23 clones were analyzed on individual SDS-PAGE gels. Each gel was transferred to nitrocellulose and subjected to Western blotting using individual samples of canine sera from dogs that were only positive for *E. canis* infections by ELISA/SNAP® (reversible flow chromatographic assay) testing. Canine serum was diluted 1:500 in the same diluent described in Example 4 containing *E. coli* lysate and reactivity was detected using standard colorometric horseradish peroxidase techniques (Opti-4CN, Bio-Rad). A total of thirteen individual canine serum samples were evaluated. Blots were compared across samples to determine the number of dogs showing reactivity to a predominant band or set of bands per clone. The results are summarized in Table 2 and FIG. 6 (clones listed in bold are depicted in the figure).

TABLE 2

| Common Antigen | Clone Number(s) | Positive Reactors |
|---|---|---|
| 120 kDa Antigen | 2, 10, 17, 33, 35 | 13/13 |
| Heat Shock Proteins | 9 | 12/13 |
| ATPase | 7, 84 | 12/13 |
| Ribosomal Protein L1 | 21, 47, 65 | 12/13 |
| 200 kDa Antigen | 26, 55, 76 | 12/13 |

All 23 clones were also analyzed by Western blot using pooled canine sera that had tested positive for other vector-borne infectious diseases. Samples testing positive by ELISA or SNAP® reversible flow chromatographic assay for the following single infections were evaluated: Heartworm, Lyme, *Anaplasma phagocytophilum*, or *E. ewingii*. None of the clones identified in the table above showed cross-reactivity with positive canine sera for these other vector-borne infections.

Example 7

Identification of Relevant Gene Segments Encoding *E. canis* DIVA Antigens a. 120 kDa Antigen This antigen was previously described by Yu et al. (J Clin Microbiol. 2000 January; 38(1):369-74; see also, McBride et al., 2000 Infec. Immun. 68:13) and shown to be useful in the diagnosis of *E. canis* infections in dogs. This antigen has been described as both "p120" and "p140" *E. canis* antigen. See, id. Yu et al. explains that a recombinant protein expressed by the p120 gene has a molecular size of 140 kDa on a sodium dodecyl sulfate gel, which is larger than the predicted molecular mass of the protein. See, Yu et al., page 373. The Walker group (Yu et al., and McBride et al.) refer to the protein both as *E. canis* p120 and p140. Therefore, this disclosure uses both p120 and p140 interchangeably to describe this protein. The accession number for the *E. canis* p120/140 gene is AF112369 and the associated protein is AAD34330. See also, accession no. YP302666. Clones 2, 10, 17, and 33 contain full-length segments of the 120 kDa antigen gene. Clone 35 may contain a truncation of this gene. (See, SEQ ID NOs:1 and 2).

This gene was amplified from *E. canis* genomic DNA and subcloned into a pET expression system with a 6-His tag according to the manufacturer's instructions (Invitrogen). Sequencing results of this plasmid exactly matched the gene sequence encoding the protein shown in SEQ NO:ID 2, from amino acids 58 to 589. Protein lysates from BL21 bacteria induced to express this protein were analyzed by Western blotting with infected canine sera and compared to Western blots probed with sera from animals challenged with culture-adapted organisms. Consistent with previous findings, only sera from infected dogs recognized this protein of the expected molecular weight (data not shown).

P120 has a 36 amino acid motif that is repeated 14 times. See, SEQ ID NO:15. The repeated portion (underlined region in SEQ ID NO:15 is a 60 kD peptide). SEQ ID NO:16 shows the aligned 14 repeats. SEQ ID NO:17 shows the consensus sequence of the 14 repeats.

One embodiment of the invention provides a polypeptide comprising:

(SEQ ID NO: 17)
KEEX$_1$TPEVX$_2$AEDLQPAVDX$_3$SX$_4$EHSSSEVGX$_5$KVSX$_6$TS.

Where
X$_1$=S or N
X$_2$=K or R
X$_3$=G, D, or S
X$_4$=V or I
X$_5$=E or K
X$_6$=E or K Another embodiment of the invention provides a multimeric polypeptide where SEQ ID NO:17 is repeated two or more times. The multimeric polypeptide can also comprise one or more heterologous polypeptides.

In another embodiment, the invention provides a polypeptide of SEQ ID NO:21, XPEVKAEDLQPAVDGSVEHX, wherein each of the X's=0, 1, 2, 3, 4, 5, 6, 7, 8, 9, 10, 11, 12, 13, 14, or 15 amino acids.

In another embodiment, the invention provides a polypeptide of SEQ ID NO:22, CKEESTPEVKAEDLQPAVDGS-VEHSSSEVGXKVSETS; wherein X=K or E.

b. 200 kDa Antigen

This antigen was previously described by McBride et al. (J Clin Microbiol. 2001 January; 39(1):315-22) and shown to be useful in the diagnosis of ehrlichiosis. The accession number for this gene is AF252298 and associated protein AAK01145. A portion of this protein sequence is associated with a published patent (SEQ ID NO:2 of U.S. Pat. No. 6,355,777, accession number AAE96254). We have identified a different region of this protein that serves as diagnostic antigen for ehrlichiosis and a DIVA reagent. The portion of the gene spans from nucleotide 1081 of AF252298 through to the end, nucleotide 4266. (See SEQ ID NOs:3 and 4).

This gene was amplified from *E. canis* genomic DNA and subcloned into a pET expression system with a 6-His tag according to the manufacturer's instructions (Invitrogen). Sequencing results of this plasmid exactly matched the gene sequence encoding the protein shown in SEQ ID NO:4, from amino acids 1 to 1061. Protein lysates from BL21 bacteria induced to express this protein were analyzed by Western blotting with infected canine sera and compared to Western blots probed with sera from animals challenged with culture-adapted organisms. Consistent with previous findings, only sera from infected dogs recognized this protein of the expected molecular weight (data not shown).

c. ATPase

This gene (Locus tag "Ecan02000699") has been predicted by automated computational analysis of the shotgun genome sequence of *E. canis*. It codes for a protein of more than 4000 amino acids (ZP_00210575). The *E. canis* DIVA screen identified two separate regions of this gene and its associated protein as potential immunodominant antigens and DIVA reagents. The segments of the protein identified in clones 84 and 7 are amino acids 1984-2774 and 2980-3740, respectively, of accession number 46308382. (See SEQ ID NOs: 5, 6, 7, 8).

Both fragments of this gene was amplified from *E. canis* genomic DNA and subcloned separately into a pET expression system with a 6-His tag according to the manufacturer's instructions (Invitrogen). Sequencing results of this plasmid exactly matched the gene sequences associated with the proteins shown SEQ ID NOs:6 and 8, from amino acids 1 to 782 and 1 to 746 respectively. Protein lysates from BL21 bacteria induced to express these proteins were analyzed by Western blotting with infected canine sera and compared to Western blots probed with sera from animals challenged with culture-adapted organisms. Consistent with previous findings, only sera from infected dogs recognized these proteins of the expected molecular weight (data not shown).

d. Heat Shock Proteins

Although this clone contained a gene for the heat shock protein, GrpE, the gene sequence coding for the immunodominant antigen arises from a hypothetical protein sequence predicted by the automated computational analysis of the genome. Based on the molecular weight and pI of the protein, the gene of interest in clone 9 is locus number "Ecan02000495" and the associated protein 46308954.

Because this protein is only predicted from the computer annotation of the genome and has not been previously identified from E. canis organisms as an immunodominant protein, this is the first evidence that this gene is expressed in E. canis and stimulates an immune response in the infected canine host. The protein will be identified as the p16 antigen (see SEQ ID NO: 9 and 10).

This gene was amplified from the pBlueScript vector containing the genomic DNA of interest and subcloned into a pET expression system with a 6-His tag according to the manufacturer's instructions (Invitrogen). Sequencing results of this plasmid exactly matched the gene sequence associated with locus number "Ecan02000495". Protein lysates from BL21 bacteria induced to express this protein were analyzed by Western blotting with infected canine sera and compared to Western blots probed with sera from animals challenged with culture-adapted organisms. Consistent with previous findings, only sera from infected dogs recognized this protein of the expected molecular weight (see FIG. 7).

e. Ribosomal Protein L1

This gene is identified by the locus tag "Ecan02000476" from the E. canis genome. The associated protein has the accession number ZP_00211130 (see SEQ ID NOs:11 and 12). The identification of this protein has been predicted based on automated computational analysis of the genome. A BLAST analysis of this protein reveals that the sequence is about 70% identical to a surface protein of E. chaffeensis (Accession number 489-4576). Immunoreactivity to the E. chaffeensis protein has previously been reported by Yu et al., (J Clin Microbiol. 1999 August; 37(8):2568-75). The E. chaffeensis protein (Accession number 489-4576) is referred to as the 106 kDa protein precursor.

f. Possible Non-120 kDa Antigens

Within the genomic fragment containing the gene for the 120 kDa antigen, other genes are present that may also be immunodominant and DIVA reagents. For instance, clone 10 produces a different banding pattern on Western blots probed with infected sera, compared to clones containing the 120 kDa antigen alone. Clone 10 contains genetic information for the VirD4 components of a Type IV secretory pathway and this gene sequence is identified by the locus tag "Ecan02000624". This gene codes for a protein of 723 amino acids (ZP_00211244), but only a portion of this protein appears to be expressed by clone 10, as determined by the molecular weight of the protein identified on the gel (see SEQ ID NOs:13 and 14).

Example 8

Evaluation of E. canis P140 Peptides

Sera from beagles immunized with formalin fixed E. canis (vaccine samples) were tested using a microtiter-plate based immunoassay prepared using synthetic peptides derived from E. canis p140 protein, (also known as p120, see Example 7).

Preparation of Formalin Fixed E. canis and immunization of beagles were described in Examples 1 and 2. Samples from immunized beagles were tested using microtiter-plate based immunoassays prepared using synthetic peptides (SEQ ID NO:18, SEQ ID NO:19 and SEQ ID NO:20) in indirect and direct assay formats.

Indirect Assay Format

Samples were tested using microtiter-plate based immunoassays prepared using the synthetic peptides (SEQ ID NO:18, SEQ ID NO:19 and SEQ ID NO:20). Individual peptides were immobilized on microtiter wells by direct adsorption. A dilution of the test sample (1:100) was added to the microtiter well and unbound antibody was removed by washing. Antibody bound to the immobilized peptide was detected by reaction with an anti-species, in this case canine, horseradish peroxidase (HRPO) conjugate (1:2000 dilution), washing and addition of a HRPO substrate. The absorbance (A650) of individual microtiter wells was determined using a microtiter plate reader.

Direct Assay Format

Individual peptides (SEQ ID NO:18, SEQ ID NO:19 and SEQ ID NO:20) were conjugated to bovine serum albumin and immobilized on microtiter wells by direct adsorption. Synthetic peptides (SEQ ID NO:18, SEQ ID NO:19 and SEQ ID NO:20) were conjugated to an indicator reagent, horseradish peroxidase (HRPO). The test sample and the immunoassay peptide/indicator were added to a microtiter well coated with the corresponding peptide, which was incubated and washed. Antibody bound to the immobilized peptide and the peptide/indicator reagent was detected by addition of an HRPO substrate reagent. The absorbance (A650) of individual microtiter wells was determined using a microtiter plate reader.

Assay results are shown in Table 3. The positive control (PC, ID 1049:16 E) and negative control (NC, 3818:57 B) were known E. canis positive and negative serum samples, respectively. All samples were tested using the commercially available SNAP® 4Dx® reversible flow chromatographic assay for E. canis antibody. Results for sequential temporal samples from 6 dogs (CVYDEH, CWMBDC, CVXCSM, CWMAXK, CVSCVA and CVXCAP) receiving the formaldehyde-treated E. canis antigen formulated using different adjuvants are shown for day 0 to day 42 post-immunization. Results of the SNAP® 4Dx® reversible flow chromatographic assay demonstrate that an antibody response was induced in the vaccinated animals. None of the serum samples from vaccinated animals was reactive in the direct assay format. Several samples (for example from dog CWMAXK) had high background reactions in the indirect assay format.

The results demonstrate that antibody induced as a result of immunization using formaldehyde fixed vaccine was significantly non-reactive to the synthetic peptides derived from an E. canis p140 protein. (SEQ ID NO:18, SEQ ID NO:19 and SEQ ID NO:20).

TABLE 3

Reaction of sera from dogs immunized with formaldehyde-treated *E. canis* antigen measured using microtiter assays prepared using peptides derived from *E. canis* p140 protein. (SEQ ID NO: 18, SEQ ID NO: 19 and SEQ ID NO: 20).

| Sample | 4Dx ® *E. canis* Result | Indirect Plate Results (A650) | | | Direct Plate Results (A650) | | |
|---|---|---|---|---|---|---|---|
| | | SEQ ID NO: 18 | SEQ ID NO: 19 | SEQ ID NO: 20 | SEQ ID NO: 18 | SEQ ID NO: 19 | SEQ ID NO: 20 |
| 1049:16E (PC) | 0.72 | 2.071 | 2.075 | 1.867 | 2.049 | 1.821 | 1.495 |
| 3818:57B (NC) | N | 0.051 | 0.058 | 0.050 | 0.034 | 0.033 | 0.035 |
| CVYDEH day 0 | N | 0.050 | 0.062 | 0.045 | 0.034 | 0.034 | 0.035 |
| day 7 | N | 0.048 | 0.052 | 0.042 | 0.033 | 0.032 | 0.036 |
| day 14 | N | 0.051 | 0.055 | 0.048 | 0.036 | 0.034 | 0.038 |
| day 21 | N | 0.044 | 0.062 | 0.051 | 0.035 | 0.034 | 0.040 |
| day 28 | 0.04 (vw+) | 0.054 | 0.073 | 0.055 | 0.036 | 0.033 | 0.034 |
| day 35 | 0.07 (vw+) | 0.049 | 0.058 | 0.047 | 0.033 | 0.035 | 0.039 |
| day 42 | N | 0.051 | 0.059 | 0.053 | 0.034 | 0.035 | 0.040 |
| CWMBDC day 0 | 0.08 | 0.054 | 0.085 | 0.082 | 0.035 | 0.033 | 0.038 |
| day 7 | 0.20 | 0.064 | 0.078 | 0.072 | 0.038 | 0.035 | 0.035 |
| day 14 | 0.30 | 0.058 | 0.081 | 0.085 | 0.038 | 0.033 | 0.040 |
| day 21 | 0.24 | 0.051 | 0.101 | 0.078 | 0.037 | 0.040 | 0.039 |
| day 28 | 0.22 | 0.049 | 0.082 | 0.073 | 0.034 | 0.036 | 0.033 |
| day 35 | 0.17 | 0.043 | 0.068 | 0.081 | 0.033 | 0.040 | 0.035 |
| day 42 | 0.11 | 0.044 | 0.071 | 0.074 | 0.031 | 0.034 | 0.031 |
| CVXCSM day 0 | N | 0.049 | 0.082 | 0.051 | 0.033 | 0.035 | 0.034 |
| day 7 | N | 0.038 | 0.076 | 0.052 | 0.034 | 0.033 | 0.037 |
| day 14 | N | 0.044 | 0.069 | 0.049 | 0.033 | 0.032 | 0.038 |
| day 21 | 0.10 (w+) | 0.038 | 0.054 | 0.045 | 0.035 | 0.035 | 0.036 |
| day 28 | 0.10 (w+) | 0.044 | 0.060 | 0.049 | 0.036 | 0.033 | 0.035 |
| day 35 | 0.08 (vw+) | 0.040 | 0.062 | 0.053 | 0.034 | 0.035 | 0.041 |
| day 42 | 0.05 (vw+) | 0.041 | 0.057 | 0.049 | 0.033 | 0.035 | 0.036 |
| CWMAXK day 0 | 0.07 (vw+) | 0.043 | 0.078 | 0.054 | 0.034 | 0.039 | 0.037 |
| day 7 | 0.41 | 0.082 | 0.475 | 0.413 | 0.034 | 0.034 | 0.045 |
| day 14 | 0.44 | 0.049 | 0.782 | 0.607 | 0.034 | 0.035 | 0.044 |
| day 21 | 0.36 | 0.092 | 0.587 | 0.440 | 0.033 | 0.037 | 0.038 |
| day 28 | 0.39 | 0.063 | 0.407 | 0.258 | 0.037 | 0.034 | 0.038 |
| day 35 | 0.41 | 0.056 | 0.286 | 0.212 | 0.036 | 0.034 | 0.037 |
| day 42 | 0.35 | 0.048 | 0.196 | 0.155 | 0.034 | 0.034 | 0.041 |
| CVSCVA day 0 | 0.10 (w+) | 0.039 | 0.084 | 0.084 | 0.033 | 0.033 | 0.038 |
| day 7 | 0.37 | 0.040 | 0.107 | 0.066 | 0.032 | 0.032 | 0.036 |
| day 14 | 0.14 | 0.053 | 0.151 | 0.062 | 0.035 | 0.033 | 0.039 |
| day 21 | 0.33 | 0.057 | 0.131 | 0.072 | 0.035 | 0.033 | 0.034 |
| day 28 | 0.29 | 0.049 | 0.104 | 0.058 | 0.035 | 0.034 | 0.036 |
| day 35 | 0.36 | 0.043 | 0.108 | 0.079 | 0.034 | 0.039 | 0.040 |
| day 42 | 0.32 | 0.047 | 0.117 | 0.044 | 0.033 | 0.036 | 0.037 |
| CVXCAP day 0 | N | 0.041 | 0.065 | 0.040 | 0.032 | 0.035 | 0.032 |
| day 7 | 0.34 | 0.058 | 0.106 | 0.068 | 0.036 | 0.033 | 0.033 |
| day 14 | 0.30 | 0.087 | 0.150 | 0.112 | 0.034 | 0.035 | 0.039 |
| day 21 | 0.35 | 0.065 | 0.120 | 0.086 | 0.039 | 0.036 | 0.041 |
| day 28 | 0.19 | 0.054 | 0.103 | 0.059 | 0.035 | 0.036 | 0.032 |
| day 35 | 0.18 | 0.046 | 0.092 | 0.047 | 0.033 | 0.033 | 0.039 |
| day 42 | 0.19 | 0.051 | 0.067 | 0.047 | 0.035 | 0.035 | 0.038 |

Example 9

Sera from known *E. canis* positive and negative dogs was tested using a microtiter-plate based immunoassay prepared using the synthetic peptides obtained from *E. canis* protein p140 protein (also known as p120, see Example 7).

*E. canis* positive and negative field samples were obtained and tested using the SNAP® 4Dx® reversible flow chromatographic assay for antibody to *E. canis*. Samples were then tested using indirect and direct microtiter plate format assays produced using synthetic peptides derived from the *E. canis* P140 protein (SEQ ID NO:18, SEQ ID NO:19 and SEQ ID NO:20).

Indirect Assay Format

Samples were tested using microtiter-plate based immunoassays prepared using the synthetic peptides (SEQ ID NO:18, SEQ ID NO:19 and SEQ ID NO:20). Individual peptides were immobilized on microtiter wells by direct adsorption. A dilution of the test sample (1:100) was added to the microtiter well and unbound antibody was removed by washing. Antibody bound to the immobilized peptide was detected by reaction with an anti-species, in this case canine, horseradish peroxidase (HRPO) conjugate (1:2000 dilution), washing and addition of a HRPO substrate. The absorbance (A650) of individual microtiter wells was determined using a microtiter plate reader.

Direct Assay Format

Individual peptides (SEQ ID NO:18, SEQ ID NO:19 and SEQ ID NO:20) were conjugated to bovine serum albumin and immobilized on microtiter wells by direct adsorption. The synthetic peptides (SEQ ID NO:18, SEQ ID NO:19 and SEQ ID NO:20) were conjugated to the indicator reagent, horseradish peroxidase (HRPO). The test sample and the immunoassay peptide/indicator were added to a microtiter well coated with the corresponding peptide, which was incubated and washed. Antibody bound to the immobilized peptide and the peptide/indicator reagent was detected by addition of an HRPO substrate reagent. The absorbance (A650) of individual microtiter wells was determined using a microtiter plate reader.

Table 4 shows results for *E. canis* positive and negative field samples tested using the indirect assay format. The positive control (PC, ID 1049:16 E) and negative control (NC, 3818:57 B) were known *E. canis* positive and negative serum samples, respectively. Samples were determined to be *E. canis* antibody positive or negative using the SNAP® 4Dx® reversible flow chromatographic assay. Assay results are shown for microtiter plate format assays made using peptide reagents (SEQ ID:18, SEQ ID:19 and SEQ ID:20).

Table 5 shows results for *E. canis* positive and negative field samples tested using the direct assay format. The positive control (PC, ID 1049:16 E) and negative control (NC, 3818:57 B) were known *E. canis* positive and negative serum samples, respectively. Samples were determined to be *E. canis* antibody positive or negative using the SNAP® 4Dx® reversible flow chromatographic assay. Assay results are shown for microtiter plate format assays made using peptide reagents (SEQ ID:18, SEQ ID:19 and SEQ ID:20).

TABLE 4

*E. canis* positive and negative field samples tested using the indirect microtiter plate format assay constructed using P140 peptides (SEQ ID NO: 18, SEQ ID NO: 19 and SEQ ID NO: 20).

| Sample | | SNAP® 4Dx®* Result | Absorbance at 650 nM | | |
|---|---|---|---|---|---|
| | | | SEQ ID No: 18 | SEQ ID NO: 19 | SEQ ID no: 20 |
| | 1049:16E (PC) | | 2.292 | 2.735 | 2.584 |
| | 3818:57B (NC) | | 0.051 | 0.065 | 0.045 |
| EC+ | HP 127 | 0.07 | 0.042 | 0.050 | 0.038 |
| EC+ | HP 143 | 0.08 | 2.867 | 2.825 | 2.731 |
| EC+ | HP 147 | 0.09 | 2.370 | 2.661 | 2.658 |
| EC+ | HP 151 | 0.21 | 2.176 | 2.093 | 2.535 |
| EC+ | HP 161 | 0.18 | 1.708 | 2.178 | 2.551 |
| EC+ | HP 165 | 0.08 | 2.690 | 2.492 | 2.525 |
| EC+ | HP 172 | 0.07 | 0.229 | 0.902 | 2.197 |
| EC+ | HP 185 | 0.38 | 2.497 | 2.622 | 2.704 |
| EC+ | HP 186 | 0.26 | 2.899 | 2.979 | 2.794 |
| EC+ | HP 188 | 0.40 | 2.482 | 2.578 | 2.898 |
| EC+ | HP 190 | 0.21 | 2.484 | 2.534 | 2.632 |
| EC+ | HP 192 | 0.18 | 1.473 | 2.132 | 2.526 |
| EC+ | HP 194 | 0.43 | 2.583 | 2.429 | 2.539 |
| EC+ | HP 197 | 0.22 | 2.150 | 2.239 | 2.537 |
| EC+ | HP 201 | 0.36 | 2.449 | 2.472 | 2.519 |
| EC+ | HP 206 | 0.10 | 2.477 | 2.247 | 2.549 |
| EC+ | HP 207 | 0.08 | 2.030 | 2.359 | 2.369 |
| EC+ | HP 209 | 0.20 | 0.262 | 0.218 | 1.102 |
| EC+ | HP 213 | 0.21 | 1.471 | 1.662 | 2.406 |
| EC+ | HP 215 | 0.19 | 2.144 | 2.431 | 2.721 |
| EC− | HP 116 | 0.02 | 0.110 | 0.065 | 0.070 |
| EC− | HP 119 | 0.02 | 0.102 | 0.091 | 0.079 |
| EC− | HP 120 | 0.01 | 0.058 | 0.063 | 0.045 |
| EC− | HP 121 | 0.02 | 0.054 | 0.064 | 0.057 |
| EC− | HP 122 | 0.03 | 0.053 | 0.059 | 0.040 |
| EC− | HP 124 | 0.02 | 0.055 | 0.061 | 0.052 |

TABLE 4-continued

*E. canis* positive and negative field samples tested using the indirect microtiter plate format assay constructed using P140 peptides (SEQ ID NO: 18, SEQ ID NO: 19 and SEQ ID NO: 20).

| Sample | | SNAP® 4Dx®* Result | Absorbance at 650 nM | | |
|---|---|---|---|---|---|
| | | | SEQ ID No: 18 | SEG ID NO: 19 | SEQ ID no: 20 |
| EC− | HP 128 | 0.02 | 0.068 | 0.072 | 0.054 |
| EC− | HP 129 | 0.02 | 0.056 | 0.057 | 0.044 |
| EC− | HP 130 | 0.01 | 0.049 | 0.048 | 0.039 |
| EC− | HP 131 | 0.01 | 0.051 | 0.053 | 0.043 |
| EC− | HP 132 | 0.03 | 0.057 | 0.061 | 0.038 |
| EC− | HP 134 | 0.02 | 0.059 | 0.084 | 0.114 |
| EC− | HP 137 | 0.03 | 0.043 | 0.046 | 0.037 |
| EC− | HP 138 | 0.01 | 0.055 | 0.063 | 0.048 |
| EC− | HP 139 | 0.01 | 0.064 | 0.062 | 0.056 |
| EC− | HP 140 | 0.00 | 1.574 | 2.444 | 2.491 |
| EC− | HP 142 | 0.02 | 0.065 | 0.068 | 0.069 |
| EC− | HP 144 | 0.02 | 0.080 | 0.079 | 0.081 |
| EC− | HP 145 | 0.01 | 1.564 | 1.934 | 2.095 |
| EC− | HP 148 | 0.01 | 0.037 | 0.043 | 0.043 |

*Reversible flow chromatographic assay

TABLE 5

*E. canis* positive and negative field samples tested using the direct microtiter plate format assay constructed using P140 peptides (SEQ ID NO: 18, SEQ ID NO: 19 and SEQ ID NO: 20).

| Sample | | 3Dx® SNAP* S-Bkg | Absorbance at 650 nM | | |
|---|---|---|---|---|---|
| | | | SEQ ID NO: 18 | SEQ ID NO: 19 | SEQ ID NO: 20 |
| 1049:16E (PC) | | 0.72 | 2.753 | 2.079 | 2.018 |
| 3818:57B (NC) | | Neg | 0.034 | 0.035 | 0.036 |
| 1049:16A | *E. canis* pos | 0.28 | 0.201 | 0.173 | 1.448 |
| 1049:16G | *E. canis* pos | 0.50 | 0.034 | 0.034 | 0.039 |
| 1049:16Q | *E. canis* pos | 0.39 | 2.308 | 1.933 | 2.151 |
| 1049:16U | *E. canis* pos | 0.56 | 0.627 | 2.038 | 2.254 |
| 1061:03B | *E. canis* pos | 0.49 | 0.083 | 0.338 | 0.889 |
| 1061:03I | *E. canis* pos | 0.27 | 2.766 | 2.593 | 1.646 |
| 1177:21D | *E. canis* pos | 0.15 | 0.042 | 0.046 | 0.126 |
| 1177:21G | *E. canis* pos | 0.41 | 1.087 | 1.675 | 1.835 |
| 1177:21K | *E. canis* pos | 0.34 | 0.681 | 1.930 | 2.010 |
| 1177:63O | *E. canis* pos | 0.41 | 0.146 | 0.112 | 1.587 |
| 1183:85A | *E. canis* pos | 0.49 | 2.768 | 2.757 | 2.476 |
| 1256:31I | *E. canis* pos | 0.23 | 0.044 | 0.086 | 0.143 |
| 813:91F | *E. canis* pos | 0.41 | 1.239 | 1.570 | 1.993 |
| 813:91I | *E. canis* pos | 0.41 | 0.212 | 0.517 | 1.646 |
| EC 10 | *E. canis* pos | 0.37 | 0.236 | 0.302 | 0.465 |

*Reversible flow chromatographic assay

The results demonstrate that antibody induced as a result of natural infection was reactive to the synthetic peptides derived from the *E. canis* p140 protein. (SEQ ID NO:18, SEQ ID NO:19 and SEQ ID NO:20).

Sequences:

```
SEQ ID NO: 1   120 kDa Antigen Nucleotide Sequence
ORIGIN
     1 ATGGATATTG ATAACAATAA TGTGACTACA TCAAGTACGC AAGATAAAAG TGGGAATTTA

61 ATGGAAGTGA TTATGCGTAT ATTAAATTTT GGTAATAATT CAGATGAGAA AGTAAGCAAT

121 GAAGACACTA AAGTTCTTGT AGAGAGTTTA CAACCTGCTG TGAATGACAA TGTAGGAAAT

181 CCATCAAGTG AAGTTGGTAA AGAAGAAAAT GCTCCTGAAG TTAAAGCGGA AGATTTGCAA

241 CCTGCTGTAG ATGGTAGTGT AGAACATTCA TCAAGTGAAG TTGGGAAAAA AGTATCTGAA
```

-continued

```
 301 ACTAGTAAAG AGGAAAGTAC TCCTGAAGTT AAAGCAGAAG ATTTGCAACC TGCTGTAGAT
 361 GGTAGTATAG AACATTCATC AAGTGAAGTT GGAGAAAAAG TATCTAAAAC TAGTAAAGAG
 421 GAAAGTACTC CTGAAGTTAA AGCAGAAGAT TTGCAACCTG CTGTAGATGA TAGTGTGGAA
 481 CATTCATCAA GTGAAGTTGG AGAAAAAGTA TCTGAAACTA GTAAAGAGGA AAATACTCCT
 541 GAAGTTAAAG CAGAAGATTT GCAACCTGCT GTAGATGGTA GTATAGAACA TTCATCAAGT
 601 GAAGTTGGAG AAAAAGTATC TAAAACTAGT AAAGAGGAAA GTACTCCTGA AGTTAAAGCA
 661 GAAGATTTGC AACCTGCTGT AGATGATAGT GTGGAACATT CATCAAGTGA AGTTGGAGAA
 721 AAAGTATCTG AAACTAGTAA AGAGGAAAAT ACTCCTGAAG TTAAAGCAGA GATTTGCAA
 781 CCTGCTGTAG ATGGTAGTGT GGAACATTCA TCAAGTGAAG TTGGAGAAAA AGTATCTAAA
 841 ACTAGTAAAG AGGAAAGTAC TCCTGAAGTT AAAGCAGAAG ATTTGCAACC TGCTGTAGAT
 901 GATAGTGTGG AACATTCATC AAGTGAAGTT GGAGAAAAAG TATCTGAAAC TAGTAAAGAG
 961 GAAAATACTC CTGAAGTTAG AGCAGAAGAT TTGCAACCTG CTGTAGATGG TAGTGTAGAA
1021 CATTCATCAA GTGAAGTTGG AGAAAAAGTA TCTGAAACTA GTAAAGAGGA AGTACTCCT
1081 GAAGTTAAAG CAGAAGATTT GCAACCTGCT GTAGATAGTA GTATAGAACA TTCATCAAGT
1141 GAAGTTGGGA AAAAGTATC TGAAACTAGT AAAGAGGAAA GTACTCCTGA AGTTAAAGCA
1201 GAAGATTTGC AACCTGCTGT AGATGGTAGT GTAGAACATT CATCAAGTGA AGTTGGAGAA
1261 AAAGTATCTG AAACTAGTAA AGAGGAAAAT ACTCCTGAAG TTAAAGCAGA GATTTGCAA
1321 CCTGCTGTAG ATGGTAGTGT AGAACATTCA TCAAGTGAAG TTGGAGAAAA AGTATCTGAA
1381 ACTAGTAAAG AGGAAAATAC TCCTGAAGTT AAAGCGGAAG ATTTGCAACC TGCTGTAGAT
1441 GGTAGTGTAG AACATTCATC AAGTGAAGTT GGAGAAAAAG TATCTGAAAC TAGTAAAGAA
1501 GAAAGTACTC CTGAAGTTAA AGCAGAAGAT TTGCAACCTG CTGTAGATGA TAGTGTAGAA
1561 CATTCATCAA GTGAAGTTGG AGAAAAAGTA TCTGAAACTA GTAAAGAAGA AGTACTCCT
1621 GAAGTTAAAG CGGAAGATTT GCAACCTGCT GTAGATGGTA GTGTGGAACA TTCATCAAGT
1681 GAAGTTGGAG AAAAAGTATC TGAGACTAGT AAAGAGGAAA GTACTCCTGA AGTTAAAGCG
1741 GAAGTACAGC CTGTTGCAGA TGGTAATCCT GTTCCTTTAA ATCCTATGCC TTCAATTGAT
1801 AATATTGATA CTAATATAAT ATTCCATTAC CATAAAGACT GTAAAAAAGG TTCAGCTGTA
1861 GGAACAGATG AAATGTGTTG TCCTGTATCA GAATTAATGG CTGGGGAACA TGTTCATATG
1921 TATGGAATTT ATGTCTATAG AGTTCAATCA GTAAAGGATT TAAGTGGTGT ATTTAATATA
1981 GATCATTCTA CATGTGATTG TAATTTAGAT GTTTATTTTG TAGGATACAA TTCTTTTACT
2041 AACAAAGAAA CAGTTGATTT AATATAA
```

SEQ ID NO: 2  120 kDa Antigen Protein Sequence
ORIGIN

```
   1 MDIDNNNVTT SSTQDKSGNL MEVIMRILNF GNNSDEKVSN EDTKVLVESL QPAVNDNVGN
  61 PSSEVGKEEN APEVKAEDLQ PAVDGSVEHS SSEVGKKVSE TSKEESTPEV KAEDLQPAVD
 121 GSIEHSSSEV GEKVSKTSKE ESTPEVKAED LQPAVDDSVE HSSSEVGEKV SETSKEENTP
 181 EVKAEDLQPA VDGSIEHSSS EVGEKVSKTS KEESTPEVKA EDLQPAVDDS VEHSSSEVGE
 241 KVSETSKEEN TPEVKAEDLQ PAVDGSVEHS SSEVGEKVSK TSKEESTPEV KAEDLQPAVD
 301 DSVEHSSSEV GEKVSETSKE ENTPEVRAED LQPAVDGSVE HSSSEVGEKV SETSKEESTP
 361 EVKAEDLQPA VDSSIEHSSS EVGKKVSETS KEESTPEVKA EDLQPAVDGS VEHSSSEVGE
 421 KVSETSKEEN TPEVKAEDLQ PAVDGSVEHS SSEVGEKVSE TSKEENTPEV KAEDLQPAVD
 481 GSVEHSSSEV GEKVSETSKE ESTPEVKAED LQPAVDDSVE HSSSEVGEKV SETSKEESTP
```

```
541 EVKAEDLQPA VDGSVEHSSS EVGEKVSETS KEESTPEVKA EVQPVADGNP VPLNPMPSID

601 NIDTNIIFHY HKDCKKGSAV GTDEMCCPVS ELMAGEHVHM YGIYVYRVQS VKDLSGVFNI

661 DHSTCDCNLD VYFVGYNSFT NKETVDLI.
```

SEQ ID NO 3   200 kDa Antigen nucleotide sequence from 1081 to end
ORIGIN
```
   1 AATTTAGAT TTTGGACTTG TAGATGGAGA TGGTAAAAAT CCTTTACATC ATGCTGTTGA

61 ACATTTGCCA CCTGTTATAC TTAAGGGCGT AATGGACCAT GTAAAAAATA GTAGTGAGTT

121 TCAAGATTTA GTAAATGATC CTGATTATTT TGGAAATACT ATAGCTCATT ATGCAGTTAA

181 GAATAAAAAT GCTGATTTAA CATTGTTTAA CATGCTGAAA GCTTCAGGAG CTGATTTAAA

241 TGTTAGGAAT GTAGTTGGTC GAGCTCCAAT ACATGTTGCT TCTTCTAATG GTAAGGCTAA

301 TGCAGTTTCT GGACTTGTAT CATGTGGTAT TGACGTTAAT TCTCAAGATG TGAATGGAGA

361 TACACCACTT CATATTGCTG TTGAAGGCGG TAGTATGGAG ACGGTATTAG CAGTGTTAAA

421 TCAGAGAGGT GCTGATGTTA GTGTCCAGAA TAACGATGGA GTTACACCTA TGCTTAGTGC

481 TGCTAAATAT GGAGATATAG GTGTAATAAA AGCTTTAGGT TCAGCTAAAC CAAATATTAA

541 AGGTGAAGAC ACTGTTGCTA AATCATTGCT GATGGAGGAT TACAAAGGTT TTACACCCTT

601 GCATTTTGTA GCTGGTGGTG GTAGCAGAGA TACATTCCGT GTCGTAAGAA AAAATTATGA

661 AAAATGTCAT GACTTAGCTA CTATTAGGGC AGCTTTAATG CAAGATAGAA GTGGTGGTGA

721 GCTTGTAAAT TTAGGGGATT TTGAAAGTGA AAATATATTG GGTTCGCCAA ATGCAAAATT

781 CTTGCAGCAT ATTCAATCAG CAAATTTTGG TTTTTCTCCA GCGCATTGTG CTATAGTATC

841 GTCTAATCAC AATGTAATGA AAGATATCTT AAATTTTGTT GGGGATTCGT TACACCTACC

901 AAGTGAGCGT GGGTATAATG CAATGCAGGT TGCTGCTTTG TTTGGTGACA AAGAAGCAGT

961 GAAAATGCTT GCTAAAAGTG CTAAGCCAAG TGATCTTAAT TTTAAGACTT CAGCAACTCC

1021 TACTCCGTTA AATCTTGCAT GTCTTAGAGG TGATAATGAG GTAGTACGTG GGTTAGTAGG

1081 TCAACATGGT ATTGACATTA ACCAACGTAT GGGAAGTGAT AAAAACACTG TATTGCATTA

1141 TGCAATCAGC AAAGGAGATA GTTTTCTTGT GCAAAAGATA TTAGCTCATA CTGGAGTTGA

1201 TGTTAATTGT GAGAATAACC TAGGTCAAAC GCCTTTACAT TTAGCAGTTG AGGGAGGAGA

1261 TCCTAAGATA GTATCTTCTC TTCTTAAAGC TGGTGCAGTA GTTAATCGTC TGGATGATAA

1321 TGGTAGATCT GTACTTTCTT CTGCGATAGT TCCAGGTAGA AAAGAAAAGG GAGTGCTGGG

1381 TATAGTTAAT AAATTGCTGG ATAGAGGTGC AGATATTAAT TTAGATGGAG ACCACAATAT

1441 ACTTTTTGAT CAGTGTCTAA GGGGTGGATA TAATAATGTA TTAGATAAGT TAATACAACA

1501 AGGGGTTGAA GTTAATCGAA ATAGTGAAAT ACGTCCAATG GTTTATGCTG CAATATCTGG

1561 TAATGAGCAT GCTATCAAAT CATTAGCTAA TGCTGGTGGA GATGTTAATG AAGTAGTAAA

1621 TAATCCATCT AGTAGGCATT CAGGAAATCC TTTAATTATG GTTGCAGTAG CAGATGGTAA

1681 TGCAGGTCTT CTTAAAACAT TAGTTTCTGA AGGATGTGAT GTTGGTAAAT CTGGAAAAGA

1741 TGGTAATACA GCGTTACATT ATGCTGTTAG TCATTCAGAT AAAGAGTTTG GTAATAAAGC

1801 TATAAAGATA TTAATTTCAC GTAATAGTGT TGGGACTAAT AGAGATATTC TTACTCAAAA

1861 GAATAACGCA GGTGATACAC CTTTACATGA AGCTCTTAAG TCAGGTAATA TTAATTCTGT

1921 ACAGAATATC TTAAGTGCTG TACATCCAAG ATACGCAAAG GAGATATTAA CAGCCAGAGA

1981 CAAAGAAGGG TACACACCAA TGCATTATAC TGTTGGAGTA ATAATGTTG ATGTTGGTAG

2041 AAGTATTCTA GAGTCTATGC TCTCTAAAGG TGTGAATAAT CTTGGAGAGA TTGTTGGAGC

2101 ACAGGATAGT AATTTTCGAA CACCTCTGCA TGCTGCTATT AAAATATCTG ATTATCGTGC
```

-continued

```
2161 TGCGGACATG ATAATAGGTA GCTTATCGAA AACAGAATTG TCAAAGTTAT CGCAATTAAC

2221 AGATATTAAC GGGGATACAC CACTACATCT TTCTTGTCAG TCTGGTAATG TCGAGATGAC

2281 ACAATTCTTT CTTGGAGGTT TGGATAAACG TGAATTACCT AAGACATTAA AGATAGCAAA

2341 TAAAAATGGA GATACTCCTT TACATGATGC TATAAGAAAT GATGATATTA AATCTGCAAA

2401 AATGATGATT AGGAATTGTA ACAAGAAGA ACTTGCTAAT GTATTAAAAT GTAAAGATAG

2461 TTTTGGTAAT ACAGTATTGC ATACTATTGC TGACCAAGTT ATTGCGAATC CAGAATCAAA

2521 GAAAGACCTT GATGGTTTGA TGAATTTAGC AGTGAAAAGG CTAAAGAATC AAGATCTGAA

2581 AGATCTAGTT AATACGCGAA ATAACTCTGA CGATACTGTT GCACATTGTG CTCTTTTATC

2641 GGATATGAAA TATGCTCAAA AGATACTTAA ATCATGTAAC CATGATACAT TAGTGAGAGG

2701 AAATAGTAAT AATCAATCTT TATCAGAGTG TATTCGTGAT GATAGTAAAT ATAAAAAAGG

2761 TGGAATTTTT AGTAAGTCTT TATTTTCAAA ATTAAAGAAA CTTGAGGCAC GAGCTGCCAG

2821 CGCTAGTTAT GAAGAATTAT CTAGTATCAG TAGTGGTAGT GATGTTTCTT CTGTATCAAC

2881 AAATAGCACA GAAGTAAGTG CAGTACCTGA AGTGGCAAGA AGTAGTGGTG CTGTGTCGTT

2941 CAAACATGTG CAAGAAACAG GAGTTGACAC GTCTGGTCCT TCTGATATAG AAAGTTTAGA

3001 GAGATTATCT GATACTAGTC TTGGGTCAAA TGATTTTGAT CAGCGAATGG CAGATTTAGA

3061 TCAAGAAATA GCAATATTG TTAGTGGTTT ACCAGAAGTT ACCCAGGTAG CTGTAAGTCA

3121 ACAACAAGCA GCATCTCCTA GTTCAGGTCA AGCTGCTGGT GTGCAACAAA AAGAGATGCA

3181 GAGATAA
```

SEQ ID NO: 4    200 kDa Antigen Partial Protein Sequence
ORIGIN
```
       1 NLDFGLVDGD GKNPLHHAVE HLPPVILKGV MDHVKNSSEF QDLVNDPDYF GNTIAHYAVK

61 NKNADLTLFN MLKASGADLN VRNVVGRAPI HVASSNGKAN AVSGLVSCGI DVNSQDVNGD

121 TPLHIAVEGG SMETVLAVLN QRGADVSVQN NDGVTPMLSA AKYGDIGVIK ALGSAKPNIK

181 GEDTVAKSLL MEDYKGFTPL HFVAGGGSRD TFRVVRKNYE KCHDLATIRA ALMQDRSGGE

241 LVNLGDFESE NILGSPNAKF LQHIQSANFG FSPAHCAIVS SNHNVMKDIL NFVGDSLHLP

301 SERGYNAMQV AALFGDKEAV KMLAKSAKPS DLNFKTSATP TPLNLACLRG DNEVVRGLVG

361 QHGIDINQRM GSDKNTVLHY AISKGDSFLV QKILAHTGVD VNCENNLGQT PLHLAVEGGD

421 PKIVSSLLKA GAVVNRLDDN GRSVLSSAIV PGRKEKGVLG IVNKLLDRGA DINLDGDHNI

481 LFDQCLRGGY NNVLDKLIQQ GVEVNRNSEI RPMVYAAISG NEHAIKSLAN AGGDVNEVVN

541 NPSSRHSGNP LIMVAVADGN AGLLKTLVSE GCDVGKSGKD GNTALHYAVS HSDKEFGNKA

601 IKILISRNSV GTNRDILTQK NNAGDTPLHE ALKSGNINSV QNILSAVHPR YAKEILTARD

661 KEGYTPMHYT VGVNNVDVGR SILESMLSKG VNNLGEIVGA QDSNFRTPLH AAIKISDYRA

721 ADMIIGSLSK TELSKLSQLT DINGDTPLHL SCQSGNVEMT QFFLGGLDKR ELPKTLKIAN

781 KNGDTPLHDA IRNDDIKSAK MMIRNCNKEE LANVLKCKDS FGNTVLHTIA DQVIANPESK

841 KDLDGLMNLA VKRLKNQDLK DLVNTRNNSD DTVAHCALLS DMKYAQKILK SCNHDTLVRG

901 NSNNQSLSEC IRDDSKYKKG GIFSKSLFSK LKKLEARAAS ASYEELSSIS SGSDVSSVST

961 NSTEVSAVPE VARSSGAVSF KHVQETGVDT SGPSDIESLE RLSDTSLGSN DFDQRMADLD

1021 QEIANIVSGL PEVTQVAVSQ QQAASPSSGQ AAGVQQKEMQ R.
```

SEQ ID NO: 5  ATPase - Clone 84 Fragment Nucleotide Sequence
ORIGIN
       1 AATTATGCTG AAACTACTTT ATCATTTGGT GAATCTCGAG CAGAAGGACG TGAATCTCCA
      61 TCAAGTGCAT TTGTTCAAAC TGGTCAATCA GAAGTACCTC GGAGTGAGGC TGCAGAGCCA
     121 TTAATTCAAT TTCCTCATGA TGAAGAAAGT ACTGCATTAG GTTCTCAAGC AACTATGACA
     181 GGAGTGTCTA CTCAGGCTAG TCCGTCAGCA GCATATCAGG ATGATAGTGA AATATCACGT
     241 ATGAGGTCTA TGGCAGGAAC ATCTGCTCAA GCTGATCAAT CAGCAGTACA TCGTCGGAGT
     301 GGTACAGCAT TAGAGCCATT AATTGAATTG CCTGATGAAG AAGAAAATGC TGCATTAGAT
     361 TTTCAAACAG CTATGACAGG AGTGCCTACT CAGGCTAGTC CGTCAGCAGT ACATCGGAGT
     421 GGTGTTGCAT CAGATCCTAC GCTACCTGAT GATGAAAGAA TTGATGTTCC ATCAGTTTCA
     481 TCTCAAGTTG TAAGACCTTT TAGTGATGGT GAAGATTATT CAGTATATGA TAAATCAGGT
     541 GTAGTAAGTG GTCATGAAAG ACCTGTTTCT TCTAGAGATT CAAGACAATT GGATGCATTT
     601 GGTGATCCAT CAGATGATTT ATTGCCGGAG AGTGAAATTA TTGTTAGCAG CAGTAAGAAA
     661 GCAATATTAG ATAGCCAAAA TGAAATAGAA TCTCTTATTC AGAGTGGAGA TACTTCTAGA
     721 TGTATTAGGG CAATTAATAG TGCTCCTAGT GCGTCAGTGT TTCAACTGAA GACTTTATCG
     781 AATGATATAT CTATTGCTGG ACGTGCTTTT TTAAATGGTA ATATTGATTT AATAGAAGCT
     841 TGTATGAATT CTGGCAAGAA ATTAAATCCA ATATTACTG ATAATGAAAA AAATACTCTA
     901 TTACATCAAT TTGTAGGATA TTTTGAACGC GATCCGAGAA TGTTGCTTGA TGCAGGAATG
     961 CGTAATCTGT TTTTGAGATT ATGCATGGAT TATGGTTTCG ATATTAATCA TAAAAATAGT
    1021 AATGGTAATA CAGTACTTGA TAGATTAAAT GATTTAGTAG AAGGGTTAAG TAGTTCGCAA
    1081 GTTGATCTTG AAAGTAGTGG TATTGATGAG TTTATGATCT CATTGTTAGC TCATTCTAGA
    1141 ATGAGTGATC AAGCAGTAAA GAATATTGCT ACTGCGCAAA ATGAGTTTTT TGCACGTGAT
    1201 TCTGTTTATA ATATTAGTCG TTTAGTTGAT ACTTCTATAG TTTTGCAGAA TAAATTCAGT
    1261 GAAGTATTTT ATGAAGTCTG TGGACGTATT TTATCTGAAG AAGCTGGTAA ACATAAGGGT
    1321 GTTGCTGAAG CAAATTATTC AAGATTGAAT AAAATATTAA ATGATGAATG TCTTAGAAAG
    1381 ACTTTAGCTA ATACAGATGC CGATGGAAAT AATGTTTTAC AGAGATTGTG TCAAGATATT
    1441 GCTTCTGGAA AAATCAATGC TCGTGATGAC AGAGTATTAA AACTTTTTGA GACAATTATA
    1501 TCTAATTTAA AAGACAAAGA TAAAGCATTA CTAGAGGATT TATTATTTAA TAATAGAAAC
    1561 TCAAGATTTG AAAATTGCAT TGAAGCTATA CCACGTATTC CTGGTGCCGA TGCTCTATTT
    1621 AAAAAACTAG AAGAGTTATT ATTAAAAAAG AAAATAGCAG AGTCTTGTGA TTTTAATTCT
    1681 ATGTTAGTGA ATTGTGCTGA GTCTGCTAAT GATAATTTAT ATAATTACCT GCGCACTAAT
    1741 TATGCAGTTA TTGGTATAAA TAACGTAGAT ATAAATGGCA ATTCATCCCT ATGTAAAGCT
    1801 GTTGTTACTG GGTCACAAGG TATTGTTAAA GCAGTATTAT CAACTGGAAC TAATATTAAT
    1861 AGGAAAGATA AAAATGGTAA TACACCTTTA CATGCATTGT TAATTTTTAT GATGTCTAAC
    1921 CCTGAACTTG TCAAGGAGCA ACATATTTCA CTTGTGAAAT TCTTAGCGTC TCGTGGAGCT
    1981 TTACTTAATG TAAAAAATAA TATGAATATT TCTCCAATTA TGCTTGCAGA ATCTATTGAT
    2041 AAGAAAGAGG AACTTGCTAA GAAATTTACA AATCAAAAAG TTAGTATTTT AGAATCTTTA
    2101 ATAGCTGGTA GTGAAGAACA TTTAGGGCTT AAATCCAAAT GTATATCTGA GTTAAAGCCT
    2161 TATATAGAAT TAGGAAAAGG CATGAAGTAC GAAGATATAC ATGCTGATGT AATAGGTGGT

```
                             -continued
2221  GTATTATCTG CTGATATGTG TAATGCTAGA TTGCAGATAG GTAAATTATT AAATGGTGAT

2281  TTTTGTAAAG AAAATGAATT AAAGACAGTA AAATTTAATT TTTCTGATAC AAATAAGGGT

2341  TATGTACAAA ATGTTGGTAA AAAAAGAAAT TAT

SEQ ID NO: 6   ATPase - Clone 84 Fragment Protein Sequence
ORIGIN
    1  NYAETTLSFG ESRAEGRESP SSAFVQTGQS EVPRSEAAEP LIQFPHDEES TALGSQATMT

61  GVSTQASPSA AYQDDSEISR MRSMAGTSAQ ADQSAVHRRS GTALEPLIEL PDEEENAALD

121  FQTAMTGVPT QASPSAVHRS GVASDPTLPD DERIDVPSVS SQVVRPFSDG EDYSVYDKSG

181  VVSGHERPVS SRDSRQLDAF GDPSDDLLPE SEIIVSSSKK AILDSQNEIE SLIQSGDTSR

241  CIRAINSAPS ASVFQLKTLS NDISIAGRAF LNGNIDLIEA CMNSGKKLNP NITDNEKNTL

301  LHQFVGYFER DPRMLLDAGM RNLFLRLCMD YGFDINHKNS NGNTVLDRLN DLVEGLSSSQ

361  VDLESSGIDE FMISLLAHSR MSDQAVKNIA TAQNEFFARD SVYNISRLVD TSIVLQNKFS

421  EVFYEVCGRI LSEEAGKHKG VAEANYSRLN KILNDECLRK TLANTDADGN NVLQRLCQDI

481  ASGKINARDD RVLKLFETII SNLKDKDKAL LEDLLFNNRN SRFENCIEAI PRIPGADALF

541  KKLEELLLKK KIAESCDFNS MLVNCAESAN DNLYNYLRTN YAVIGINNVD INGNSSLCKA

601  VVTGSQGIVK AVLSTGTNIN RKDKNGNTPL HALLIFMMSN PELVKEQHIS LVKFLASRGA

661  LLNVKNNMNI SPIMLAESID KKEELAKKFT NQKVSILESL IAGSEEHLGL KSKCISELKP

721  YIELGKGMKY EDIHADVIGG VLSADMCNAR LQIGKLLNGD FCKENELKTV KFNFSDTNKG

781  YVQNVGKKRN Y

SEQ ID NO: 7   ATPase - Clone 7 Fragment Nucleotide Sequence
ORIGIN
    1  GTAAAAAAAT TAAGATTATT ATTAAATTCA ATAAGTGAGT TACCGCAAGA ATTAAAAGAT

61  CAAATTTTAA GTACTAGAAG TACTATAGAT AAATTACGAA ATAGAATTAA TGCCTGCATA

121  AAGTCTGACG ATAGAGAAGG TATTGCACAT GCTGTAGAAT CTATGGCTAG TTCTTATTGT

181  GAATTATTAG ACATTGTAG ATTAATTTTT AAGAAATTAT ATGATGAAAA TGCTGATAAA

241  AGTTTGCTAG AATTATGTAT TAAAGAATAT CAATCTGATT TAAACAAATT ATTGGAACAA

301  GGTATTGATA TATGTGCTTC AGAAGTCTCA TCAGAATGTA AGGATTTAGT TTGTAAAGTA

361  TGTGAAGATG AATTTGAGAA ATATGACTCT TTATCTAAAG TACAAAGATT CAGGGAATTA

421  TCTGGTGAAA TTGCTGATTT GGATGATAAA TTAACAAGAA GGGCTTCTTT TGTTGAGACT

481  TTTGGATTAT TTAGCAGTAG ATTAAGACAT TATAGGGAAA TTTTAGGAGA TGGTGATTTA

541  AAATTTCGAG AGAGGATAGT TGAAAAATAT CAAGAGGATT TAAAGGAATT ATTAGAATTA

601  TCTGTTGATC TTCATTTGTT AATAAATTTA CCAGCATTAG AAGATTTACG CGATCATAGA

661  AATTTAGTGC ATAGAGCATG TAATGCTGAA ATTGAAAAAT ATCTAACTTT ATTTGATGAT

721  CAACAATTAC GTACATTATC GCAAGAAGTG AATAATGCTC ATGGTGAATT GATACAGATG

781  TTTTCTAAGT TTAGTATATT TGTTGATGGC GTTACTGGTA TTGAACAGAG CACATCTCAA

841  GTAGAGCACC CTCGTTCTGA TATTGCTAAA AGAGATACTA CAACACCAAA GCAACGTGTT

901  GTGCAAGGTA AAGATGATAT ACAATCTAGT GATAGTGATA GTGATAGTGA TAGTAAATAC

961  GGTGATGATG ATAGTAAAAA AGCATCAGTT AGTGCACCTG CTGTTGACCA AGTTGTACCT

1021  GTAGCTGATG TTCAACCTGA ACCTCAGCTA GGTGAAGGAT TGGAAACATT AGAGTCTAGT

1081  ATAGCTGAAG GACCTGAGTT GCCTGGTGAT GCATCTACTG CTAAGCAATC TATACCTTTT

1141  GCGATAACAC CATCAAGTCC TGAGACAGTT GATGAAAAAC TTGAAAGTTC TGGTGTTAGT

1201  CAAGATGGTA TTACAACACC AGGACAACGT GTTGTGCAAG GTAAAGATGA TATACAATCT
```

-continued

```
1261 AGTGATAGTG ATAGTGATAG TAAATACGGT GATGATGATA GTAAAAAAGC ATCAGCTAGT
1321 GCACCTGCTG TTGACCAAGT TGTACCTGTA GCTGATGTTC AACCTGAACC TCAGCTAGGT
1381 GAAAAATTGG AAACATTAGA GTCTAGTATA ACTAAGGAC CTGAGTTGCC TGGTGATGCA
1441 TCTACTGCTA AGCAATCTAT ACCTTTTGCG ATAACACCAT CAAGTCCTGA GACAGTTGAT
1501 GAAAAACTTG AAGTTCTGG TGTTAGTCAA GATGGTATTA CAACACCAGG ACAACGTGTT
1561 GTGCAAGGTA AAGATGATAT ACAATCTAGT GATAGTGATA GTGATAGTAA ATACGGTGAT
1621 GATGATAGTA AAAAAGCATC AGCTAGTGCA CCTGCTGTTG ACCAAGTTGT ACCTTCTGAC
1681 ACTCGTGCAG ATGGAGTATC AGAACCATTA GCATCTCATG TGGATCAAGG ATCTGATGTA
1741 CCTGGTGATG CATCTGTTGA TGGTGTTGAT TTAAGATTAG GACGGTTATC TACTGAGCAA
1801 AGTGGATTGT TGCCACGTCA TGAACAAAAT GTAAGAGCAT TTATTTTAGA ACAGAGTTTG
1861 TTAGATCAAT TATATATGGA CTATATAGAT TTACACCCTG ATCAGAAAAG TTGTGAAGCT
1921 TATAATTCAG CATTGCATGG ATATAATACA AGATTAGAGT TACAGAAGGA ATATAACAGG
1981 ATTTTTGAAT CACATGAATC AGCATCTCCA ATGAAATTA ATAGTTTTTC ACAAAAATAT
2041 AGAGCAGCAT TAAGAGATGT TGCGCAGGAT ATTGTTAATC AGGGTCCAAT GTTTTATTCT
2101 TCTAGAGATG CAATGCTATT AAGGGCTAGA GTAGACACAT TGTGTGATAT GTGTCGTTCA
2161 ATACGTAATC TGTATATGGT TGAATTAGAT GCCATAGATA AGAAGAAAA ATCGTTACAA
2221 TCTGATATGA AATCTGCAAG TTCTAGTGAT AAAAAGTTGA TACAAGAAAA AATAAAATTA
2281 CTT
```

SEQ ID NO: 8  ATPase - Clone 7 Fragment Protein Sequence
ORIGIN
```
      1 VKKLRLLLNS ISELPQELKD QILSTRSTID KLRNRINACI KSDDREGIAH AVESMASSYC
     61 ELLGHCRLIF KKLYDENADK SLLELCIKEY QSDLNKLLEQ GIDICASEVS SECKDLVCKV
    121 CEDEFEKYDS LSKVQRFREL SGEIADLDDK LTRRASFVET FGLFSSRLRH YREILGDGDL
    181 KFRERIVEKY QEDLKELLEL SVDLHLLINL PALEDLRDHR NLVHRACNAE IEKYLTLFDD
    241 QQLRTLSQEV NNAHGELIQM FSKFSIFVDG VTGIEQSTSQ VEHPRSDIAK RDTTTPKQRV
    301 VQGKDDIQSS DSDSDSDSKY GDDDSKKASV SAPAVDQVVP VADVQPEPQL GEGLETLESS
    361 IAEGPELPGD ASTAKQSIPF AITPSSPETV DEKLESSGVS QDGITTPGQR VVQGKDDIQS
    421 SDSDSDSKYG DDDSKKASAS APAVDQVVPV ADVQPEPQLG EKLETLESSI TKGPELPGDA
    481 STAKQSIPFA ITPSSPETVD EKLESSGVSQ DGITTPGQRV VQGKDDIQSS DSDSDSKYGD
    541 DDSKKASASA PAVDQVVPSD TRADGVSEPL ASHVDQGSDV PGDASVDGVD LRLGRLSTEQ
    601 SGLLPRHEQN VRAFILEQSL LDQLYMDYID LHPDQKSCEA YNSALHGYNT RLELQKEYNR
    661 IFESHESASP NEINSFSQKY RAALRDVAQD IVNQGPMFYS SRDAMLLRAR VDTLCDMCRS
    721 IRNLYMVELD AIDKEEKSLQ SDMKSASSSD KKLIQEKIKL L
```

SEQ ID NO: 9:  p16 Antigen Nucleotide Sequence
ORIGIN
```
      1 ATGTTACACG TTCAAAATCA TGTTGATCAA CATACAAATC ATATAGAACA TGATGATTAC
     61 CATTTTACTG GTCCTACTAG TTTTGAAGTT AATCTTTCTG AAGAAGAAAA AATGGAGTTA
    121 CAAGAAGTAT CTTCTATTGA TAGTGTAGGA TGCGAAGATT GTGATCCAAA TTGTCGTTAT
    181 CCTTTAGAAT TAGTAGAATG TCAGCGTATT GAGGAAAGAC CAGTATGCAA TGCAGGTTTA
    241 GAGAGCTTGA CTGTTGATGC ATATCAATTA GGATTGTTGT TAGGTGGTTT TTAAGTGCT
    301 ATGAATTACA TATCTTATAG CTATCCTTGT TATTATTATG ATTGTTGTGA TAGAAATTAT
    361 TACGACTGTT GTCATAAGAA TGCGTGTTAT TACAACTGTT GTGATTGTGC GTAA
```

-continued

SEQ ID NO: 10  p16 Antigen Protein Sequence
ORIGIN
     1 MLHVQNHVDQ HTNHIEHDDY HFTGPTSFEV NLSEEEKMEL QEVSSIDSVG CEDCDPNCRY

61 PLELVECQRI EERPVCNAGL ESLTVDAYQL GLLLGGFLSA MNYISYSYPC YYYDCCDRNY

121 YDCCHKNACY YNCCDCA.

SEQ ID NO: 11  Ribosomal Protein L1 Nucleotide Sequence
ORIGIN
     1 ATGACGATTT TCTTAGAAAG TGATGATGAT AAGAGTAACT TTAAGAAGAC ATTGGAGAAC

61 GGTACTAAAG ACAAGACAAA TCTAGATAAT ACTTATTATG ACTATCATCA TGAAGATGAT

121 ATGGGAAATA CTGAATATCA TTATGTGAGT TTGGATAGAG TGGATCATGT TAAGATGCCT

181 GAAGAGCCTG TAGGTTATGG TGGAGATACT TTACCTATTG TTCCTACTAC AGCTGCTAGT

241 GTATCTGGTA GTGATGCAGG CGTTGCTGTA GGTAATGTTA AGATTTTGA AGATAATGTT

301 TTTCATCATA CATCTACTAT AAGAAACGAT GAATTGAAGA TAGATTTACG AATACATACT

361 TTAAAGGATT TATCTGATAA AAGATTACGT GAAATTGAAA AGGGATTTAA TGATACGGTA

421 ACAAAATTTA AAATAATTT TGGGTTAGAA CCAAATGATG GAGAAACTAT TTTTGATTTA

481 TACCTTTTTG ATGATAAGGA ACAATATAAT TATTATGAA AGCTTTATAA CTTAGGAATT

541 AGTGGATCTG GAGGTATGAC TTTCTATGGA AATGCTAATG TTCCATATAA AATTTATGTA

601 CATCAATATG GTGAAATATT GAATTTAAAA CATGAATTAA CTCATGCATT AGAAAGTTAT

661 GCATCTGGAC ATAAATTGCA TGGTTCTGAC GTAAATAGCA GAATATTTAC GGAAGGATTA

721 GCTGATTATA TCCAAGAAGA TAATAGTTTT ATTATGGAGG ATTAAAGGA TCGAGAGATC

781 ACTTCAGATG TATTGAAAGA TTCTTCTGGT AATGTAGATC ATTTAAGTGG TGTTGCAGTG

841 AATGAAAATC AGAGGTTAAG TTATAGTATA GGACATGCAT TTGTAAGCTT TTTACAAGAG

901 AAATATCCTA AGTTAATTTC GGAATATTTA AACGCATTAA AAGAGGATAA TATTATTCGT

961 GCTAAAGAAA TAATTAGTAT GGATAAGTAT CCAGATTTTG AGCCGTGGGT GAAGTCTAAA

1021 GACATTAGTT TATATTTAGA AAATATGAAT GTATTAAAGT TAGGATTAGG TGAGAAAATG

1081 TTTTCTGCTG AAAGTGCTAG CTATTTTGAA GATCAAGGTG TCAATAAAGA ATATTACCAT

1141 GAAAATATTT ATGATATGAG TGGTAAACTA GTAGGTAAA TGTCACCTGT AGTGCATTAT

1201 GCACAAAAAA ATGTGATTCG TATTTGGAAT ATTGCAAGTC CTGATATGAT AGAGGTGCGA

1261 CCAGAATATA ACTTTCTGAA ATTGGTAACT ACTCCATCTG GTAAGTCTGC ATATGTATAT

1321 TGTGATAAGA ATGGGCATGA GTATTTTAAT ACTAAAGATT ACATAGATTC TGCGTTTAAT

1381 ATATTGGCAA GATATGATGT TAAGCTTCGT GAAAGTAGTG ATGCTTTGGA TATTAGAGGT

1441 CGTTACTCAG ATGCTGCTAA AGTGTTTAGT AAGCTGCCTA ATGCGGATTT GCTGTTGGAT

1501 AAGTTTTTAG AAAAAATAGG TTATAGTAGT TATAAGCAGA TAATAATGAG TAATCCAGAA

1561 CAGCTTAATT CTATTAAGGC TTATGTAGTA AAAGAAGTGT TTGAAAATTT TAGGGAATCT

1621 GAGGTCAAAA AGGTGTTGAG TGGTGAGTCT CATCCGGAAG TAAGAAATGT ATTAATGGAT

1681 CTTACCTATG TTGATTTAAA GAGTGTTATA GGAGTAAATG GTGCAGATAT TGACAGTATT

1741 ATTTCTAATC CAGATGTAAT GTTGCGTACT GCTGTGTTAG GTAAAGGAAA TGCAAGTGGG

1801 ATATCTCTAT ATGTAGATGA TCAGAAAGTT GGTGAGCTGT CAACTGAAGC AGGTTATTGT

1861 GTTAAAAATC TTGATACTGG TAAAGTGTAT TTTATGTTCC ATAATGTTGT TGGAATGATA

1921 GCAAGTGGTT ATGAAGACAG AGCATATATG GTTGTATTAG AAAAAGATGG TAAGTTTACT

1981 ACTGCTCTAG TTAATAATAT ACAAAAAGCA GCAGATGGAA ATGTTGTATG GGATAATCAA

2041 TTTAATCATC CGAATATTAA TAACTTGCAC TCAAATTATA AGGAGCTGTT GTTAAATGAT

-continued

```
2101 GCTTCAGTTA AAGATTACTC TCATCTTGCG GATGTGAAAT TTAATAAAGA TGATACAGTA

2161 ATTGTTAAAG GTGAATTATT AGATGATAAA GGTACTGTAA GTGTAGATGA TGATGTACAT

2221 CGTGCAGTTG TTAAGCATGA TGATCAAATA CTACATCAGT TTAAGAGTAT GTCTTTTTAC

2281 ATTACTGAAC CATCAGCTGA TTCAGGTGAC AATTATGGAA GTGATTTTTT CATTTCTGAT

2341 GAAGGAAAAA ATCTTAGATT TCAACTTCCT AAAGCTATTA CGCATTTGAA ATTGGTTAAT

2401 GTTAATGGAA ATAATAAGTT GGTACCATGT ACTAAAGATG GAATGAACA TCCTGAAGGT

2461 ATGCCATCTG ATTTAACGGA TGAATATAGA TATATAGATC CTATTTTTGC TCATACATTT

2521 GAGAAACAAA GTTATTCTAA AAATAGTATT AGTGTTGGGT TAGTGGACTT CAGTAAATAT

2581 AAAGAAGGAT CTATGTTTAA ATTACAGCAT TATTCTGATG ATTATCATAT TCATAAGGAT

2641 GAACAAGGTA ATGTTATTAG GCCTAATAAC AGATCTTACG TTACAAAAGT GGATTTAGTA

2701 TATGATGATA AAGTTATTGG GATGTTGTCT GATAGTATAA ATCAATTTCA GGGTGATATT

2761 TTCATTTCTG CAAGCCTTAA TTATAGCCAC AATGATTTTC TTTCATCTAA GTACTTTCAG

2821 AAAGTTAATA TTGAGGCGTT AGAAAATGGA ATATATAGTG GAAGATATGA TGTAGGAGAT

2881 CGTGACCAAA TAGCAGGTCT TAATACTGAT ACAGGTTATA GTGATAAAGC TATTTTTTAC

2941 TTTAAAAATG ATAGCGCATC TACTGATATG CCGGCTAGTG ATGTTACTAC TATTTTACCT

3001 TATATAAATG AGCTTTAA
```

SEQ ID NO: 12 Ribosomal Protein L1 Protein Sequence
ORIGIN
```
  1 MTIFLESDDD KSNFKKTLEN GTKDKTNLDN TYYDYHHEDD MGNTEYHYVS LDRVDHVKMP

61 EEPVGYGGDT LPIVPTTAAS VSGSDAGVAV GNVKDFEDNV FHHTSTIRND ELKIDLRIHT

121 LKDLSDKRLR EIEKGFNDTV TKFKNNFGLE PNDGETIFDL YLFDDKEQYN YYGKLYNLGI

181 SGSGGMTFYG NANVPYKIYV HQYGEILNLK HELTHALESY ASGHKLHGSD VNSRIFTEGL

241 ADYIQEDNSF IMRGLKDREI TSDVLKDSSG NVDHLSGVAV NENQRLSYSI GHAFVSFLQE

301 KYPKLISEYL NALKEDNIIR AKEIISMDKY PDFEPWVKSK DISLYLENMN VLKLGLGEKM

361 FSAESASYFE DQGVNKEYYH ENIYDMSGKL VGEMSPVVHY AQKNVIRIWN IASPDMIEVR

421 PEYNFLKLVT TPSGKSAYVY CDKNGHEYFN TKDYIDSAFN ILARYDVKLR ESSDALDIRG

481 RYSDAAKVFS KLPNADLLLD KFLEKIGYSS YKQIIMSNPE QLNSIKAYVV KEVFENFRES

541 EVKKVLSGES HPEVRNVLMD LTYVDLKSVI GVNGADIDSI ISNPDVMLRT AVLGKGNASG

601 ISLYVDDQKV GELSTEAGYC VKNLDTGKVY FMFHNVVGMI ASGYEDRAYM VVLEKDGKFT

661 TALVNNIQKA ADGNVVWDNQ FNHPNINNLH SNYKELLLND ASVKDYSHLA DVKFNKDDTV

721 IVKGELLDDK GTVSVDDDVH RAVVKHDDQI LHQFKSMSFY ITEPSADSGD NYGSDFFISD

781 EGKNLRFQLP KAITHLKLVN VNGNNKLVPC TKDGNEHPEG MPSDLTDEYR YIDPIFAHTF

841 EKQSYSKNSI SVGLVDFSKY KEGSMFKLQH YSDDYHIHKD EQGNVIRPNN RSYVTKVDLV

901 YDDKVIGMLS DSINQFQGDI FISASLNYSH NDFLSSKYFQ KVNIEALENG IYSGRYDVGD

961 GDQIAGLNTD TGYSDKAIFY FKNDSASTDM PASDVTTILP YINEL.
```

SEQ ID NO: 13 Type IV Secretory Protein VirD4 Nucleotide Sequence
ORIGIN
```
  1 ATGGATAGTA TAAGTGCAAA TCACATACGC AATATTTAT TCCTTGTTTT AGGCGCATTT

61 TTTGGACTGG AATTTTGCTT TTATTTATCA GGTGTATTAT TCATCTTAAT GGTCTGGGGA

121 CCAAATTACC TAGATTTTAA TGCTATAAAT CCCAGTTTGA GTGATTTTCC AGACAGAATT

181 TGGCCAACTA TTTTTGACTA TGTACAACAT TGGTGGAAGA ACCCTTCTGC ATACGATGCA

241 GTTTTATTAC TTAAGCTAAT AACGTCATTA TGTACACCAG TAGGTATTCT AAGCATAGTA
```

```
 301 TTATGGAACC TTAGAAATAT ATTATTCGAT TGGAGGCCAT TTAAGAAGAA GAATCACTG

361 CATGGAGATT CAAGATGGGC AACAGAAAAA GATATTCGCA AATAGGATT ACGTAGTAGA

421 AAAGGAATAT TATTAGGGAA AGACAAGAGA GGATATCTCA TTGCAGATGG ATATCAACAT

481 GCATTGTTAT TTGCACCAAC TGGATCCGGA AAAGGTGTAG GTTTTGTAAT ACCAAACTTA

541 TTATTCTGGG AAGATTCTGT AGTAGTACAC GATATAAAAT TAGAGAACTA TGATCTTACA

601 AGTGGGTGGA GAAAAAAAG GGGACAAGAA GTTTTCGTGT GGAACCCAGC ACAACCTGAC

661 GGTATAAGTC ACTGTTACAA CCCATTAGAT TGGATAAGCT CTAAGCCTGG ACAAATGGTA

721 GATGATGTAC AAAAAATTGC CAATCTAATA ATGCCTGAAC AAGATTTTTG GTATAACGAA

781 GCACGTAGTT TATTTGTAGG AGTAGTATTA TACTTACTAG CAGTACCAGA AAAAGTAAAA

841 TCCTTTGGAG AAGTTGTAAG AACAATGCGC AGCGATGACG TAGTCTACAA CTTAGCAGTA

901 GTACTAGACA CAATAGGGAA AAAGATTCAC CCAGTTGCAT ACATGAATAT AGCTGCATTT

961 TTACAAAAAG CAGACAAAGA ACGCTCAGGT GTTGTATCAA CTATGAACTC ATCTTTAGAA

1021 TTATGGGCAA ACCCATTAAT AGATACAGCA ACAGCATCAA GTGATTTTAA TATTCAAGAA

1081 TTTAAAAGGA AAAAAGTAAC AGTATATGTT GGATTAACAC CAGATAATTT AACTCGTCTT

1141 AGACCTTTAA TGCAGGTATT TTATCAACAA GCTACAGAAT TTTTATGTAG AACTTTACCA

1201 TCAGATGATG AACCATATGG TGTACTGTTC TTAATGGATG AGTTTCCAAC ATTAGGAAAA

1261 ATGGAGCAAT TCAAACAGG TATCGCATAT TTCCGTGGAT ATAGAGTTAG ACTATTTTTG

1321 ATTATTCAAG ATACTGAACA GCTTAAGGGT ATATATGAAG AAGCAGGAAT GAACTCATTC

1381 TTATCAAACT CTACTTATAG AATAACTTTT GCTGCAAATA ATATAGAAAC TGCAAATTTA

1441 ATATCACAGT TAATAGGAAA TAAAACTGTT AACCAAGAGT CTTTAAACAG ACCTAAATTT

1501 TTAGATTTGA ACCCTGCATC ACGTTCATTA CATATATCAG AAACACAAAG AGCTTTACTA

1561 TTACCTCAAG AAGTAATAAT GTTACCCAGA GATGAGCAAA TACTTTTAAT AGAATCTACT

1621 TATCCTATAA AATCAAAGAA AATAAAATAC TATGAAGACA AAAATTTTAC AAAAAAACTA

1681 TTAAAGAGTA CCTTTGTTCC AACTCAAGAG CCTTATGATC CAACAAAAC AAAAACAGCA

1741 ACAAAAGAAA ACGAAGAACC TATGCCAAGT ATTGAAAGCG ATCTTCCTAA AATACATCT

1801 GACAATACTG AAAACAATAT GGAAGATGGT GCAATGTACA GCAGCATAGA AGAAGATTAT

1861 GACGATGATG ATGATGATTT TAATTTTGAA GACTTAGATG AATATATGGA TGAAGAAGAA

1921 GATTATGATG ATGAAGAATA TGATGATATA GATTATGATG ATAATAACAA TAGTAATGAG

1981 GAGTATGAAG AAGATAATCC AGAAGAAGAT GACAATAGCA ATAATCTAGA CGATGAGGAA

2041 GAGGAAGAAG ATAATATTAT AGATTATGAA GATGAAGAAG AATATGATGA TAACATAGAC

2101 TACAAAGATG ATGCAATAA CTACAACAAA GATACCACTG ACGATCAAGA CTCAAAAAAA

2161 CATAATGAAT AG
```

SEQ ID NO: 14  Type IV Secretory Protein VirD4 Protein Sequence
ORIGIN
```
   1 MDSISANHIR NILFLVLGAF FGLEFCFYLS GVLFILMVWG PNYLDFNAIN PSLSDFPDRI

61 WPTIFDYVQH WWKNPSAYDA VLLLKLITSL CTPVGILSIV LWNLRNILFD WRPFKKKESL

121 HGDSRWATEK DIRKIGLRSR KGILLGKDKR GYLIADGYQH ALLFAPTGSG KGVGFVIPNL

181 LFWEDSVVVH DIKLENYDLT SGWRKKRGQE VFVWNPAQPD GISHCYNPLD WISSKPGQMV

241 DDVQKIANLI MPEQDFWYNE ARSLFVGVVL YLLAVPEKVK SFGEVVRTMR SDDVVYNLAV

301 VLDTIGKKIH PVAYMNIAAF LQKADKERSG VVSTMNSSLE LWANPLIDTA TASSDFNIQE

361 FKRKKVTVYV GLTPDNLTRL RPLMQVFYQQ ATEFLCRTLP SDDEPYGVLF LMDEFPTLGK
```

```
-continued
421  MEQFQTGIAY FRGYRVRLFL IIQDTEQLKG IYEEAGMNSF LSNSTYRITF AANNIETANL

481  ISQLIGNKTV NQESLNRPKF LDLNPASRSL HISETQRALL LPQEVIMLPR DEQILLIEST

541  YPIKSKKIKY YEDKNFTKKL LKSTFVPTQE PYDPNKTKTA TKENEEPMPS IESDLPKNTS

601  DNTENNMEDG AMYSSIEEDY DDDDDDFNFE DLDEYMDEEE DYDDEEYDDI DYDDNNNSNE

661  EYEEDNPEED DNSNNLDDEE EEEDNIIDYE DEEEYDDNID YKDDDNNYNK DTTDDQDSKK

721  HNE.
```

SEQ ID NO: 15
MDIDNNNVTTSSTQDKSGNLMEVIMRILNFGNNSD
EKVSNEDTKVLVESLQPAVNDNVGNPSSEVGKEEN
APEVKAEDLQPAVDGSVEHSSSEVGKKVSETSKEE
STPEVKAEDLQPAVDGSIEHSSSEVGEKVSKTSKE
ESTPEVKAEDLQPAVDDSVEHSSSEVGEKVSETSK
EENTPEVKAEDLQPAVDGSIEHSSSEVGEKVSKTS
KEESTPEVKAEDLQPAVDDSVEHSSSEVGEKVSET
SKEENTPEVKAEDLQPAVDGSVEHSSSEVGEKVSK
TSKEESTPEVKAEDLQPAVDDSVEHSSSEVGEKVS
ETSKEENTPEVRAEDLQPAVDGSVEHSSSEVGEKV
SETSKEESTPEVKAEDLQPAVDSSIEHSSSEVGKK
VSETSKEESTPEVKAEDLQPAVDGSVEHSSSEVGE
KVSETSKEENTPEVKAEDLQPAVDGSVEHSSSEVG
EKVSETSKEENTPEVKAEDLQPAVDGSVEHSSSEV
GEKVSETSKEESTPEVKAEDLQPAVDDSVEHSSSE
VGEKVSETSKEESTPEVKAEDLQPAVDGSVEHSSS
EVGEKVSETSKEESTPEVKAEVQPVADGNPVPLNP
MPSIDNIDTNIIFHYHKDCKKGSAVGTDEMCCPVS
ELMAGEHVHMYGIYVYRVQSVKDLSGVFNIDHSTC
DCNLDVYFVGYNSFTNKETVDLI

SEQ ID NO: 16
KEENAPEVKAEDLQPAVDGSVEHSSSEVGKKVSETS
KEESTPEVKAEDLQPAVDGSIEHSSSEVGEKVSKTS
KEESTPEVKAEDLQPAVDDSVEHSSSEVGEKVSETS
KEENTPEVKAEDLQPAVDGSIEHSSSEVGEKVSKTS
KEESTPEVKAEDLQPAVDDSVEHSSSEVGEKVSETS
KEENTPEVKAEDLQPAVDGSVEHSSSEVGEKVSKTS
KEESTPEVKAEDLQPAVDDSVEHSSSEVGEKVSETS
KEENTPEVRAEDLQPAVDGSVEHSSSEVGEKVSETS
KEESTPEVKAEDLQPAVDSSIEHSSSEVGKKVSETS
KEESTPEVKAEDLQPAVDGSVEHSSSEVGEKVSETS
KEENTPEVKAEDLQPAVDGSVEHSSSEVGEKVSETS
KEENTPEVKAEDLQPAVDGSVEHSSSEVGEKVSETS
KEESTPEVKAEDLQPAVDDSVEHSSSEVGEKVSETS

-continued

KEESTPEVKAEDLQPAVDGSVEHSSSEVGEKVSETS

KEESTPEVKAE

SEQ ID NO: 18 *E. canis* P140-1 (72,89)
CPEVKAEDLQPAVDGSVEH

SEQ ID NO: 19 *E. canis* P140-3 (64,89)
CEVGKEENAPEVKAEDLQPAVDGSVEH

SEQ ID NO: 20 *E. canis*
CKEESTPEVKAEDLQPAVDGSVEHSSSEVGEKVSETS

SEQ ID NO: 21
XPEVKAEDLQPAVDGSVEHX, wherein X = 0, 1, 2, 3, 4, 5, 6, 7, 8, 9, 10, 11, 12, 13, 14, or 15 amino acids.

SEQ ID NO: 22 *E. canis*
CKEESTPEVKAEDLQPAVDGSVEHSSSEVGXKVSETS; wherein X = K or E.

We claim:

1. A method of distinguishing between animals that (1) have been infected with *Ehrlichia canis* and animals that (2) have not been infected with *E. canis* regardless of whether the animal has been vaccinated with an inactivated whole cell *E. canis* vaccine, the method comprising:

(a) contacting a biological sample from an animal with one or more purified *E. canis* polypeptides that do not specifically bind to antibodies that are a component of the animal's immune response to an *E. canis* vaccine; wherein the one or more purified *E. canis* polypeptides consist of the amino acid sequence set forth in SEQ ID NO:18, SEQ ID NO:19, SEQ ID NO:20, SEQ ID NO:22, or combinations thereof and wherein, optionally, the one or more purified *E. canis* polypeptides are linked to a heterologous protein, an indicator reagent, an amino acid spacer, a signal sequence, a stop transfer sequence, a transmembrane domain, a protein purification ligand, or a combination thereof;

(b) detecting whether antibodies in the sample specifically bind to the one or more purified *E. canis* polypeptides; and (c) wherein if antibodies in the sample specifically bind to the one or more purified *E. canis* polypeptides, then the animal has been infected with *E. canis*.

2. A method for determining the presence or absence of an antibody or fragment thereof, in a test sample, wherein the antibody or fragment thereof specifically binds to one or more purified polypeptides consisting of the amino acid sequence set forth in SEQ ID NO:18, SEQ ID NO:19, SEQ ID NO:20, SEQ ID NO:22 or combinations thereof comprising:

contacting the test sample with one or more purified polypeptides consisting of the amino acid sequence set forth in SEQ ID NO:18, SEQ ID NO:19, SEQ ID NO:20, SEQ ID NO:22, or combinations thereof, wherein the one or more purified polypeptides are optionally linked to a heterologous protein, an indicator reagent, an amino acid spacer, a signal sequence, a stop transfer sequence, a transmembrane domain, a protein purification ligand, or a combination thereof, under conditions suitable for specific binding of the one or more purified polypeptides to the antibody or fragment thereof; and detecting the presence or absence of specific binding;

wherein the presence of specific binding indicates the presence of the antibody or fragment thereof, and wherein the absence of specific binding indicates the absence the antibody or fragment thereof.

3. The method of claim 2, wherein the method further comprises detecting the amount of specific binding.

4. The method of claim 2, wherein the one or more purified polypeptides consisting of the amino acid sequence set forth in SEQ ID NO:18, SEQ ID NO:19, SEQ ID NO:20, SEQ ID NO:22, or combinations thereof are immobilized to a solid support.

5. The method of claim 1, wherein the one or more purified *E. canis* polypeptides are attached to a solid support.

6. The method of claim 1, wherein the one or more purified *E. canis* polypeptides are in a multimeric form.

7. The method of claim 2, wherein the one or more purified polypeptides consisting of the amino acid sequence set forth in SEQ ID NO:18, SEQ ID NO:19, SEQ ID NO:20, SEQ ID NO:22, or combinations thereof are in a multimeric form.

8. A method of distinguishing between an animal that has been infected with *E. canis* from an animal that has not been infected with *E. canis*, the method comprising:

(a) contacting a biological sample from an animal with one or more purified polypeptides consisting of the amino acid sequence set forth in SEQ ID NO:18, SEQ ID NO:19, SEQ ID NO:20, SEQ ID NO:22, or combinations thereof, wherein the one or more purified polypeptides are optionally linked to a heterologous protein, an indicator reagent, an amino acid spacer, a signal sequence, a stop transfer sequence, a transmembrane domain, a protein purification ligand, or a combination thereof; and (b) detecting whether antibodies in the sample specifically bind to the one or more purified polypeptides;

wherein if antibodies in the sample specifically bind to the one or more purified polypeptides, then the animal has been infected with *E. canis*.

9. The method of claim 8, wherein the one or more purified polypeptides are attached to a solid support.

10. The method of claim 8, wherein the one or more purified polypeptides are in a multimeric form.

11. A method of distinguishing between animals that (1) have been infected with *Ehrlichia canis* and animals that (2) have not been infected with *E. canis* regardless of whether the animal has been vaccinated with an *E. canis* vaccine, wherein the *E. canis* vaccine does not elicit antibodies that specifically bind to an antigen consisting of SEQ ID NO:18, SEQ ID NO:19, SEQ ID NO:20, or SEQ ID NO:22, the method comprising:

(a) contacting a biological sample from an animal with one or more purified *E. canis* polypeptides that do not specifically bind to antibodies that are a component of the animal's immune response to an *E. canis* vaccine; wherein the one or more purified *E. canis* polypeptides consist of the amino acid sequence set forth in SEQ ID NO:18, SEQ ID NO:19, SEQ ID NO:20, SEQ ID NO:22, or combinations thereof and wherein, optionally, the one or more purified *E. canis* polypeptides are linked to a heterologous protein, an indicator reagent, an amino acid spacer, a signal sequence, a stop transfer sequence, a transmembrane domain, a protein purification ligand, or a combination thereof;

(b) detecting whether antibodies in the sample specifically bind to the one or more purified *E. canis* polypeptides; and (c) wherein if antibodies in the sample specifically bind to the one or more purified *E. canis* polypeptides, then the animal has been infected with *E. canis*.

12. The method of claim 11, wherein the one or more purified *E. canis* polypeptides are attached to a solid support.

13. The method of claim 11, wherein the one or more purified *E. canis* polypeptides are in a multimeric form.

14. The method of claim 11, wherein the *E. canis* vaccine does not comprise an antigen consisting of SEQ ID NO:18, SEQ ID NO:19, SEQ ID NO:20, or SEQ ID NO:22.

* * * * *